(12) United States Patent
Hennequin et al.

(10) Patent No.: US 7,115,615 B2
(45) Date of Patent: Oct. 3, 2006

(54) QUINAZOLINE DERIVATIVES

(75) Inventors: Laurent Francois Andre Hennequin, Reims (FR); Patrick Ple, Reims (FR); Christine Marie Paul Lambert, Reims (FR)

(73) Assignee: AstraZeneca, Sodertalje (SE)

( * ) Notice: Subject to any disclaimer, the term of this patent is extended or adjusted under 35 U.S.C. 154(b) by 0 days.

(21) Appl. No.: 10/344,678

(22) PCT Filed: Aug. 15, 2001

(86) PCT No.: PCT/GB01/03649

§ 371 (c)(1),
(2), (4) Date: Feb. 14, 2003

(87) PCT Pub. No.: WO02/16352

PCT Pub. Date: Feb. 28, 2002

(65) Prior Publication Data

US 2004/0034046 A1    Feb. 19, 2004

(30) Foreign Application Priority Data

Aug. 21, 2000    (EP) ................. 00402320
Apr. 19, 2001    (EP) ................. 01401006

(51) Int. Cl.
| | | |
|---|---|---|
| A01N 43/54 | (2006.01) | |
| A61K 31/517 | (2006.01) | |
| A61K 31/535 | (2006.01) | |
| C07D 239/70 | (2006.01) | |
| C07D 413/00 | (2006.01) | |
| C07D 419/00 | (2006.01) | |

(52) U.S. Cl. .................. 514/266.24; 514/266.2; 514/234.5; 514/252.17; 514/267; 544/116; 544/249; 544/284; 544/293

(58) Field of Classification Search ............. 514/266.2, 514/266.24, 234.5, 252.17, 267; 544/293, 544/284, 249, 116
See application file for complete search history.

(56) References Cited

U.S. PATENT DOCUMENTS

| 5,411,963 A | 5/1995 | Dreikorn et al. ............ 514/259 |
| 5,576,322 A | 11/1996 | Takase et al. ............... 514/260 |
| 5,955,464 A | 9/1999 | Barker ........................ 514/259 |
| 5,962,458 A | 10/1999 | Lohmann et al. ........... 514/259 |
| 6,046,206 A | 4/2000 | Pamukcu et al. ........... 514/259 |
| 6,080,747 A | 6/2000 | Uckun et al. ................ 514/259 |

FOREIGN PATENT DOCUMENTS

| EP | 0 326 330 B1 | 8/1989 |
| EP | 0 520 722 A1 | 12/1992 |
| EP | 0 566 226 A1 | 10/1993 |
| EP | 0 602 851 A1 | 6/1994 |
| EP | 0 607 439 A | 7/1994 |
| EP | 0 787 722 A1 | 8/1997 |
| EP | 0 837 063 A1 | 4/1998 |
| GB | 2 295 387 A | 5/1996 |
| WO | 92/20642 | 11/1992 |
| WO | 93/07124 | 4/1993 |
| WO | 95/15758 | 6/1995 |
| WO | 95/23141 | 8/1995 |
| WO | 95/24190 | 9/1995 |
| WO | 96/09294 | 3/1996 |
| WO | 96/15118 | 5/1996 |
| WO | 96/16960 | 6/1996 |
| WO | 96/30347 | 10/1996 |
| WO | 96/39145 | 12/1996 |
| WO | 97/03069 | 1/1997 |
| WO | 97/22596 | 6/1997 |
| WO | 97/30034 | 8/1997 |
| WO | 97/30035 | 8/1997 |
| WO | 97/30044 | 8/1997 |
| WO | 97/38994 A | 10/1997 |
| WO | 98/13354 A | 4/1998 |
| WO | 98/02434 | 11/1998 |
| WO | 98/50370 | 11/1998 |
| WO | 99/09016 | 2/1999 |
| WO | 99/61428 | 12/1999 |
| WO | 00/00202 | 1/2000 |
| WO | 00/10981 | 3/2000 |
| WO | 00/21955 | 4/2000 |
| WO | 00/47212 | * 8/2000 |
| WO | 00/51991 | 9/2000 |
| WO | 00/55141 | 9/2000 |

(Continued)

*Primary Examiner*—James O. Wilson
*Assistant Examiner*—Tamthom N. Truong
(74) *Attorney, Agent, or Firm*—Morgan Lewis & Bockius LLP

(57) ABSTRACT

The invention concerns quinazoline derivatives of Formula (I)

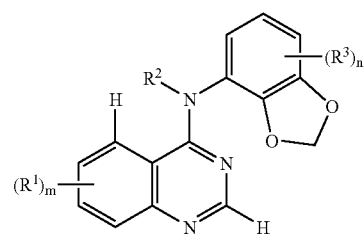

wherein each of m, $R^1$, n, $R^2$ and $R^3$ have any of the meanings defined in the description; processes for their preparation, pharmaceutical compositions containing them and their use in the manufacture of a medicament for use as an anti-invasive agent in the containment and/or treatment of solid tumour disease.

18 Claims, No Drawings

| FOREIGN PATENT DOCUMENTS | | |
|---|---|---|
| WO | 01/21594 | 3/2001 |
| WO | 01/21595 | 3/2001 |
| WO | 01/21596 | 3/2001 |
| WO | 01/77085 | 10/2001 |
| WO | 01/94341 | 12/2001 |
| WO | 01/94341 A1 | 12/2001 |
| WO | 02/34744 A1 | 3/2002 |
| WO | 02/30924 A1 | 4/2002 |
| WO | 02/30926 A1 | 4/2002 |
| WO | 02/085895 A1 | 10/2002 |
| WO | 03/008409 A1 | 1/2003 |

* cited by examiner

QUINAZOLINE DERIVATIVES

The invention concerns certain novel quinazoline derivatives, or pharmaceutically-acceptable salts thereof, which possess anti-tumour activity and are accordingly useful in methods of treatment of the human or animal body. The invention also concerns processes for the manufacture of said quinazoline derivatives, to pharmaceutical compositions containing them and to their use in therapeutic methods, for example in the manufacture of medicaments for use in the prevention or treatment of solid tumour disease in a warm-blooded animal such as man.

Many of the current treatment regimes for cell proliferation diseases such as, psoriasis and cancer utilise compounds which inhibit DNA synthesis. Such compounds are toxic to cells generally but their toxic effect on rapidly dividing cells such as tumour cells can be beneficial. Alternative approaches to anti-tumour agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis*, 1986, 1, 91). Several such oncogenes give rise to the production of peptides which are receptors for growth factors. Activation of the growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al., *Ann. Reports in Med. Chem.*, 1989, Chpt. 13). The first group of tyrosine kinases to be identified arose from such viral oncogenes, for example pp60$^{v-Src}$ tyrosine kinase (otherwise known as v-Src), and the corresponding tyrosine kinases in normal cells, for example pp60$^{c-Src}$ tyrosine kinase (otherwise known as c-Src).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43–73) based on families of growth factors which bind to different receptor tyrosine kinases. The classification includes Class I receptor tyrosine kinases comprising the EGF family of receptor tyrosine kinases such as the EGF, TGFα, Neu and erbB receptors, Class II receptor tyrosine kinases comprising the insulin family of receptor tyrosine kinases such as the insulin and IGFI receptors and insulin-related receptor (IRR) and Class III receptor tyrosine kinases comprising the platelet-derived growth factor (PDGF) family of receptor tyrosine kinases such as the PDGFα, PDGFβ and colony-stimulating factor 1 (CSF1) receptors.

It is also known that certain tyrosine kinases belong to the class of non-receptor tyrosine kinases which are located intracellularly and are involved in the transmission of biochemical signals such as those that influence tumour cell motility, dissemination and invasiveness and subsequently metastatic tumour growth (Ultrich et al., *Cell* 1990, 61 203–212, Bolen et al., *FASEB J.*, 1992, 6, 3403–3409, Brickell et al., *Critical Reviews in Oncogenesis*, 1992, 3, 401–406, Bohlen et al., *Oncogene*, 1993, 8, 2025–2031, Courtneidge et al., *Semin. Cancer Biol.*, 1994, 5, 239–246, Lauffenburger et al., *Cell*, 1996, 84, 359–369, Hanks et al., *BioEssays*, 1996, 19, 137–145, Parsons et al., *Current Opinion in Cell Biology*, 1997, 9, 187–192, Brown et al., *Biochimica et Biophysica Acta*, 1996, 121–149 and Schlaepfer et al., *Progress in Biophysics and Molecular Biology*, 1999, 71, 435–478). Various classes of non-receptor tyrosine kinases are known including the Src family such as the Src, Lyn and Yes tyrosine kinases, the Abl family such as Abl and Arg and the Jak family such as Jak 1 and Tyk 2.

It is known that the Src family of non-receptor tyrosine kinases are highly regulated in normal cells and in the absence of extracellular stimuli are maintained in an inactive conformation. However, some Src family members, for example c-Src tyrosine kinase, is frequently significantly activated (when compared to normal cell levels) in common human cancers such as gastrointestinal cancer, for example colon, rectal and stomach cancer (Cartwright et al., *Proc. Natl. Acad. Sci. USA*, 1990, 87, 558–562 and Mao et al., *Oncogne*, 1997, 15, 3083–3090), and breast cancer (Muthuswamy et al., *Oncogene*, 1995, 11, 1801–1810). The Src family of non-receptor tyrosine kinases has also been located in other common human cancers such as non-small cell lung cancers (NSCLCs) including adenocarcinomas and squamous cell cancer of the lung (Mazurenko et al., *European Journal of Cancer*, 1992, 28, 372–7), bladder cancer (Fanning et al., *Cancer Research*, 1992, 52, 1457–62), oesophageal cancer (Jankowski et al., *Gut*, 1992, 33, 1033–8), cancer of the prostate, ovarian cancer (Wiener et al., *Clin. Cancer Research*, 1999, 5, 2164–70) and pancreatic cancer (Lutz et al., *Biochem. and Biophys. Res. Comm.*, 1998, 243, 503–8). As further human tumour tissues are tested for the Src family of non-receptor tyrosine kinases it is expected that its widespread prevalence, will be established.

It is further known that the predominant role of c-Src non-receptor tyrosine kinase is to regulate the assembly of focal adhesion complexes through interaction with a number of cytoplasmic proteins including, for example, focal adhesion kinase and paxillin. In addition c-Src is coupled to signalling pathways that regulate the actin cytoskeleton which facilitates cell motility. Likewise, important roles are played by the c-Src, c-Yes and c-Fyn non-receptor tyrosine kinases in integrin mediated signalling and in disrupting cadherin-dependent cell-cell junctions (Owens et al., *Molecular Biology of the Cell*, 2000, 11, 51–64 and Klinghoffer et al., *EMBO Journal*, 1999, 18, 2459–2471). Cellular motility is necessarily required for a localised tumour to progress through the stages of dissemination into the blood stream, invasion of other tissues and initiation of metastatic tumour growth. For example, colon tumour progression from localised to disseminated, invasive metastatic disease has been correlated with c-Src non-receptor tyrosine kinase activity (Brunton et al., *Oncogene*, 1997, 14, 283–293, Fincham et al., *EMBO J*, 1998, 17, 81–92 and Verbeek et al., *Exp. Cell Research*, 1999, 248, 531–537).

Accordingly it has been recognised that an inhibitor of such non-receptor tyrosine kinases should be of value as a selective inhibitor of the motility of tumour cells and as a selective inhibitor of the dissemination and invasiveness of mammalian cancer cells leading to inhibition of metastatic tumour growth. In particular an inhibitor of such non-receptor tyrosine kinases should be of value as an anti-invasive agent for use in the containment and/or treatment of solid tumour disease.

We have now found that surprisingly certain quinazoline derivatives possess potent anti-tumour activity. Without wishing to imply that the compounds disclosed in the present invention possess pharmacological activity only by virtue of an effect on a single biological process, it is believed that the compounds provide an anti-tumour effect by way of inhibition of one or more of the non-receptor tyrosine-specific protein kinases that are involved in the signal transduction steps which lead to the invasiveness and migratory ability of metastasising tumour cells. In particular, it is believed that the compounds of the present invention provide an anti-tumour effect by way of inhibition of the Src family of non-receptor tyrosine kinases, for example by inhibition of one or more of c-Src, c-Yes and c-Fyn.

It is also known that c-Src non-receptor tyrosine kinase enzyme is involved in the control of osteoclast-driven bone resorption (Soriano et al., *Cell,* 1991, 64, 693–702; Boyce et al., *J. Clin. Invest.,* 1992, 90, 1622–1627; Yoneda et al., *J. Clin. Invest.,* 1993, 91, 2791–2795 and Missbach et al., *Bone,* 1999, 24, 437–49). An inhibitor of c-Src non-receptor tyrosine kinase is therefore of value in the prevention and treatment of bone diseases such as osteoporosis, Paget's disease, metastatic disease in bone and tumour-induced hypercalcaemia.

The compounds of the present invention are also useful in inhibiting the uncontrolled cellular proliferation which arises from various non-malignant diseases such as inflammatory diseases (for example rheumatoid arthritis and inflammatory bowel disease), fibrotic diseases (for example hepatic cirrhosis and lung fibrosis), glomerulonephritis, multiple sclerosis, psoriasis, hypersensitivity reactions of the skin, blood vessel diseases (for example atherosclerosis and restenosis), allergic asthma, insulin-dependent diabetes, diabetic retinopathy and diabetic nephropathy.

Generally the compounds of the present invention possess potent inhibitory activity against the Src family of non-receptor tyrosine kinases, for example by inhibition of c-Src and/or c-Yes, whilst possessing less potent inhibitory activity against other tyrosine kinase enzymes such as the receptor tyrosine kinases, for example EGF receptor tyrosine kinase and/or VEGF receptor tyrosine kinase. Furthermore, certain compounds of the present invention possess substantially better potency against the Src family of non-receptor tyrosine kinases, for example c-Src and/or c-Yes, than against VEGF receptor tyrosine kinase. Such compounds possess sufficient potency against the Src family of non-receptor tyrosine kinases, for example c-Src and/or c-Yes, that they may be used in an amount sufficient to inhibit, for example, c-Src and/or c-Yes whilst demonstrating little activity against VEGF receptor tyrosine kinase.

According to one aspect of the invention there is provided a quinazoline derivative of the Formula I

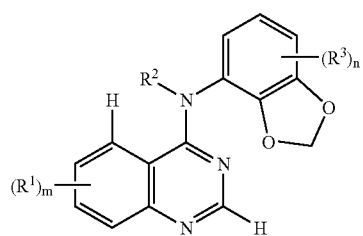

I wherein m is 0, 1, 2 or 3;

each $R^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$Q^1$-$X^1$— wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C)alkylenedioxy, and wherein adjacent carbon atoms in any (2–6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(^5)CO$, $SO_2N(R^5)$, $N(R^5)SO_2$, CH=CH and C≡C wherein $R^5$ is hydrogen or (1–6C)alkyl or, when the inserted group is $N(R^5)$, $R^5$ may also be (2–6C)alkanoyl, and wherein any $CH_2$=CH— or HC≡C— group within a $R^1$ substituent optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^2$-$X^2$— wherein $X^2$ is a direct bond or is selected from CO and $N(R^6)CO$, wherein $R^6$ is hydrogen or (1–6C)alkyl, and $Q^2$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^3$-$Q^3$ wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^4$—R$^8$ wherein $X^4$ is a direct bond or is selected from O and N(R$^9$), wherein $R^9$ is hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, or from a group of the formula:

—X$^5$-Q$^4$ wherein $X^5$ is a direct bond or is selected from O, N(R$^{10}$) and CO, wherein $R^{10}$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and wherein any heterocyclyl group within a substituent on $R^1$ optionally bears 1 or 2 oxo or thioxo substituents;

$R^2$ is hydrogen or (1–6C)alkyl;

n is 0, 1, 2 or 3; and $R^3$ is halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^6$—R$^{11}$ wherein $X^6$ is a direct bond or is selected from O and N(R$^{12}$), wherein $R^{12}$ is hydrogen or (1–6C)alkyl, and $R^{11}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—X$^7$-Q$^5$ wherein $X^7$ is a direct bond or is selected from O, S, SO, SO$_2$, N(R$^{13}$), CO, CH(OR$^{13}$), CON(R$^{13}$), N(R$^{13}$)CO, SO$_2$N(R$^{13}$), N(R$^{13}$)SO$_2$, C(R$^{13}$)$_2$O, C(R$^{13}$)$_2$S and N(R$^{13}$)C(R$^{13}$)$_2$, wherein $R^{13}$ is hydrogen or (1–6C)alkyl, and $Q^5$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and any heterocyclyl group within $Q^5$ optionally bears 1 or 2 oxo or thioxo substituents, or a pharmaceutically-acceptable salt thereof.

In this specification the generic term "alkyl" includes both straight-chain and branched-chain alkyl groups such as propyl, isopropyl and tert-butyl, and also (3–7C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1–6C)alkoxy includes methoxy, ethoxy, cyclopropyloxy and cyclopentyloxy, (1–6C)alkylamino includes methylamino, ethylamino, cyclobutylamino and cyclohexylamino, and di-[(1–6Calkyl]amino includes dimethylamino, diethylamino, N-cyclobutyl-N-methylamino and N-cyclohexyl-N-ethylamino.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for any one of the 'Q' groups ($Q^1$ to $Q^5$) when it is aryl or for the aryl group within a 'Q' group is, for example, phenyl or naphthyl, preferably phenyl.

A suitable value for any one of the 'Q' groups ($Q^1$ or $Q^3$) when it is (3–7C)cycloalkyl or for the (3–7C)cycloalkyl group within a 'Q' group is, for example, cyclopropyl, cyclobutyl, cyclopentyl, cyclohexyl, cycloheptyl or bicyclo[2.2.1]heptyl and a suitable value for any one of the 'Q' groups ($Q^1$ or $Q^3$) when it is (3–7C)cycloalkenyl or for the (3–7C)cycloalkenyl group within a 'Q' group is, for example, cyclobutenyl, cyclopentenyl, cyclohexenyl or cycloheptenyl.

A suitable value for any one of the 'Q' groups ($Q^1$ to $Q^5$) when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

A suitable value for any one of the 'Q' groups ($Q^1$ to $Q^5$) when it is heterocyclyl or for the heterocyclyl group within a 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, oxepanyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl, preferably tetrahydrofuranyl, tetrahydropyranyl, pyrrolidinyl, morpholinyl, 1,1-dioxotetrahydro-4H-1,4-thiazinyl, piperidinyl or piperazinyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for a 'Q' group when it is heteroaryl-(1–6C)alkyl is, for example, heteroarylmethyl, 2-heteroarylethyl and 3-heteroarylpropyl. The invention comprises corresponding suitable values for 'Q' groups when, for example, rather than a heteroaryl-(1–6C)alkyl group, an aryl-(1–6C)alkyl, (3–7C)cycloalkyl-(1–6C)alkyl, (3–7C)cycloalkenyl-(1–6C)alkyl or heterocyclyl-(1–6C)alkyl group is present.

In structural Formula I there is a hydrogen atom at each of the 2- and 5-positions on the quinazoline ring. It is to be understood thereby that the $R^1$ substituents may only be located at the 6-, 7- or 8-positions on the quinazoline ring i.e. that the 2- and 5-positions remain unsubstituted. It is further to be understood that the $R^3$ group that may be present on the 2,3-methylenedioxyphenyl group within structural Formula I may be located on the phenyl ring or on the methylene group within the 2,3-methylenedioxy group. Preferably, any $R^3$ group that is present on the 2,3-methylenedioxyphenyl group within structural Formula I is located on the phenyl ring thereof.

Suitable values for any of the 'R' groups ($R^1$ to $R^{13}$) or for various groups within an $R^1$ or $R^3$ substituent include:

| | |
|---|---|
| for halogeno | fluoro, chloro, bromo and iodo; |
| for (1-6C)alkyl: | methyl, ethyl, propyl, isopropyl and tert-butyl; |
| for (2-8C)alkenyl: | vinyl, isopropenyl, allyl and but-2-enyl; |
| for (2-8C)alkynyl: | ethynyl, 2-propynyl and but-2-ynyl; |
| for (1-6C)alkoxy: | methoxy, ethoxy, propoxy, isopropoxy and butoxy; |
| for (2-6C)alkenyloxy: | vinyloxy and allyloxy; |
| for (2-6C)alkynyloxy: | ethynyloxy and 2-propynyloxy; |
| for (1-6C)alkylthio: | methylthio, ethylthio and propylthio; |
| for (1-6C)alkylsulphinyl: | methylsulphinyl and ethylsulphinyl; |
| for (1-6C)alkylsulphonyl: | methylsulphonyl and ethylsulphonyl; |
| for (1-6C)alkylamino: | methylamino, ethylamino, propylamino, isopropylamino and butylamino; |
| for di-[(1-6C)alkyl]amino: | dimethylamino, diethylamino, N-ethyl-N-methylamino and diisopropylamino; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl and propionyl; |
| for (2-6C)alkanoyloxy: | acetoxy and propionyloxy; |
| for (2-6C)alkanoylamino: | acetamido and propionamido; |
| for N-(1-6C)alkyl-(2-6C)alkanoylamino: | N-methylacetamido and N-methylpropionamido; |
| for N-(1-6C)alkylsulphamoyl: | N-methylsulphamoyl and N-ethylsulphamoyl; |
| for N,N-di-[(1-6C)alkyl]sulphamoyl: | N,N-dimethylsulphamoyl; |
| for (1-6C)alkanesulphonylamino: | methanesulphonylamino and ethanesulphonylamino; |
| for N-(1-6C)alkyl-(1-6C)alkanesulphonylamino: | N-methylmethanesulphonylamino and N-methylethanesulphonylamino; |
| for (3-6C)alkenoylamino: | acrylamido, methacrylamido and crotonamido; |
| for N-(1-6C)alkyl-(3-6C)alkenoylamino: | N-methylacrylamido and N-methylcrotonamido; |
| for (3-6C)alkynoylamino: | propiolamido; |
| for N-(1-6C)alkyl-(3-6C)alkynoylamino: | N-methylpropiolamido; |
| for amino-(1-6C)alkyl: | aminomethyl, 2-aminoethyl, 1-aminoethyl and 3-aminopropyl; |
| for (1-6C)alkylamino-(1-6C)alkyl: | methylaminomethyl, ethylaminomethyl, 1-methylaminoethyl, 2-methylaminoethyl, 2-ethylaminoethyl and 3-methylaminopropyl; |
| for di-[(1-6C)alkyl]amino-(1-6C)alkyl: | dimethylaminomethyl, diethylaminomethyl, 1-dimethylaminoethyl, 2-dimethylaminoethyl and 3-dimethylaminopropyl; |
| for halogeno-(1-6C)alkyl: | chloromethyl, 2-chloroethyl, 1-chloroethyl and 3-chloropropyl; |
| for hydroxy-(1-6C)alkyl: | hydroxymethyl, 2-hydroxyethyl, 1-hydroxyethyl and 3-hydroxypropyl; |
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |

-continued

| | |
|---|---|
| for cyano-(1-6C)alkyl: | cyanomethyl, 2-cyanoethyl, 1-cyanoethyl and 3-cyanopropyl; |
| for (2-6C)alkanoylamino-(1-6C)alkyl: | acetamidomethyl, propionamidomethyl and 2-acetamidoethyl; and |
| for (1-6C)alkoxycarbonylamino-(1-6C)alkyl: | methoxycarbonylaminomethyl, ethoxycarbonylaminomethyl, tert-butoxycarbonylaminomethyl and 2-methoxycarbonylaminoethyl. |

A suitable value for $(R^1)_m$ when it is a (1–3C)alkylenedioxy group is, for example, methylenedioxy or ethylenedioxy and the oxygen atoms thereof occupy adjacent ring positions.

When, as defined hereinbefore, an $R^1$ group forms a group of the formula $Q^1$-$X^1$— and, for example, $X^1$ is a $OC(R^4)_2$ linking group, it is the carbon atom, not the oxygen atom, of the $OC(R^4)_2$ linking group which is attached to the quinazoline ring and the oxygen atom is attached to the $Q^1$ group. Similarly, when, for example a $CH_3$ group within a $R^1$ substituent bears a group of the formula —$X^3$-$Q^3$ and, for example, $X^3$ is a $C(R^7)_2O$ linking group, it is the carbon atom, not the oxygen atom, of the $C(R^7)_2O$ linking group which is attached to the $CH_3$ group and the oxygen atom is linked to the $Q^3$ group. A similar convention applies to the attachment of the groups of the formulae $Q^2$-$X^2$— and —$X^7$-$Q^5$.

As defined hereinbefore, adjacent carbon atoms in any (2–6C)alkylene chain within a $R^1$ substituent may be optionally separated by the insertion into the chain of a group such as O, $CON(R^5)$ or C≡C. For example, insertion of a C≡C group into the ethylene chain within a 2-morpholinoethoxy group gives rise to a 4-morpholinobut-2-ynyloxy group and, for example, insertion of a CONH group into the ethylene chain within a 3-methoxypropoxy group gives rise to, for example, a 2-(2-methoxyacetamido)ethoxy group.

When, as defined hereinbefore, any $CH_2$=CH— or HC≡C— group within a $R^1$ substituent optionally bears at the terminal $CH_2$= or HC≡ position a substituent such as a group of the formula $Q^2$-$X^2$— wherein $X^2$ is, for example, NHCO and $Q^2$ is a heterocyclyl-(1–6C)alkyl group, suitable $R^1$ substituents so formed include, for example, N-[heterocyclyl-(1–6C)alkyl]carbamoylvinyl groups such as N-(2-pyrrolidin-1-ylethyl)carbamoylvinyl or N-[heterocyclyl-(1–6C)alkyl]carbamoylethynyl groups such as N-(2-pyrrolidin-1-ylethyl)carbamoylethynyl.

When, as defined hereinbefore, any $CH_2$ or $CH_3$ group within a $R^1$ substituent optionally bears on each said $CH_2$ or $CH_3$ group one or more halogeno or (1–6C)alkyl substituents, there are suitably 1 or 2 halogeno or (1–6C)alkyl substituents present on each said $CH_2$ group and there are suitably 1, 2 or 3 such substituents present on each said $CH_3$ group.

When, as defined hereinbefore, any $CH_2$ or $CH_3$ group within a $R^1$ substituent optionally bears on each said $CH_2$ or $CH_3$ group a substituent as defined hereinbefore, suitable $R^1$ substituents so formed include, for example, hydroxy-substituted heterocyclyl-(1–6C)alkoxy groups such as 2-hydroxy-3-piperidinopropoxy and 2-hydroxy-3-morpholinopropoxy, hydroxy-substituted amino-(2–6C)alkoxy groups such as 3-amino-2-hydroxypropoxy, hydroxy-substituted (1–6C)alkylamino-(2–6C)alkoxy groups such as 2-hydroxy-3-methylaminopropoxy, hydroxy-substituted di-[(1–6C)alkyl]amino-(2–6C)alkoxy groups such as 3-dimethylamino-2-hydroxypropoxy, hydroxy-substituted heterocyclyl-(1–6C)alkylamino groups such as 2-hydroxy-3-piperidinopropylamino and 2-hydroxy-3-morpholinopropylamino, hydroxy-substituted amino-(2–6C)alkylamino groups such as 3-amino-2-hydroxypropylamino, hydroxy-substituted (1–6C)alkylamino-(2–6C)alkylamino groups such as 2-hydroxy-3-methylaminopropylamino, hydroxy-substituted di-[(1–6C)alkyl]amino-(2–6C)alkylamino groups such as 3-dimethylamino-2-hydroxypropylamino, hydroxy-substituted (1–6C)alkoxy groups such as 2-hydroxyethoxy, (1–6C)alkoxy-substituted (1–6C)alkoxy groups such as 2-methoxyethoxy and 3-ethoxypropoxy, (1–6C)alkylsulphonyl-substituted (1–6C)alkoxy groups such as 2-methylsulphonylethoxy and heterocyclyl-substituted (1–6C)alkylamino-(1–6C)alkyl groups such as 2-morpholinoethylaminomethyl, 2-piperazin-1-ylethylaminomethyl and 3-morpholinopropylaminomethyl.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, quinazoline derivatives of the Formula I, or pharmaceutically-acceptable salts thereof, wherein, unless otherwise stated, each of m, $R^1$, $R^2$, n and $R^3$ has any of the meanings defined hereinbefore or in paragraphs (a) to (k) hereinafter:

(a) m is 1 or 2, and each $R^1$ group, which may be the same or different, is selected from halogeno, trifluoromethyl, hydroxy, amino, carbamoyl, (1–6C)alkyl, (2–8C)alkenyl, (2–8C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino and N-(1–6C)alkyl-(3–6C)alkynoylamino, or from a group of the formula:

$Q^1$-$X^1$— wherein $X^1$ is a direct bond or is selected from O, $N(R^4)$, $CON(R^4)$, $N(R^4)CO$ and $OC(R^4)_2$ wherein $R^4$ is hydrogen or (1–6C)alkyl, and $Q^1$ is aryl, aryl-(1–6C)alkyl, cycloalkyl-(1–6C)alkyl, heteroaryl, heteroaryl-(1–6C) alkyl, heterocyclyl or heterocyclyl-(1–6C)alkyl, and wherein adjacent carbon atoms in any (2–6C)alkylene chain within a $R^1$ substituent are optionally separated by the insertion into the chain of a group selected from O, $N(R^5)$, $CON(R^5)$, $N(R^5)CO$, CH=CH and C≡C wherein $R^5$ is hydrogen or (1–6C)alkyl, or, when the inserted group is $N(R^5)$, $R^5$ may also be (2–6C)alkanoyl, and wherein any $CH_2$=CH— or HC≡C— group within a $R^1$ substituent optionally bears at the terminal $CH_2$= or HC≡C— position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^2$-$X^2$— wherein $X^2$ is a direct bond or is CO or $N(R^6)$CO, wherein $R^6$ is hydrogen or (1–6C)alkyl, and $Q^2$ is heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group a substituent selected from hydroxy, amino, (1–6C)alkoxy, (1–6C)alkylsulphonyl, (1–6C)alkylamino, di-[(1–6C)alkyl]amino, (2–6C)alkanoyloxy, (2–6C)alkanoylamino and N-(1–6C)alkyl-(2–6C)alkanoylamino, or from a group of the formula:

—$X^3$-$Q^3$ wherein $X^3$ is a direct bond or is selected from O, $N(R^6)$, $CON(R^7)$, $N(R^7)$CO and $C(R^7)_2$O, wherein $R^7$ is hydrogen or (1–6C)alkyl, and $Q^3$ is heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or optionally bears 1 substituent selected from a group of the formula:

—$X^4$-$R^8$ wherein $X^4$ is a direct bond or is selected from O and $N(R^9)$, wherein $R^9$ is hydrogen or (1–6C)alkyl, and $R^8$ is hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, and from a group of the formula:

—$X^5$-$Q^4$ wherein $X^5$ is a direct bond or is selected from O, $N(R^{10})$ and CO, wherein $R^{10}$ is hydrogen or (1–6C)alkyl, and $Q^4$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo substituents;

(b) m is 1 or 2, and each $R^1$ group, which may be the same or different, is selected from fluoro, chloro, trifluoromethyl, hydroxy, amino, carbamoyl, methyl, ethyl, propyl, butyl, vinyl, ethynyl, methoxy, ethoxy, propoxy, isopropoxy, butoxy, methylamino, ethylamino, propylamino, dimethylamino, diethylamino, dipropylamino, N-methylcarbamoyl, N,N-dimethylcarbamoyl, acetamido, propionamido, acrylamido and propiolamido, or from a group of the formula:

$Q^1$-$X^1$— wherein $X^1$ is a direct bond or is selected from O, NH, CONH, NHCO and $OCH_2$ and $Q^1$ is phenyl, benzyl, cyclopropylmethyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4-pyridylmethyl, 2-(2-, 3- or 4-pyridyl)ethyl, 3-(2-, 3- or 4-pyridyl)propyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-pipelidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2–6C)alkylene chain within a $R^1$ substituent are optionally separated by the insertion into the chain of a group selected from O, NH, CONH, NHCO, CH=CH and C≡C, and wherein any $CH_2$=CH— or HC≡C— group within a $R^1$ substituent optionally bears at the terminal $CH_2$= or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl, 3-aminopropyl, 4-aminobutyl, methylaminomethyl, 2-methylaminoethyl, 3-methylaminopropyl, 4-methylaminobutyl, dimethylaminomethyl, 2-dimethylaminoethyl, 3-dimethylaminopropyl or 4-dimethylaminobutyl, or from a group of the formula:

$Q^2$-$X^2$— wherein $X^2$ is a direct bond or is CO, NHCO or N(Me)CO and $Q^2$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino, dimethylamino, diisopropylamino, N-ethyl-N-methylamino, N-isopropyl- N-methylamino, N-methyl-N-propylamino, acetoxy, acetamido and N-methylacetamido or from a group of the formula:

$$—X^3-Q^3$$

wherein $X^3$ is a direct bond or is selected from O, NH, CONH, NHCO and $CH_2O$ and $Q^3$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl, methoxy, N-methylcarbamoyl and N,N-dimethylcarbamoyl, or optionally bears 1 substituent selected from a group of the formula:

$$—X^4-R^8$$

wherein $X^4$ is a direct bond or is selected from O and NH and $R^8$ is 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

$$—X^5-Q^4$$

wherein $X^5$ is a direct bond or is selected from O, NH and CO and $Q^4$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(c) m is 1 or 2 and each $R^1$ group, which may be the same or different, is located at the 6- and/or 7-positions and is selected from hydroxy, amino, methyl, ethyl, propyl, butyl, vinyl, ethynyl, methoxy, ethoxy, propoxy, isopropoxy, butoxy, methylamino, ethylamino, dimethylamino, diethylamino, acetamido, propionamido, cyclopentyloxy, cyclohexyloxy, phenoxy, benzyloxy, tetrahydrofuran-3-yloxy, tetrahydropyran-3-yloxy, tetrahydropyran-4-yloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, pyrid-2-ylmethoxy, pyrid-3-ylmethoxy, pyrid-4-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, pyrrolidin-1-yl, morpholino, piperidino, piperazin-1-yl, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy, 3-homopiperazin-1-ylpropoxy, 2-pyrrolidin-1-ylethylamino, 3-pyrrolidin-1-ylpropylamino, 4-pyrrolidin-1-ylbutylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 4-morpholinobutylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, 4-piperidinobutylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 4-piperazin-1-ylbutylamino, 2-homopiperazin-1-ylethylamino or 3-homopiperazin-1-ylpropylamino, and wherein adjacent carbon atoms in any (2–6C)alkylene chain within a $R^1$ substituent are optionally separated by the insertion into the chain of a group selected from O, NH, CH═CH and C≡C, and when $R^1$ is a vinyl or ethynyl group, the $R^1$ substituent optionally bears at the terminal $CH_2$═ or HC≡ position a substituent selected from N-(2-dimethylaminoethyl)carbamoyl, N-(3-dimethylaminopropyl)carbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$$Q^2-X^2—$$

wherein $X^2$ is a direct bond or is NHCO or N(Me)CO and $Q^2$ is imidazolylmethyl, 2-imidazolylethyl, 3-imidazolylpropyl, pyridylmethyl, 2-pyridylethyl, 3-pyridylpropyl, pyrrolidin-1-ylmethyl, 2-pyrrolidin-1-ylethyl, 3-pyrrolidin-1-ylpropyl, 4pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido, and wherein any phenyl, imidazolyl, triazolyl, pyridyl or heterocyclyl group within a substituent on $R^1$ optionally bears 1 or 2 substituents, which may be the same or different, selected from fluoro, chloro, tlifluoromethyl, hydroxy, amino, carbamoyl, methyl, ethyl, N-methylcarbamoyl, N,N-dimethylcarbarnoyl and methoxy, and a pyrrolidin-2-yl, piperidin-3-yl, piperidin-4-yl, piperazin-1-yl or homopiperazin-1-yl group within a $R^1$ substituent is optionally N-substituted with 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(d) m is 1 and the $R^1$ group is located at the 6- or 7-position and is selected from hydroxy, amino, methyl, ethyl, propyl, butyl, methoxy, ethoxy, propoxy, isopropoxy, butoxy, methylamino, ethylamino, dimethylamino, diethylamino, acetamido, propionamido, benzyloxy, 2-imidazol-1-ylethoxy, 2-(1,2,3-triazol-1-yl)ethoxy, 2-(1,2,4-triazol-1-yl)ethoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy or 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino, dimethylamino, diisopropylamino, N-ethyl-N-methylamino, N-isopropyl-N-methylamino and acetoxy, and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

(e) $R^2$ is hydrogen;

(f) n is 1 or 2 and the $R^3$ groups, which may be the same or different, are located at the 5- and/or 6-positions of the 2,3-methylenedioxyphenyl group and are selected from halogeno, trifluoromethyl, cyano, hydroxy, (1–6C)alkyl, (2–8C)alkenyl, (2–8C)alkynyl and (1–6C)alkoxy;

(g) n is 1 or 2 and the $R^3$ groups, which may be the same or different, are located at the 5- and/or 6-positions of the 2,3-methylenedioxyphenyl group and are selected from fluoro, chloro, bromo, iodo, trifluoromethyl, cyano, hydroxy, methyl, ethyl, vinyl, allyl, isopropenyl, ethynyl, 1-propynyl, 2-propynyl, methoxy and ethoxy;

(h) n is 1 and the $R^3$ group is located at the 5- or 6-position of the 2,3-methylenedioxyphenyl group, especially the 6-position, and is selected from chloro, bromo, trifluoromethyl, cyano, hydroxy, methyl, ethyl, methoxy and ethoxy;

(i) n is 1 and the $R^3$ group is located at the 6-position of the 2,3-methylenedioxyphenyl group and is selected from chloro, bromo and trifluoromethyl;

(j) n is 0; and (k) m is 2 and each $R^1$ group, which may be the same or different, is located at the 6- and/or 7-positions and is selected from hydroxy, amino, methyl, ethyl, methoxy, ethoxy, propoxy, isopropoxy, butoxy, methylamino, ethylamino, dimethylamino, diethylamino, acetamido, propionamido, benzyloxy, 2-pyrrol-1-ylethoxy, 3-pyrrol-1-ylpropoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, 2-pyridylmethoxy, 3-pyridylmethoxy, 4-pyridylmethoxy, 2-tetrahydropyran-4-ylethoxy, 3-tetrahydropyran-4-ylpropoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy or 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino, dimethylamino, diethylamino, diisopropylamino, N-ethyl-N-methylamino, N-isopropyl-N-methylamino, N-isobutyl-N-methylamino, N-allyl-N-methylamino, acetoxy, acetamido, N-methylacetamido, 2-pyridyloxy, 3-pyridyloxy and 4-pyridyloxy, and wherein any phenyl, pyrrolyl, imidazolyl, triazolyl, pyridyl or heterocyclyl group within a substituent on $R^1$ optionally bears 1, 2 or 3 substituents, which may be the same or different, selected from fluoro, chloro, trifluoromethyl, cyano, hydroxy, amino, carbamoyl, methyl, ethyl, N-methylcarbamoyl, N,N-dimethylcarbamoyl, methoxy, methoxymethyl and morpholinomethyl, and a pyrrolidin-2-yl, piperidin-3-yl, piperidin-4-yl, piperazin-1-yl or homopiperazin-1-yl group within a $R^1$ substituent is optionally N-substituted with methyl, ethyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents.

A preferred compound of the invention is a quinazoline derivative of the Formula I wherein:

m is 1 or 2 and each $R^1$ group, which may be the same or different, is located at the 6- and/or 7-positions and is selected from hydroxy, amino, methyl, ethyl, propyl, butyl, methoxy, ethoxy, propoxy, isopropoxy, butoxy, methylamino, ethylamino, dimethylamino, diethylamino, acetamido, propionamido, 2-imidazol-1-ylethoxy, 2-(1,2,4-triazol-1-yl)ethoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy and 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino, dimethylamino, diethylamino, N-ethyl-N-methylamino, N-isopropyl-N-methylamino, N-methyl-N-propylamino and acetoxy;

and wherein any heteroaryl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, methoxy, N-methylcarbamoyl and N,N-dimethylcarbamoyl and a pyrrolidin-2-yl, piperidin-3-yl, piperidin4-yl, piperazin-1-yl or homopiperazin-1-yl group within a $R^1$ substituent is optionally N-substituted with 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

$R^2$ is hydrogen, n is 0 or 1 and the $R^3$ group, if present, is located at the 5- or 6-position of the 2,3-methylenedioxyphenyl group and is selected from fluoro, chloro, trifluoromethyl, cyano, hydroxy, methyl, ethyl, vinyl, allyl, ethynyl, methoxy and ethoxy; or a pharmaceutically-acceptable acid-addition salt thereof.

A further preferred compound of the invention is a quinazoline derivative of the Formula I wherein:

m is 2 and each $R^1$ group, which may be the same or different, is located at the 6- and/or 7-positions and is selected from hydroxy, amino, methyl, ethyl, methoxy, ethoxy, propoxy, isopropoxy, butoxy, methylamino, ethylamino, dimethylamino, diethylamino, acetamido, propionamido, benzyloxy, 2-pyrrol-1-ylethoxy, 3-pyrrol-1-ylpropoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, 2-pyridylmethoxy, 3-pyridylmethoxy, 4-pyridylmethoxy, 2-tetrahydropyran-4-ylethoxy, 3-tetrahydropyran-4-ylpropoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy or 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino, dimethylamino, diethylamino, diisopropylamino, N-ethyl-N-methylamino, N-isopropyl-N-methylamino, N-isobutyl-N-methylamino, N-allyl-N-methylamino, acetoxy, acetamido, N-methylacetamido, 2-pyridyloxy, 3-pyridyloxy and 4-pyridyloxy, and wherein any phenyl, pyrrolyl, imidazolyl, triazolyl, pyridyl or heterocyclyl group within a substituent on $R^1$ optionally bears 1, 2 or 3 substituents, which may be the same or different, selected from fluoro, chloro, trifluoromethyl, cyano, hydroxy, amino, carbamoyl, methyl, ethyl, N-methylcarbamoyl, N,N-dimethylcarbamoyl, methoxy, methoxymethyl and morpholinomethyl, and a pyrrolidin-2-yl, piperidin-3-yl, piperidin-4-yl, piperazin-1-yl or homopiperazin-1-yl group within a $R^1$ substituent is optionally N-substituted with methyl, ethyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

$R^2$ is hydrogen;

n is 0 or 1 and the $R^3$ group, if present, is located at the 6-position of the 2,3-methylenedioxyphenyl group and is selected from chloro, bromo and trifluoromethyl; or a pharmaceutically-acceptable acid-addition salt thereof.

A further preferred compound of the invention is a quinazoline derivative of the Formula I wherein:

m is 2 and the first $R^1$ group is located at the 6-position and is selected from hydroxy, methoxy, ethoxy and propoxy, and the second $R^1$ group is located at the 7-position and is selected from 2-dimethylaminoethoxy, 3-dimethylaminopropoxy, 4-dimethylaminobutoxy, 2-diethylaminoethoxy, 3-diethylaminopropoxy, 4-diethylaminobutoxy, 2-diisopropylaminoethoxy, 3-diisopropylaminopropoxy, 4-diisopropylaminobutoxy, 2-N-isopropyl-N-methylamino)ethoxy, 3-(N-isopropyl-N-methylamino)propoxy, 4-(N-isopropyl-N-methylamino)butoxy, 2pyrrolidin-1-ylethoxy, 3-pyrrolidin-1-ylpropoxy, 4-pyrrolidin-1-ylbutoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 4-(4-methylpiperazin-1-yl)butoxy, 2-(4-cyanomethylpiperazin-1-yl)ethoxy, 3-(4-cyanomethylpiperazin-1-yl)propoxy, 4-(4-cyanomethylpiperazin-1-yl)butoxy, 2-[2-(4-methylpiperazin-1-yl)ethoxy]ethoxy, 2-methylsulphonylethoxy and 3-methylsulphonylpropoxy, and wherein any $CH_2$ group within the second $R^1$ group that is attached to two carbon atoms optionally bears a hydroxy group or acetoxy group on said $CH_2$ group, and wherein any heterocyclyl group within the second $R^1$ group optionally bears 1 or 2 oxo substituents;

$R^2$ is hydrogen; and n is 0 or n is 1 and the $R^3$ group is located at the 5- or 6-position of the 2,3-methylenedioxyphenyl group and is selected from fluoro, chloro, trifluoromethyl, cyano, methyl, ethyl, ethynyl, methoxy and ethoxy; or a pharmaceutically-acceptable acid-addition salt thereof.

A further preferred compound of the invention is a quinazoline derivative of the Formula I wherein:

m is 2 and the first $R^1$ group is a 6-methoxy group and the second $R^1$ group is located at the 7-position and is selected from 2-dimethylaminoethoxy, 3-dimethylaminopropoxy, 4-dimethylaminobutoxy, 2-diethylaminoethoxy, 3-diethylaminopropoxy, 4-diethylaminobutoxy, 2-diisopropylaminoethoxy, 3-diisopropylaminopropoxy, 4-diisopropylaminobutoxy, 2-(N-isopropyl-N-methylamino)ethoxy, 3-(N-isopropyl-N-methylamino)propoxy, 4-(N-isopropyl-N-methylamino)butoxy, 2-(N-isobutyl-N-methylamino)ethoxy, 3-(N-isobutyl-N-methylamino)propoxy, 4-(N-isobutyl-N-methylamino)butoxy, 2-(N-allyl-N-methylamino)ethoxy, 3-(N-allyl-N-methylamino)propoxy, 4-(N-allyl-N-methylamino)butoxy, 2-pyrrolidin-1-ylethoxy, 3-pyrrolidin-1-ylpropoxy, 4-pyrrolidin-1-ylbutoxy, pyrrolidin-3-yloxy, N-methylpyrrolidin-3-yloxy, pyrrolidin-2-ylmethoxy, 2-pyrrolidin-2-ylethoxy, 3-pyrrolidin-2ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, N-cyanomethylpiperidin-3-ylmethoxy, piperidin-4-ylmethoxy, N-methylpiperidin-4-ylmethoxy, N-cyanomethylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-homopiperidin-1-ylethoxy, 3-homopiperidin-1-ylpropoxy, 4-homopiperidin-1-ylbutoxy, 2-piperazin-1-ylethoxy, 2-(4-methylpiperazin-1-yl)ethoxy, 3-piperazin-1-ylpropoxy, 3-(4-methylpiperazin-1-yl)propoxy, 4-piperazin-1-ylbutoxy, 4-(4-methylpiperazin-1-yl)butoxy, 2-(4-cyanomethylpiperazin-1-yl)ethoxy, 3-(4-cyanomethylpiperazin-1-yl)propoxy, 4-(4-cyanomethylpiperazin-1-yl)butoxy, 2-(2-piperazin-1-ylethoxy)ethoxy, 2-[2-(4-methylpiperazin-1-yl)ethoxy]ethoxy, 2-methylsulphonylethoxy, 3-methylsulphonylpropoxy, 2-tetrahydropyran-4-ylethoxy, 3-tetrahydropyran-4-ylpropoxy, 2-pyrrol-1-ylethoxy, 3-pyrrol-1-ylpropoxy, 2-(2-pyridyloxy)ethoxy, 3-(2-pyridyloxy)propoxy, 2-(3-pyridyloxy)ethoxy, 3-(3-pyridyloxy)propoxy, 2-(4-pyridyloxy)ethoxy, 3-(4-pyridyloxy)propoxy, 2-pyridylmethoxy, 3-pyridylmethoxy and 4-pyridylmethoxy, and wherein any $CH_2$ group within the second $R^1$ group that is attached to two carbon atoms optionally bears a hydroxy group on said $CH_2$ group, and wherein any heteroaryl group within the second $R^1$ group optionally bears 1 or 2 substituents selected from chloro, cyano, hydroxy and methyl, and any heterocyclyl group within the second $R^1$ group optionally bears 1 or 2 substituents selected from hydroxy, methyl and oxo;

$R^2$ is hydrogen; and n is 0 or n is 1 and the $R^3$ group is located at the 6-position of the 2,3-methylenedioxyphenyl group and is selected from chloro and bromo; or a pharmaceutically-acceptable acid-addition salt thereof.

A further preferred compound of the invention is a quinazoline derivative of the Formula I wherein:

m is 2 and the first $R^1$ group is a 6-methoxy group and the second $R^1$ group is located at the 7-position and is selected from 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 2-(4-cyanomethylpiperazin-1-yl)ethoxy, 3-(4cyanomethylpiperazin-1-yl)propoxy, 2-[2-(4-methylpiperazin-1-yl)ethoxy]ethoxy, 2-methylsulphonylethoxy, 3-methylsulphonylpropoxy, 2-(4-pyridyloxy)ethoxy, 3-pyridylmethoxy and 2-cyanopyrid-4-ylmethoxy;

$R^2$ is hydrogen; and n is 0 or n is 1 and the $R^3$ group is located at the 6-position of the 2,3-methylenedioxyphenyl group and is selected from chloro and bromo; or a pharmaceutically-acceptable acid-addition salt thereof.

A further preferred compound of the invention is a quinazoline derivative of the Formula I wherein:

m is 2 and the first $R^1$ group is a 6-methoxy group and the second $R^1$ group is located at the 7-position and is selected from 3-(N-isopropyl-N-methylamino)propoxy, 3-pyrrolidin-1-ylpropoxy, 3-morpholinopropoxy, 3-(1,1-dioxotetrahydro-4H-1,4-thiazin-4-yl)propoxy, 3-piperidinopropoxy, N-methylpiperidin-4-ylmethoxy, 2-(4-methylpiperidin-1-yl)ethoxy, 3-(4-methylpiperazin-1-yl)propoxy, 3-(4-cyanomethylpiperazin-1-yl)propoxy and 2-[2-(4-methylpiperazin-1-yl)ethoxy]ethoxy, and wherein any $CH_2$ group within the second $R^1$ group that is attached to two carbon atoms optionally bears a hydroxy group on said $CH_2$ group;

$R^2$ is hydrogen; and n is 0;

or a pharmaceutically-acceptable acid-addition salt thereof.

A particular preferred compound of the invention is, for example, a quinazoline derivative of the Formula I selected from:

6-methoxy-4-(2,3-methylenedioxyanilino)-7-(3-morpholinopropoxy)quinazoline, 6-methoxy-4-(2,3-methylenedioxyanilino)-7-[3-(1,1-dioxotetrahydro-4H-1,4-thiazin-4-yl)propoxy]quinazoline, 6-methoxy-4-(2,3-methylenedioxyanilino)-7-(3-pyrrolidin-1-ylpropoxy)quinazoline, 6-methoxy-4-(2,3-methylenedioxyanilino)-7-[2-(4-methylpiperazin-1-yl)ethoxy]quinazoline, 6-methoxy-4-(2,3-methylenedioxyanilino)-7-[3-(4-methylpiperazin-1-yl)propoxy]quinazoline, 6-methoxy-4-(2,3-methylenedioxyanilino)-7-(3-piperidinopropoxy)quinazoline, 6-methoxy-4-(2,3-methylenedioxyanilino)-7-(N-methylpiperidin-4-ylmethoxy)quinazoline, 7-(2-hydroxy-3-pyrrolidin-1-ylpropoxy)-6-methoxy-4-(2,3-methylenedioxyanilino)-quinazoline, 7-[2-hydroxy-3-(N-isopropyl-N-methylamino)propoxy]-6-methoxy-4-(2,3-methylenedioxyanilino)quinazoline, 7-[3-(4-cyanomethylpiperazin-1-yl)-2-hydroxypropoxy]-6-methoxy-4-(2,3-methylenedioxyanilino)quinazoline and 6-methoxy-4-(2,3-methylenedioxyanilino)-7-{2-[2-(4-methylpiperazin-1-yl)ethoxy]ethoxy}quinazoline;

or a pharmaceutically-acceptable acid-addition salt thereof.

A further particular preferred compound of the invention is, for example, a quinazoline derivative of the Formula I selected from:

4-(6-chloro-2,3-methylenedioxyanilino)-7-[3(4-cyanomethylpiperazin-1-yl)propoxy]-6-methoxyquinazoline, 4-(6-chloro-2,3-methylenedioxyanilino)-6-methoxy-7-(3-pyrrolidin-1-ylpropoxy)quinazoline, 4-(6-chloro-2,3-methylenedioxyanilino)-6-methoxy-7-(3-piperidinopropoxy)quinazoline, 4-(6-bromo-2,3-methylenedioxyanilino)-6-methoxy-7-(3-piperidinopropoxy)quinazoline, 6-methoxy-4-(2,3-methylenedioxyanilino)-7-[2-(N-methylpiperidin-4-yl)ethoxy]quinazoline, 6-methoxy-4-(2,3-methylenedioxyanilino)-7-[2-(4-pyridyloxy)ethoxy]quinazoline, 6-methoxy-4-(2,3-methylenedioxyanilino)-7-(3-pyridylmethoxy)quinazoline, 4-(6-chloro-2,3-methylenedioxyanilino)-7-(2-cyanopyrid-4-ylmethoxy)-6-methoxyquinazoline and 4-(6-chloro-2,3-methylenedioxyanilino)-6-methoxy-7-(N-methylpiperidin-4-ylmethoxy)quinazoline;

or a pharmaceutically-acceptable acid-addition salt thereof.

A quinazoline derivative of the Formula I, or a pharmaceutically-acceptable salt thereof, may be prepared by any process known to be applicable to the preparation of chemically-related compounds. Such processes, when used to prepare a quinazoline derivative of the Formula I are provided as a further feature of the invention and are illustrated by the following representative process variants in which, unless otherwise stated, m, $R^1$, $R^2$, n and $R^3$ have any of the meanings defined herein before. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) The reaction of a quinazoline of the Formula II

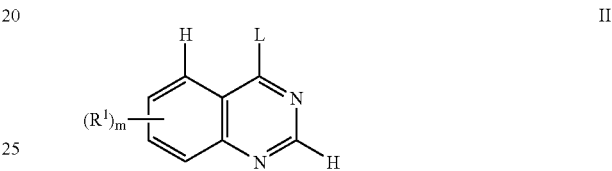

wherein L is a displaceable group and m and $R^1$ have any of the meanings defined hereinbefore except that any functional group is protected if necessary, with an aniline of the Formula III

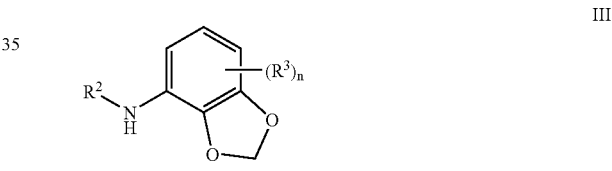

wherein $R^2$, n and $R^3$ have any of the meanings defined hereinbefore except that any functional group is protected if necessary, whereafter any protecting group that is present is removed by conventional means.

The reaction may conveniently be carried out in the presence of a suitable acid or in the presence of a suitable base. A suitable acid is, for example, an inorganic acid such as, for example, hydrogen chloride or hydrogen bromide. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride.

A suitable displaceable group L is, for example, a halogeno, alkoxy, aryloxy or sulphonyloxy group, for example a chloro, bromo, methoxy, phenoxy, pentafluorophenoxy, methanesulphonyloxy or toluene-4-sulphonyloxy group. The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 250° C., preferably in the range 40 to 120° C.

Typically, the quinazoline of the Formula II may be reacted with an aniline of the Formula III in the presence of a protic solvent such as isopropanol, conveniently in the presence of an acid, for example hydrogen chloride gas in diethyl ether, and at a temperature in the range, for example, 25 to 150° C., preferably at or near the reflux temperature of the reaction solvent.

The quinazoline derivative of the Formula I may be obtained from this process in the form of the free base or alternatively it may be obtained in the form of a salt with the acid of the formula H-L wherein L has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2–6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

Quinazoline starting materials of the Formula II may be obtained by conventional procedures. For example, a 3,4-dihydroquinazolin-4-one of Formula IV

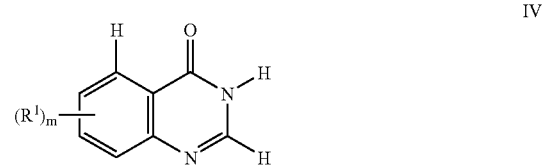

IV wherein m and $R^1$ have any of the meanings defined hereinbefore except that any functional group is protected if necessary, may be reacted with a halogenating agent such as thionyl chloride, phosphoryl chloride or a mixture of carbon tetrachloride and triphenylphosphine whereafter any protecting group that is present is removed by conventional means.

The 4-chloroquinazoline so obtained may be converted, if required, into a 4-pentafluorophenoxyquinazoline by reaction with pentafluorophenol in the presence of a suitable base such as potassium carbonate and in the presence of a suitable solvent such as N,N-dimethylformamide.

2,3-Methylenedioxyaniline starting materials of the Formula III may be obtained by conventional procedures as illustrated in the Examples.

(b) For the production of those compounds of the Formula I wherein at least one $R^1$ group is a group of the formula $Q^1$-$X^1$— wherein $Q^1$ is an aryl-(1–6C)alkyl, (3–7C)cycloalkyl-(1–6C)alkyl, (3–7C)cycloalkenyl-(1–6C)alkyl, heteroaryl-(1–6C)alkyl or heterocyclyl-(1–6C)alkyl group or an optionally substituted alkyl group and $X^1$ is an oxygen atom, the coupling, conveniently in the presence of a suitable dehydrating agent, of a quinazoline of the Formula V

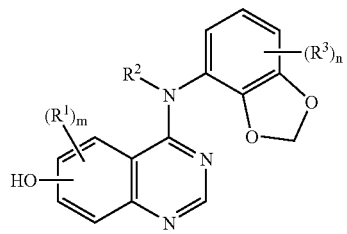

wherein m, $R^1$, $R^2$, n and $R^3$ have any of the meanings defined hereinbefore except that any functional group is protected if necessary, with an appropriate alcohol wherein any functional group is protected if necessary whereafter any protecting group that is present is removed by conventional means.

A suitable dehydrating agent is, for example, a carbodiimide reagent such as dicyclohexylcarbodiimide or 1-(3dimethylaminopropyl)-3-ethylcarbodiimide or a mixture of an azo compound such as diethyl or di-tert-butyl azodicarboxylate and a phosphine such as triphenylphosphine. The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

(c) For the production of those compounds of the Formula I wherein $R^1$ is an amino-substituted (1–6C)alkoxy group (such as 2-homopiperidin-1-ylethoxy or 3-dimethylaminopropoxy), the reaction of a compound of the Formula I wherein $R^1$ is a halogeno-substituted (1–6C)alkoxy group with a heterocyclyl compound or an appropriate amine.

The reaction is conveniently carried out in the presence of a suitable inert diluent or carrier as defined hereinbefore and at a temperature in the range 10 to 150° C., preferably at or near ambient temperature.

(d) For the production of those compounds of the Formula I wherein $R^1$ is a hydroxy group, the cleavage of a quinazoline derivative of the Formula I wherein $R^1$ is a (1–6C)alkoxy or arylmethoxy group.

The cleavage reaction may conveniently be carried out by any of the many procedures known for such a transformation. The cleavage reaction of a compound of the Formula I wherein $R^1$ is a (1–6C)alkoxy group may be carried out, for example, by treatment of the quinazoline derivative with an alkali metal (1–6C)alkylsulphide such as sodium ethanethiolate or, for example, by treatment with an alkali metal diarylphosphide such as lithium diphenylphosphide. Alternatively the cleavage reaction may conveniently be carried out, for example, by treatment of the quinazoline derivative with a boron or aluminium trihalide such as boron tribromide. The cleavage reaction of a compound of the Formula I wherein $R^1$ is a arylmethoxy group may be carried out, for example, by hydrogenation of the quinazoline derivative in the presence of a suitable metallic catalyst such as palladium or by reaction with an organic or inorganic acid, for example trifluoroacetic acid. Such reactions are preferably carried out in the presence of a suitable inert solvent or diluent as defined hereinbefore and at a temperature in the range, for example, 10 to 150° C., preferably at or near ambient temperature.

(e) For the production of those compounds of the Formula I wherein an $R^1$ group contains a primary or secondary amino group, the cleavage of the corresponding compound of the Formula I wherein the $R^1$ group contains a protected primary or secondary amino group.

Suitable protecting groups for an amino group are, for example, any of the protecting groups disclosed hereinbefore for an amino group. Suitable methods for the cleavage of such amino protecting groups are also disclosed hereinbefore. In particular, a suitable protecting group is a lower alkoxycarbonyl group such as a tert-butoxycarbonyl group which may be cleaved under conventional reaction conditions such as under acid-catalysed hydrolysis, for example in the presence of trifluoroacetic acid.

(f) For the production of those compounds of the Formula I wherein an $R^1$ group contains a (1–6C)alkoxy or substituted (1–6C)alkoxy group or a (1–6C)alkylamino or substituted (1–6C)alkylamino group, the alkylation, conveniently in the presence of a suitable base as defined hereinbefore, of a quinazoline derivative of the formula I wherein the $R^1$ group contains a hydroxy group or a primary or secondary amino group as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1–6C)alkyl chloride, bromide or iodide or a substituted (1–6C)alkyl chloride, bromide or iodide, conveniently in the presence of a suitable base as defined hereinbefore, in a suitable inert solvent or diluent as defined hereinbefore and at a temperature in the range, for example, 10 to 140° C., conveniently at or near ambient temperature.

Conveniently for the production of those compounds of the Formula I wherein $R^1$ contains a (1–6C)alkylamino or substituted (1–6C)alkylamino group, a reductive amination reaction may be employed. For example, for the production of those compounds of the Formula I wherein $R^1$ contains a N-methyl group, the corresponding compound containing a N—H group may be reacted with formaldehyde in the presence of a suitable reducing agent. A suitable reducing agent is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is performed at a temperature in the range, for example, 10 to 80° C., conveniently at or near ambient temperature.

(g) For the production of those compounds of the Formula I wherein $R^1$ is an amino-hydroxy-disubstituted (1–6C)

alkoxy group (such as 2-hydroxy-3-pyrrolidin-1-ylpropoxy or 3-[N-allyl-N-methylamino]-2-hydroxypropoxy), the reaction of a compound of the Formula I wherein the $R^1$ group contains an epoxy-substituted (1–6C)alkoxy group with a heterocyclyl compound or an appropriate amine.

The reaction is conveniently carried out in the presence of a suitable inert diluent or carrier as defined hereinbefore and at a temperature in the range 10 to 150° C., preferably at or near ambient temperature.

(h) For the production of those compounds of the Formula I wherein an $R^1$ group contains a hydroxy group, the cleavage of the corresponding compound of the Formula I wherein the $R^1$ group contains a protected hydroxy group.

Suitable protecting groups for a hydroxy group are, for example, any of the protecting groups disclosed hereinbefore. Suitable methods for the cleavage of such hydroxy protecting groups are also disclosed hereinbefore. In particular, a suitable protecting group is a lower alkanoyl group such as an acetyl group which may be cleaved under conventional reaction conditions such as under base-catalysed conditions, for example in the presence of ammonia.

When a pharmaceutically-acceptable salt of a quinazoline derivative of the Formula I is required, for example an acid-addition salt, it may be obtained by, for example, reaction of said quinazoline derivative with a suitable acid using a conventional procedure.

Biological Assays

The following assays can be used to measure the effects of the compounds of the present invention as c-Src tyrosine kinase inhibitors, as inhibitors in vitro of the proliferation of c-Src transfected fibroblast cells, as inhibitors in vitro of the migration of A549 human lung tumour cells and as inhibitors in vivo of the growth in nude mice of xenografts of A549 tissue.

(a) In Vitro Enzyme Assay

The ability of test compounds to inhibit the phosphorylation of a tyrosine containing polypeptide substrate by the enzyme c-Src kinase was assessed using a conventional Elisa assay.

A substrate solution [100 μl of a 20 μg/ml solution of the polyamino acid Poly(Glu, Tyr) 4:1 (Sigma Catalogue No. P0275) in phosphate buffered saline (PBS) containing 0.2 mg/ml of sodium azide] was added to each well of a number of Nunc 96-well immunoplates (Catalogue No. 439454) and the plates were sealed and stored at 4° C. for 16 hours. The excess of substrate solution was discarded, and aliquots of Bovine Serum Albumin (BSA; 150 μl of a 5% solution in PBS) were transferred into each substrate-coated assay well and incubated for 1 hour at ambient temperature to block non specific binding. The assay plate wells were washed in turn with PBS containing 0.05% v/v Tween 20 (PBST) and with Hepes pH7.4 buffer (50 mM, 300 μl/well) before being blotted dry.

Each test compound was dissolved in dimethyl sulphoxide and diluted with distilled water to give a series of dilutions (from 100 μM to 0.001 μM). Portions (25 μl) of each dilution of test compound were transferred to wells in the washed assay plates. "Total" control wells contained diluted DMSO instead of compound. Aliquots (25 μl) of an aqueous magnesium chloride solution (80 mM) containing adenosine-5'-triphosphate (ATP; 40 μM was added to all test wells except the "blank" control wells which contained magnesium chloride without ATP.

Active human c-Src kinase (recombinant enzyme expressed in Sf9 insect cells; obtained from Upstate Biotechnology Inc. product 14-117) was diluted immediately prior to use by a factor of 1:10,000 with an enzyme diluent which comprised 100 mM Hepes pH7.4 buffer, 0.2 mM sodium orthovanadate, 2 mM dithiothreitol and 0.02% BSA. To start the reactions, aliquots (50 μl) of freshly diluted enzyme were added to each well and the plates were incubated at ambient temperature for 20 minutes. The supernatant liquid in each well was discarded and the wells were washed twice with PBST. Mouse IgG anti-phosphotyrosine antibody (Upstate Biotechnology Inc. product 05-321; 100 μl) was diluted by a factor of 1:6000 with PBST containing 0.5% w/v BSA and added to each well. The plates were incubated for 1 hour at ambient temperature. The supernatant liquid was discarded and each well was washed with PBST (×4). Horse radish peroxidase (HRP)-linked sheep anti-mouse Ig antibody (Amersham Catalogue No. NXA 931; 100 μl) was diluted by a factor of 1:500 with PBST containing 0.5% w/v BSA and added to each well. The plates were incubated for 1 hour at ambient temperature. The supernatant liquid was discarded and the wells were washed with PBST (×4).

A PCSB capsule (Sigma Catalogue No. P4922) was dissolved in distilled water (100 ml) to provide phosphate-citrate pH5 buffer (50 mM) containing 0.03% sodium perborate. An aliquot (50 ml) of this buffer was mixed with a 50 mg tablet of 2,2'-azinobis(3-ethylbenzothiazoline-6-sulphonic acid) (ABTS; Boehringer Catalogue No. 1204 521). Aliquots (100 μl) of the resultant solution were added to each well. The plates were incubated for 20 to 60 minutes at ambient temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibition of enzyme activity.

(b) In Vitro c-Src Transfected NIH 3T3 (c-src 3T3) Fibroblast Proliferation Assay This assay determined the ability of a test compound to inhibit the proliferation of National Institute of Health (NIH) mouse 3T3 fibroblast cells that had been stably-transfected with an activating mutant (Y530F) of human c-Src.

Using a similar procedure to that described by Shalloway et al., Cell, 1987, 49, 65–73, NIH 3T3 cells were transfected with an activating mutant (Y530F) of human c-Src. The resultant c-Src 3T3 cells were typically seeded at $1.5 \times 10^4$ cells per well into 96-well tissue-culture-treated clear assay plates (Costar) each containing an assay medium comprising Dulbecco's modified Eagle's medium (DMEM; Sigma) plus 0.5% foetal calf serum (FCS), 2 mM glutamine, 100 units/ml penicillin and 0.1 mg/ml streptomycin in 0.9% aqueous sodium chloride solution. The plates were incubated overnight at 37° C. in a humidified (7.5% $CO_2$: 95% air) incubator.

Test compounds were solubilised in DMSO to form a 10 mM stock solution. Aliquots of the stock solution were diluted with the DMEM medium described above and added to appropriate wells. Serial dilutions were made to give a range of test concentrations. Control wells to which test compound was not added were included on each plate. The plates were incubated overnight at 37° C. in a humidified (7.5% $CO_2$:95% air) incubator.

BrdU labelling reagent (Boehringer Mannheim Catalogue No. 647 229) was diluted by a factor of 1:100 in DMEM medium containing 0.5% FCS and aliquots (20 μl) were added to each well to give a final concentration of 10 μM). The plates were incubated at 37° C. for 2 hours. The medium was decanted. A denaturing solution (FixDenat solution, Boehringer Mannheim Catalogue No. 647 229; 50 μl) was added to each well and the plates were placed on a plate shaker at ambient temperature for 45 minutes. The supernatant was decanted and the wells were washed with PBS (200 μl per well). Anti-BrdU-Peroxidase solution (Boehringer Mannheim Catalogue No. 647 229) was diluted by a factor of 1:100 in PBS containing 1% BSA and 0.025% dried skimmed milk (Marvel (registered trade mark), Premier Beverages, Stafford, GB) and an aliquot (100 μl) of the resultant solution was added to each well. The plates were placed on a plate shaker at ambient temperature for 90 minutes. The wells were washed with PBS (×5) to ensure removal of non bound antibody conjugate. The plates were blotted dry and tetramethylbenzidine substrate solution (Boehringer Mannheim Catalogue No. 647 229; 100 μl) was added to each well. The plates were gently agitated on a plate shaker while the colour developed during a 10 to 20 minute period. The absorbance of the wells was measured at 690 nm. The extent of inhibition of cellular proliferation at a range of concentrations of each test compound was determined and an anti-proliferative $IC_{50}$ value was derived.

(c) In Vitro Microdroplet Migration Assay

This assay determines the ability of a test compound to inhibit the migration of adherent mammalian cell lines, for example the human tumour cell line A549.

RPMI medium(Sigma) containing 10% FCS, 1% L-glutanine and 0.3% agarose (Difco Catalogue No. 0142-01) was warmed to 37° C. in a water bath. A stock 2% aqueous agar solution was autoclaved and stored at 42° C. An aliquot (1.5 ml) of the agar solution was added to RPMI medium (10 ml) immediately prior to its use. A549 cells (Accession No. ATCC CCL185) were suspended at a concentration of $2×10^7$ cells/ml in the medium and maintained at a temperature of 37° C.

A droplet (2 μl) of the cell/agarose mixture was transferred by pipette into the centre of each well of a number of 96-well, flat bottomed non-tissue-culture-treated microtitre plate (Bibby Sterilin Catalogue No. 642000). The plates were placed briefly on ice to speed the gelling of the agarose-containing droplets. Aliquots (90 μl) of medium which had been cooled to 4° C. were transferred into each well, taking care not to disturb the microdroplets. Test compounds were diluted from a 10 mM stock solution in DMSO using RPMI medium as described above. Aliquots (10 μl) of the diluted test compounds were transferred to the wells, again taking care not to disturb the microdroplets. The plates were incubated at 37° C. in a humidified (7.5% $CO_2$:95% air) incubator for about 48 hours.

Migration was assessed visually and the distance of migration was measured back to the edge of the agar droplet. A migratory inhibitory $IC_{50}$ was derived by plotting the mean migration measurement against test compound concentration.

(d) In Vivo A549 Xenograft Growth Assay

This test measures the ability of compounds to inhibit the growth of the A549 human carcinoma grown as a tumour in athymic nude mice (Alderley Park nu/nu strain). A total of about $5×10^6$ A549 cells in matrigel (Beckton Dickinson Catalogue No. 40234) were injected subcutaneously into the left flank of each test mouse and the resultant tumours were allowed to grow for about 14 days. Tumour size was measured twice weekly using callipers and a theoretical volume was calculated. Animals were selected to provide control and treatment groups of approximately equal average tumour volume. Test compounds were prepared as a ball-milled suspension in 1% polysorbate vehicle and dosed orally once daily for a period of about 28 days. The effect on tumour growth was assessed.

Although the pharmacological properties of the compounds of the Formula I vary with structural change as expected, in general activity possessed by compounds of the Formula I, may be demonstrated at the following concentrations or doses in one or more of the above tests (a), (b), (c) and (d):

| | |
|---|---|
| Test (a):- | $IC_{50}$ in the range, for example, 0.001–10 μM; |
| Test (b):- | $IC_{50}$ in the range, for example, 0.01–20 μM; |
| Test (c):- | activity in the range, for example, 0.01–25 μM; |
| Test (d):- | activity in the range, for example, 1–200 mg/kg/day;. |

No physiologically-unacceptable toxicity was observed in Test (d) at the effective dose for compounds tested of the present invention. Accordingly no untoward toxicological effects are expected when a compound of Formula I, or a pharmaceutically-acceptable salt thereof, as defined hereinbefore is administered at the dosage ranges defined hereinafter.

According to a further aspect of the invention there is provided a pharmaceutical composition which comprises a quinazoline derivative of the Formula I, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

According to a further aspect of the invention there is provided a quinazoline derivative of the Formula I, or a pharmaceutically-acceptable salt thereof, as defined hereinbefore for use in a method of treatment of the human or animal body by therapy.

As stated above, it is known that the predominant role of c-Src non-receptor tyrosine kinase is to regulate cell motility which is necessarily required for a localised tumour to progress through the stages of dissemination into the blood stream, invasion of other tissues and initiation of metastatic tumour growth. We have found that the quinazoline derivatives of the present invention possess potent anti-tumour activity which it is believed is obtained by way of inhibition of one or more of the non-receptor tyrosine-specific protein kinases such as c-Src kinase that are involved in the signal transduction steps which lead to the invasiveness and migratory ability of metastasising tumour cells.

Accordingly the quinazoline derivatives of the present invention are of value as anti-tumour agents, in particular as selective inhibitors of the motility, dissemination and invasiveness of mammalian cancer cells leading to inhibition of metastatic tumour growth. Particularly, the quinazoline derivatives of the present invention are of value as anti-invasive agents in the containment and/or treatment of solid tumour disease. Particularly, the compounds of the present invention are expected to be useful in the prevention or treatment of those tumours which are sensitive to inhibition of one or more of the multiple non-receptor tyrosine kinases such as c-Src kinase that are involved in the signal transduction steps which lead to the invasiveness and migratory ability of metastasising tumour cells. Further, the compounds of the present invention are expected to be useful in the prevention or treatment of those tumours which are mediated alone or in part by inhibition of the enzyme c-Src, i.e. the compounds may be used to produce a c-Src enzyme inhibitory effect in a warm-blooded animal in need of such treatment. Specifically, the compounds of the present invention are expected to be useful in the prevention or treatment of solid tumour disease.

Thus according to this aspect of the invention there is provided the use of a quinazoline derivative of the Formula I, or a pharmaceutically-acceptable salt thereof, as defined hereinbefore in the manufacture of a medicament for use as an anti-invasive agent in the containment and/or treatment of solid tumour disease.

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a quinazoline derivative of the Formula I, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in the prevention or treatment of solid tumour disease in a warm-blooded animal such as man.

According to a further feature of this aspect of the invention there is provided a method for the prevention or treatment of solid tumour disease in a warm-blooded animal, such as man, in need of such treatment which comprises administering to said animal an effective amount of a quinazoline derivative of the Formula I, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in the prevention or treatment of those tumours which are sensitive to inhibition of non-receptor tyrosine kinases such as c-Src kinase that are involved in the signal transduction steps which lead to the invasiveness and migratory ability of metastasising tumour cells.

According to a further feature of this aspect of the invention there is provided a method for the prevention or treatment of those tumours which are sensitive to inhibition of non-receptor tyrosine kinases such as c-Src kinase that are involved in the signal transduction steps which lead to the invasiveness and migratory ability of metastasising tumour cells which comprises administering to said animal an effective amount of a quinazoline derivative of the Formula I, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in providing a c-Src kinase inhibitory effect.

According to a further feature of this aspect of the invention there is provided a method for providing a c-Src kinase inhibitory effect which comprises administering to said animal an effective amount of a quinazoline derivative of the Formula I, or a pharmaceutically-acceptable salt thereof, as defined hereinbefore.

The anti-invasive treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:

(i) other anti-invasion agents (for example metalloproteinase inhibitors like marimastat and inhibitors of urokinase plasminogen activator receptor function);

(ii) antiproliferative/antineoplastic drugs and combinations thereof, as used in medical oncology, such as alkylating agents (for example cis-platin, carboplatin, cyclophospharide, nitrogen mustard, melphalan, chlorambucil, busulphan and nitrosoureas); antimetabolites (for example antifolates such as fluoropyrnmidines like 5-fluorouracil and tegafur, raltitrexed, methotrexate, cytosine arabinoside and hydroxyurea, or, for example, one of the preferred antimetabolites disclosed in European Patent Application No. 562734 such as (2S)-2-{o-fluoro-p-[N-{2,7-dimethyl-4-oxo-3,4-dihydroquinazolin-6-ylmethyl)-N-(prop-2-ynyl)amino]benzamido}-4-(tetrazol-5-yl)butyric acid); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(iii) cytostatic agents such as antioestrogens (for example tamoxifen, toremifene, raloxifene, droloxifene and iodoxyfene), antiandrogens (for example bicalutamide, flutamide, nilutamide and cyproterone acetate), LHRH antagonists or LHR agonists (for example goserelin, leuprorelin and buserelin), progestogens (for example megestrol acetate), aromatase inhibitors (for example as anastrozole, letrazole, vorazole and exemestane) and inhibitors of 5α-reductase such as finasteride;

(iv) inhibitors of growth factor function, for example such inhibitors include growth factor antibodies, growth factor receptor antibodies, tyrosine kinase inhibitors and serine/threonine kinase inhibitors, for example inhibitors of the epidermal growth factor family (for example the EGFR tyrosine kinase inhibitors N-(3-chloro-4-fluorophenyl)-7-methoxy-6-(3-morpholinopropoxy)quinazolin-4-amine (ZD1839), N-(3-ethynylphenyl)-6,7-bis(2-methoxyethoxy)quinazolin-4-amine (CP 358774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family; and (v) antiangiogenic agents such as those which inhibit vascular endothelial growth factor such as the compounds disclosed in International Patent Applications WO 97/22596, WO 97/30035, WO 97/32856 and WO 98/13354 and those that work by other mechanisms (for example linomide, inhibitors of integrin αvβ3 function and angiostatin).

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinazoline derivative of the formula I as defined hereinbefore and an additional anti-tumour agent as defined hereinbefore for the conjoint treatment of cancer.

Although the compounds of the Formula I are primarily of value as therapeutic agents for use in warm-blooded animals (including man), they are also useful whenever it is required to inhibit the effects of c-Src. Thus, they are useful as pharmacological standards for use in the development of new biological tests and in the search for new pharmacological agents.

The invention will now be illustrated in the following Examples in which, generally:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields, where present, are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Jeol JNM EX 400 spectrometer operating at a field strength of 400 MHz, Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; q, quartet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture;

(viii) the following abbreviations have been used:

| DMF | N,N-dimethylformamide |
| DMSO | dimethylsulphoxide |
| THF | tetrahydrofuran |

EXAMPLE 1

6-methoxy-4-(2,3-methylenedioxyanilino)-7-(3-morpholinopropoxy)quinazoline

A mixture of 4-chloro-6-methoxy-7-(3-morpholinopropoxy)quinazoline (0.1 g), 2,3-methylenedioxyaniline (0.048 g), pentan-2-ol (5 ml) and a solution of hydrogen chloride in isopropanol (6M, 4 drops) was stirred and heated to 100° C. for 5 hours. The resultant mixture was cooled to ambient temperature and the precipitate was isolated by filtration, washed with pentan-2-ol and dried under vacuum. There was thus obtained the title compound (0.138 g) as a dihydrochloride salt; NMR Spectrum: (DMSOd$_6$ and CF$_3$COOD) 2.35 (m, 2H), 2.5 (m, 2H), 3.15 (m, 2H), 3.3 (m, 2H), 3.55 (d, 2H), 3.8 (t, 2H), 4.05 (s, 3H), 4.35 (t, 2H), 6.1 (s, 2H), 7.0 (m, 3H), 7.4 (s, 1H), 8.2 (s, 1H), 8.85 (s, 1H); Mass Spectrum: M+H$^+$ 439; Elemental Analysis: Found C, 52.8; H, 5.56; N, 10.68. C$_{23}$H$_{26}$N$_4$O$_5$ 2HCl 0.5H$_2$O requires C, 53.08; H, 5.62; N, 10.77%.

The 4-chloro-6-methoxy-7-(3-morpholinopropoxy) quinazoline used as a starting material was prepared as follows:

A mixture of 2-amino-4-benzyloxy-5-methoxybenzamide (J. Med. Chem., 1977, 20, 146–149; 10 g), (3-dimethylamino-2-azaprop-2-en-1-ylidene)dimethylammonium chloride (Gold's reagent, 7.4 g) and dioxane (100 ml) was stirred and heated to reflux for 24 hours. Sodium acetate (3.02 g) and acetic acid (1.65 ml) were added and the reaction mixture was heated for a further 3 hours. The mixture was evaporated and water was added to the residue. The resultant solid was collected by filtration, washed with water and dried. The material was recrystallised from acetic acid to give 7-benzyloxy-6-methoxy-3,4-dihydroquinazolin4-one (8.7 g).

After repetition of the reaction so described, a mixture of 7-benzyloxy-6-methoxy-3,4-dihydroquinazolin-4-one (35 g), thionyl chloride (440 ml) and DMF (1.75 ml) was heated to reflux for 4 hours. The thionyl chloride was evaporated under vacuum and the residue was azeotroped with toluene three times. The residue was dissolved in N-methylpyrrolidin-2-one (250 ml) to give a solution of 7-benzyloxy-4-chloro-6-methoxyquinazoline.

Phenol (29.05 g) was dissolved in N-methylpyrrolidin-2-one (210 ml) and sodium hydride (60% dispersion in mineral oil; 11.025 g) was added in portions with cooling. The resultant mixture was stirred at ambient temperature for 3 hours. The resultant viscous suspension was diluted with N-methylpyrrolidin-2-one (180 ml) and stirred overnight. The above-mentioned solution of 7-benzyloxy-4-chloro-6-methoxyquinazoline was added and the resultant suspension was stirred and heated to 100° C. for 2.5 hours. The mixture was allowed to cool to ambient temperature and poured into water (1.5 L) with vigorous stirring. The precipitate was collected by filtration, washed with water and dried under vacuum. The material so obtained was dissolved in methylene chloride and the solution was washed with brine and filtered through phase separating paper. The solution was evaporated under vacuum and the resultant residue was triturated under diethyl ether. There was thus obtained 7-benzyloxy-6-methoxy-4phenoxyquinazoline (87.8 g); NMR Spectrum: (CDCl$_3$) 4.09 (s, 3H), 5.34 (s, 2H), 7.42 (m, 12H), 7.63 (s, 1H).

A mixture of a portion (36.95 g) of the material so obtained and trifluoroacetic acid (420 ml) was heated to reflux for 3 hours. The reaction mixture was allowed to cool and evaporated under vacuum. The residue was stirred mechanically under water, basified by the addition of a saturated aqueous sodium bicarbonate solution and stirred overnight. The water was decanted and the residual solid was suspended in acetone. After stirring, the white solid was collected by filtration, washed with acetone and dried to give 7-hydroxy-6-methoxy-4-phenoxyquinazoline (26.61 g); NMR Spectrum: (DMSOd$_6$) 3.97 (s, 3H), 7.22 (s, 1H), 7.3 (m, 3H), 7.47 (t, 2H), 7.56 (s, 1H), 8.47 (s, 1H), 10.7 (s, 1H).

A mixture of 7-hydroxy-6-methoxy-4-phenoxyquinazoline (25.27 g), 3-morpholinopropyl chloride (18.48 g), potassium carbonate (39.1 g) and DMF (750 ml) was stirred and heated to 90° C. for 3 hours. The mixture was allowed to cool to ambient temperature and filtered. The filtrate was evaporated and the residue was triturated under ethyl acetate. There was thus obtained 6-methoxy-7-(3-morpholinopropoxy)-4-phenoxyquinazoline (31.4 g); NMR Spectrum: (DMSOd$_6$) 1.97 (m, 2H), 2.39 (t, 4H), 2.47 (t, 2H), 3.58 (t, 4H), 3.95 (s, 3H), 4.23 (t, 2H), 7.31 (m, 3H), 7.36 (s, 1H), 7.49 (t, 2H), 7.55 (s, 1H), 8.52 (s, 1H).

A mixture of the material so obtained and 6N aqueous hydrochloric acid solution (800 ml) was stirred and heated to reflux for 1.5 hours. The reaction mixture was decanted and concentrated to a volume of 250 ml. The mixture was basified to pH9 by the addition of a saturated aqueous sodium bicarbonate solution and extracted with methylene chloride (4×400 ml). The combined extracts were filtered through phase separating paper and the filtrate was evaporated. The resultant solid was triturated under ethyl acetate to give 6-methoxy-7-(3-morpholinopropoxy)-3,4-dihydroquinazolin-4-one (23.9 g); NMR Spectrum: (DMSOd$_6$) 1.91 (m, 2H), 2.34 (t, 4H), 2.42 (t, 2H), 3.56 (t, 4H), 3.85 (s, 3H), 4.12 (t, 2H), 7.11 (s, 1H), 7.42 (s, 1H), 7.96 (s, 1H), 12.01 (s, 1H).

A mixture of the material so obtained, thionyl chloride (210 ml) and DMF (1.8 ml) was heated to reflux for 1.5 hours. The thionyl chloride was removed by evaporation under vacuum and the residue was azeotroped with toluene three times. The residue was taken up in water and basified to pH8 by the addition of a saturated aqueous sodium bicarbonate solution. The resultant aqueous layer was extracted with methylene chloride (4×400 ml). The combined extracts were washed with water and with brine and dried over magnesium sulphate. The solution was filtered and evaporated. The resultant solid was triturated under ethyl acetate to give 4-chloro-6-methoxy-7-(3-morpholinopropoxy)quinazoline (17.39 g); NMR Spectrum: (CDCl$_3$) 2.1–2.16 (m, 2H), 2.48 (br s, 4H), 2.57 (t, 2H), 3.73 (t, 4H), 4.05 (s, 3H), 4.29 (t, 2H), 7.36 (s, 1H), 7.39 (s, 1H), 8.86 (s, 1H).

The 3-morpholinopropyl chloride used as a reagent was obtained as follows:

A mixture of morpholine (52.2 ml), 1-bromo-3-chloropropane (30 ml) and toluene (180 ml) was heated to 70° C. for 3 hours. The solid was removed by filtration and the filtrate was evaporated under vacuum. The resultant oil was decanted from the additional solid which was deposited and the oil was purified by vacuum distillation to yield 3-morpholinopropyl chloride (37.91 g); NMR Spectrum: (DMSOd$_6$) 1.85 (m, 2H), 2.3 (t, 4H), 2.38 (t, 2H), 3.53 (t, 4H), 3.65 (t, 2H).

The 2,3-methylenedioxyaniline used as a starting material was prepared as follows:

A mixture of 2,3-dihydroxybenzoic acid (5 g), methanol (50 ml) and concentrated sulphuric acid (10 drops) was stirred and heated to 60° C. for 24 hours. The mixture was evaporated and the residue was taken up in ethyl acetate. The organic solution was washed with a saturated solution of sodium bicarbonate, dried over magnesium sulphate and evaporated to give methyl 2,3-dihydroxybenzoate (2.19 g); NMR Spectrum: (CDCl$_3$) 3.95 (s, 3H), 5.7 (s, 1H), 6.8 (t, 1H), 7.15 (d, 1H), 7.35 (d, H).

After repetition of the previous reaction, a mixture of methyl 2,3-dihydroxybenzoate (2.8 g), potassium fluoride (4.8 g) and DMF (45 ml) was stirred at ambient temperature for 30 minutes. Dibromomethane (1.28 ml) was added and the mixture was heated to 120° C. for 3 hours. The mixture was cooled to ambient temperature, poured into water and extracted with diethyl ether. The organic phase was washed with water and with brine, dried over magnesium sulphate and evaporated. The residue was purified by column chromatography using a 9:1 mixture of petroleum ether (b.p. 40–60° C.) and ethyl acetate as eluent. There was thus obtained methyl 2,3-methylenedioxybenzoate (2.3 g) as a solid; NMR Spectrum: (CDCl$_3$) 3.95 (s, 3H), 6.1 (s, 2H), 6.85 (t, 1H), 7.0 (d, 1H), 7.45 (d, 1H).

A mixture of the material so obtained, a 2N aqueous potassium hydroxide solution (15.5 ml) and methanol (40 ml) was stirred at ambient temperature for 2 hours. The solution was concentrated to about one quarter of the original volume and cooled in an ice bath. The mixture was acidified to pH 3.5 by the addition of a 2N aqueous hydrochloric acid solution. The resultant precipitate was collected by filtration and washed in turn with water and diethyl ether. There was thus obtained 2,3-methylenedioxybenzoic acid (1.87 g); NMR Spectrum: (DMSOd$_6$) 6.1 (s, 1H), 6.9 (t, 1H), 7.15 (d, 1H), 7.3 (d, 1H), 13.0 (br s, 1H).

The material so obtained was suspended in anhydrous dioxane (30 ml) and anhydrous diphenylphosphoryl azide (2.45 ml), triethylamine (1.6 ml) and tert-butanol (9 ml) were added. The mixture was heated to reflux for 5 hours. The mixture was cooled to ambient temperature, concentrated by evaporation and diluted with ethyl acetate. The organic phase was washed in turn with a 5% aqueous citric acid solution, water, an aqueous sodium bicarbonate solution and brine and dried over magnesium sulphate. The solvent was evaporated and the residue was purified by column chromatography on silica using a 19:1 mixture of petroleum ether (b.p. 40–60° C.) and ethyl acetate as eluent. There was thus obtained tert-butyl 2,3-methylenedioxyphenylcarbamate (1.98 g) as a solid; NMR Spectrum: (CDCl$_3$) 1.55 (s, 9H), 5.95 (s, 2H), 6.4 (br s, 1H), 6.55 (d, 1H), 6.8 (t, 1H), 7.45 (d, 1H).

A 5N aqueous hydrochloric acid solution (30 ml) was added to a solution of tert-butyl 2,3-methylenedioxyphenylcarbamate (1.9 g) in ethanol (38 ml) and the reaction mixture was stirred at ambient temperature for 20 hours. The ethanol was evaporated and the residual aqueous phase was washed with diethyl ether and neutralised to pH7 by the addition of solid potassium hydroxide. The resultant mixture was filtered and the aqueous phase was extracted with diethyl ether. The organic phase was washed with brine, dried over magnesium sulphate and evaporated. There was thus obtained 2,3-methylenedioxyaniline (1.0 g) as an oil; NMR Spectrum: (CDCl$_3$) 3.0 (br s, 2H), 5.9 (s, 2H), 6.3 (m, 2H), 7.25 (t, 1H).

EXAMPLE 2

Using an analogous procedure to that described in Example 1, the appropriate 4-chloroquinazoline was reacted with the appropriate 2,3-methylenedioxyaniline to give the compounds described in Table I. Unless otherwise stated, each compound described in Table I was obtained as a dihydrochloride salt.

TABLE I

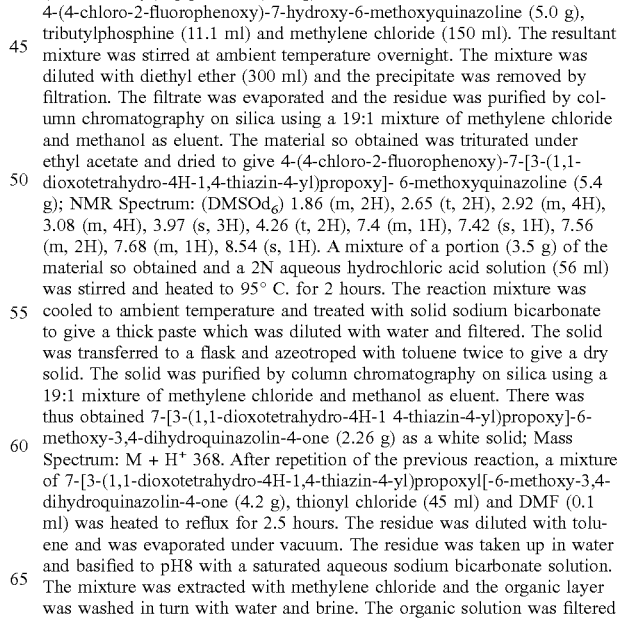

| Compound No. & Note | R$^1$ | R$^2$ |
|---|---|---|
| [1] | 3-(1,1-dioxotetrahydro-4H-1,4-thiazin-4-yl)propoxy | hydrogen |
| [2] | 3-pyrrolidin-1-ylpropoxy | hydrogen |
| [3] | 3-(4-methylpiperazin-1-yl)propoxy | hydrogen |
| [4] | 3-piperidinopropoxy | hydrogen |
| [5] | N-methylpiperidin-4-ylmethoxy | hydrogen |
| [6] | 2-[2-(4-methylpiperazin-1-yl)ethoxy]ethoxy | hydrogen |
| [7] | methoxy | hydrogen |
| [8] | benzyloxy | hydrogen |
| [9] | 3-pyrrolidin-1-ylpropoxy | 6-chloro |
| [10] | 3-morpholinopropoxy | 6-chloro |
| [11] | 3-(4-methylpiperazin-1-yl)propoxy | 6-chloro |
| [12] | N-methylpiperidin-4-ylmethoxy | 6-chloro |
| [13] | benzyloxy | 6-chloro |

TABLE I-continued

| [14] | 3-morpholinopropoxy | 6-bromo |
| [15] | 3-methylsulphonylpropoxy | 6-bromo |
| [16] | 3-morpholinopropoxy | 5-methoxy |
| [17] | 2-acetoxy-3-morpholinopropoxy | hydrogen |
| [18] | 2-acetoxy-3-pyrrolidin-1-ylpropoxy | hydrogen |
| [19] | 2-acetoxy-3-piperidinopropoxy | hydrogen |
| [20] | 2-acetoxy-3-(4-cyanomethylpiperazin-1-yl)propoxy | hydrogen |
| [21] | 2-acetoxy-3-(N-isopropyl-N-methylamino)propoxy | hydrogen |
| [22] | 3-(4-methylpiperazin-1-yl)propoxy | 5-methoxy |
| [23] | 2-(N-methylpiperidin-4-yl)ethoxy | hydrogen |
| [24] | piperidin-4-ylmethoxy | hydrogen |
| [25] | 2-piperidin-4-ylethoxy | hydrogen |
| [26] | N-(2-morpholinoethyl)piperidin-4-ylmethoxy | hydrogen |

Notes

[1] The product gave the following characterising data; NMR Spectrum: (DMSOd$_6$ and CF$_3$COOD) 2.35 (m, 2H), 3.45 (t, 2H), 3.75 (br s, 4H), 3.85 (br s, 4H), 4.05 (s, 3H), 4.35 (t, 2H), 6.1 (s, 2H), 7.0 (m, 3H), 7.4 (s, 1H), 8.2 (s, 1H), 8.9 (s, 1H); Mass Spectrum: M + H$^+$ 487. The 4-chloro-7-[3-(1,1-dioxotetrahydro-4H-1,4-thiazin-4-yl)propoxy]-6-methoxyquinazoline used as a starting material was prepared as follows:-

A mixture of 7-benzyloxy-6-methoxy-3,4-dihydroquinazolin-4-one (20.3 g), thionyl chloride (440 ml) and DMF (1.75 ml) was heated to reflux for 4 hours. The thionyl chloride was evaporated under vacuum and the residue was azeotroped with toluene three times to give 7-benzyloxy-4-chloro-6-methoxyquinazoline. A mixture of the 7-benzyloxy-4-chloro-6-methoxyquinazoline so obtained, potassium carbonate (50 g) and 4-chloro-2-fluorophenol (8.8 ml) and DMF (500 ml) was stirred and heated to 100° C. for 5 hours. The mixture was allowed to cool to ambient temperature, poured into water (2 L) and stirred at ambient temperature for a few minutes. The resultant solid was isolated and washed with water. The solid was dissolved in methylene chloride and the solution was filtered and treated with decolourising charcoal. The resultant solution was filtered and evaporated to give a solid which was triturated under diethyl ether. There was thus obtained 7-benzyloxy-4-(4-chloro-2-fluorophenoxy)-6-methoxyquinazoline (23.2 g); NMR Spectrum: (DMSOd$_6$) 3.98 (s, 3H), 5.34 (s, 2H), 7.42 (m, 9H), 7.69 (m, 1H), 8.55 (s, 1H). A mixture of the material so obtained and trifluoroacetic acid (15 ml) was heated to reflux for 3 hours. The reaction mixture was allowed to cool, toluene was added and the mixture was evaporated. The residue was triturated under diethyl ether and then under acetone. The resultant precipitate was isolated and dried to give 4-(4-chloro-2-fluorophenoxy)-7-hydroxy-6-methoxyquinazoline trifluoroacetate salt (21.8 g) which was used without further purification.

3-(1,1-Dioxotetrahydro-4H-1,4-thiazin-4-yl)propan-1-ol (4.2 g) and 1,1'-(azodicarbonyl)dipiperidine (11.7 g) were added in turn to a mixture of 4-(4-chloro-2-fluorophenoxy)-7-hydroxy-6-methoxyquinazoline (5.0 g), tributylphosphine (11.1 ml) and methylene chloride (150 ml). The resultant mixture was stirred at ambient temperature overnight. The mixture was diluted with diethyl ether (300 ml) and the precipitate was removed by filtration. The filtrate was evaporated and the residue was purified by column chromatography on silica using a 19:1 mixture of methylene chloride and methanol as eluent. The material so obtained was triturated under ethyl acetate and dried to give 4-(4-chloro-2-fluorophenoxy)-7-[3-(1,1-dioxotetrahydro-4H-1,4-thiazin-4-yl)propoxy]- 6-methoxyquinazoline (5.4 g); NMR Spectrum: (DMSOd$_6$) 1.86 (m, 2H), 2.65 (t, 2H), 2.92 (m, 4H), 3.08 (m, 4H), 3.97 (s, 3H), 4.26 (t, 2H), 7.4 (m, 1H), 7.42 (s, 1H), 7.56 (m, 2H), 7.68 (m, 1H), 8.54 (s, 1H). A mixture of a portion (3.5 g) of the material so obtained and a 2N aqueous hydrochloric acid solution (56 ml) was stirred and heated to 95° C. for 2 hours. The reaction mixture was cooled to ambient temperature and treated with solid sodium bicarbonate to give a thick paste which was diluted with water and filtered. The solid was transferred to a flask and azeotroped with toluene twice to give a dry solid. The solid was purified by column chromatography on silica using a 19:1 mixture of methylene chloride and methanol as eluent. There was thus obtained 7-[3-(1,1-dioxotetrahydro-4H-1 4-thiazin-4-yl)propoxy]-6-methoxy-3,4-dihydroquinazolin-4-one (2.26 g) as a white solid; Mass Spectrum: M + H$^+$ 368. After repetition of the previous reaction, a mixture of 7-[3-(1,1-dioxotetrahydro-4H-1,4-thiazin-4-yl)propoxyl[-6-methoxy-3,4-dihydroquinazolin-4-one (4.2 g), thionyl chloride (45 ml) and DMF (0.1 ml) was heated to reflux for 2.5 hours. The residue was diluted with toluene and was evaporated under vacuum. The residue was taken up in water and basified to pH8 with a saturated aqueous sodium bicarbonate solution. The mixture was extracted with methylene chloride and the organic layer was washed in turn with water and brine. The organic solution was filtered

TABLE I-continued through phase separating paper and evaporated to give an orange solid which was purified by column chromatography on silica using a 19:1 mixture of methylene chloride and methanol as eluent. The resultant solid was triturated under diethyl ether and dried to give 4-chloro-7-[3-(1,1-dioxotetrahydro-4H-1,4-thiazin-4-yl)propoxy]-6-methoxyquinazoline (2.27 g); Mass Spectrum: M + H⁺ 386. The 3-(1,1-dioxotetrahydro-4H- 1,4-thiazin-4-yl)propan-1-ol used as an intermediate was obtained as follows:-
A mixture of 3-aminopropan-1-ol (0.65 ml) and divinyl sulphone (1 g) was heated to 110° C. for 45 minutes. The mixture was allowed to cool to ambient temperature and was purified by column chromatography on silica using a 19:1 mixture of methylene chloride and methanol as eluent. There was thus obtained 3-(1,1-dioxotetrahydro-4H-1,4-thiazin-4-yl)propan-1-ol (0.8 g); NMR Spectrum: (CDCl₃) 1.7–1.8 (m, 2H), 2.73 (t, 2H), 3.06 (br s, 8H), 3.25 (s, 1H), 3.78 (t, 2H); Mass Spectrum: M + H⁺ 194.

[2] The product gave the following characterising data; NMR Spectrum: (DMSOd₆ and CF₃COOD) 1.8 (m, 2H), 2.05 (m, 2H), 2.3 (m, 2H), 3.05 (m, 2H), 3.35 (t, 2H), 3.6 (m, 2H), 4.0 (s, 3H), 4.3 (t, 2H), 6.1 (s, 2H), 6.95 (m, 3H), 7.4 (s, 1H), 8.2 (s, 1H), 8.85 (s, 1H); Mass Spectrum: M + H⁺ 423. The 4-chloro-7-(3-pyrrolidin-1-ylpropoxy)-6-methoxyquinazoline used as a starting material was prepared as follows:-
A mixture of 4-hydroxy-3-methoxybenzoic acid (8.4 g), 3-(pyrrolidin-1-yl)propyl chloride (J. Amer. Chem. Soc., 1955, 77, 2272; 14.75 g), potassium carbonate (13.8 g), potassium iodide (1.66 g) and DMF (150 ml) was stirred and heated to 100° C. for 3 hours. The mixture was allowed to cool to ambient temperature, filtered and the filtrate was evaporated. The residue was dissolved in ethanol (75 ml), 2N aqueous sodium hydroxide solution (75 ml) was added and the mixture was heated to 90° C. for 2 hours. The mixture was concentrated by evaporation and acidified by the addition of concentrated aqueous hydrochloric acid. The resultant mixture was washed with diethyl ether and then purified by column chromatography using a Diaion (trade mark of Mitsubishi) HP20SS resin column, eluting with water and then with a gradient of methanol (0 to 25%) in dilute hydrochloric acid (pH2.2). The methanol was removed by evaporation and the aqueous residue was freeze dried to give 3-methoxy-4-(3- pyrrolidin-1-ylpropoxy)benzoic acid hydrochloride (12.2 g); NMR Spectrum: (DMSOd₆ and CF₃CO₂D) 2.2 (m, 2H), 3.15 (t, 2H), 3.3 (t,2H), 3.5 (d, 2H), 3.7 (t, 2H), 3.82 (s, 3H), 4.05 (d, 2H), 4.15 (t, 2H), 7.07 (d, 1H), 7.48 (s, 1H), 7.59 (d, 1H). The material so obtained was dissolved in trifluoroacetic acid (40 ml) and the solution was cooled to 0° C.. Fuming nitric acid (2.4 ml) was added slowly. The cooling bath was removed and the reaction mixture was stirred at ambient temperature for 1 hour. The mixture was evaporated and a mixture of ice and water was added to the residue. The mixture was evaporated. The solid residue was dissolved in dilute hydrochloric acid (pH2.2) and purified by column chromatography using a Diaion HP20SS resin column using a gradient of methanol (0 to 50%) in water. Concentration of the fractions by evaporation gave a precipitate which was collected and dried under vacuum over phosphorus pentoxide. There was thus obtained 5-methoxy-2- nitro-4-(3-pyrroridin-1-ylpropoxy)benzoic acid hydrochloride (12.1 g, 90%); NMR Spectrum: (DMSOd₆ and CF₃CO₂D) 1.8–1.9 (m, 2H), 2.0–2.1 (m, 2H), 2.1–2.2 (m, 2H), 3.0–3.1 (m, 2H), 3.3 (t, 2H), 3.6–3.7 (m, 2H), 3.95 (m, 3H), 4.25 (t, 2H), 7.35 (s, 1H), 7.62 (s, 1H). A mixture of a portion (9.63 g) of the material so obtained, thionyl chloride (20 ml) and DMF (0.05 ml) was heated to 45° C. for 1.5 hours. The excess thionyl chloride was evaporated using the evaporation of added toluene (x2) to remove the last traces. The resultant solid was suspended in a mixture of THF (250 ml) and methylene chloride (100 ml) and ammonia was bubbled though the mixture for 30 minutes. The resultant mixture was stirred for a further 1.5 hours at ambient temperature. The volatiles were removed by evaporation and the residue was dissolved in water and purified by column chromatography using a Diaion HP20SS resin column eluting with a gradient of methanol (0 to 5%) in water. The solvent was removed by evaporation from the fractions containing product. The residue was dissolved in a minimum of methanol and the solution was diluted with diethyl ether. The resultant precipitate was collected by filtration, washed with diethyl ether and dried under vacuum to give 5-methoxy-2-nitro-4-(3-pyrrolidin-1-ylpropoxy)benzamide (7.23 g); NMR Spectrum: (DMSOd₆ and CF₃CO₂D) 1.85–1.95 (m, 2H), 2–2.1 (m, 2H), 2.15–2.25 (m, 2H), 3.0–3.1 (m, 2H), 3.31 (t, 2H), 3.62 (t, 2H), 3.93 (s, 3H), 4.2 (t, 2H), 7.16 (s, 1H), 7.6 (s, 1H). A mixture of a portion (1.5 g) of the material so obtained, concentrated aqueous hydrochloric acid (5 ml) and methanol (20 ml) and was warmed to 50° C. to give a solution. Iron powder (1.3 g) was added in portions and the reaction mixture was heated to reflux for 1 hour. The mixture was allowed to cool to ambient temperature. Insoluble material was removed by filtration through diatomaceous earth and the filtrate was evaporated. The residue was purified by column chromatography using a Diaion HP20SS resin column, eluting with water and then with dilute aqueous hydrochloric acid (pH2). The fractions containing product were concentrated by evaporation and the resultant precipitate was collected by filtration and dried under vacuum over phosphorus pentoxide. There was thus obtained 2-amino-5-methoxy-4-(3-pyrrolidin-1-ylpropoxy)benzamide hydrochloride (1.44 g); NMR Spectrum: (DMSOd₆ and CF₃CO₂D) 1.9 (br s, 2H), 2.05 (br s, 2H), 2.2 (br s, 2H), 3.05 (br s, 2H), 3.3 (t, 2H), 3.61 (br s, 2H), 3.8 (s, 3H), 4.11 (t, 2H), 7.05 (s, 1H), 7.53 (s, 1H). After repetition of the previous reaction, a mixture of 2-amino-5-methoxy-4-(3-pyrrolidin-1-ylpropoxy)benzamide hydrochloride (5.92 g), Gold's reagent (3.5 g) and dioxane (50 ml) was heated to reflux for 5 hours. Acetic acid (0.7 ml) and sodium acetate (1.33 g) were added and the reaction mixture was heated to reflux for a further 5 hours. The mixture was allowed to cool to ambient temperature and evaporated. The residue was dissolved in water, adjusted to pH8 with 2N aqueous sodium hydroxide solution and purified on a Diaion HP20SS resin column eluting with methanol (gradient 0–50 %) in water. The fractions containing product were concentrated by evaporation and then freeze dried to give 6-methoxy-7-(3-pyrrolidin-1-ylpropoxy)-3,4-dihydroquinazolin-4-one (4.55 g); NMR Spectrum: (DMSOd₆ and CF₃CO₂D) 1.9 (m, 2H), 2.0–2.1 (m, 2H), 2.2–2.3 (m, 2H), 3.05 (m, 2H), 3.34 (t, 2H), 3.6–3.7 (br s, 2H), 3.94 (s, 3H), 4.27 (t, 2H), 7.31 (s, 1H), 7.55 (s, 1H), 9.02 (s, 1H). A mixture of a portion (1.7 g) of the material so obtained, thionyl chloride (25 ml) and DMF (0.2 ml) was heated at reflux for 3 hours. Excess thionyl chloride was removed by evaporation and by azeotroping with toluene (x2). The residue was suspended in diethyl ether and washed with a 10% aqueous-solution of sodium bicarbonate. The organic layer was dried over magnesium sulphate and evaporated to give 4-chloro-6-methoxy-7-(3-pyrrolidin-1-ylpropoxy)quinazoline (1.94 g); NMR Spectrum: (CDCl₃) 1.8 (br s, 4H), 2.17 (m, 2H), 2.6 (br s, 4H), 2.7 (t, 2H), 4.05 (s, 3H), 4.3 (t, 2H), 7.35 (s, 1H), 7.38 (s, 1H), 8.86 (s, 1H).

[3] The product gave the following characterising data; NMR Spectrum: (DMSOd₆ and CF₃COOD) 2.35 (m, 2H), 2.9 (s, 3H), 3.3–4.0 (br s, 10H), 4.05 (s, 3H), 4.35 (m, 2H), 6.1 (s, 2H), 7.0 (m, 3H), 7.4 (s, 1H), 8.35 (s, 1H), 8.85 (s, 1H); Mass Spectrum: M + H⁺ 452. The 4-chloro-7-[3-(4-methylpiperazin-1-yl)propoxyl[-6-methoxy-quinazoline used as a starting material was prepared as follows:-
A mixture of 3-bromopropanol (20 ml), N-methylpiperazine (29 ml), potassium carbonate (83 g) and ethanol (200 ml) was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distillation at about 60–70° C. under about 0.2 mm Hg to give 1-(3-hydroxypropyl)-4-methylpiperazine (17 g); NMR Spectrum: (CDCl₃) 1.72 (m, 2H), 2.3 (s, 3H), 2.2–2.8 (m, 8H), 2.6 (t, 2H), 3.8 (t, 2H), 5.3 (br s, 1H). 4-Toluenesulphonyl chloride (3.2 g) was added to a stirred mixture of 1-(3-hydroxypropyl)-4-methylpiperazine (2.4 g), triethylamine (4.6 ml) and methylene chloride (60 ml) and the resultant mixture was stirred at ambient temperature for 2 hours. The solution was washed in turn with a saturated aqueous sodium bicarbonate solution and with water and filtered through phase separating paper. The organic filtrate was evaporated to give 3-(4-methylpiperazin-1-yl)propyl 4-toluenesulphonate as an oil which crystallised on standing (3.7 g); Mass Spectrum: M + H⁺ 313. A mixture of the trifluoroacetic acid salt of 4-(4-chloro-2-fluorophenoxy)-7-hydroxy-6-methoxyquinazoline (3.2 g), 3-(4-methylpiperazin-1-yl)propyl 4-toluenesulphonate (3.0 g), potassium carbonate (6.1 g) and DMF (60 ml) was stirred at 90° C. for 5 hours. The resultant mixture was cooled to ambient temperature, poured into water (700 ml) and extracted with ethyl acetate (5 times). The combined extracts were washed in turn with water, a saturated aqueous sodium bicarbonate solution, water and brine. The ethyl acetate solution was dried over magnesium sulphate and evaporated. The residue was purified by column chromatography on silica using a 100:8:1 mixture of methylene chloride, methanol and a concentrated aqueous ammonium hydroxide solution (0.88 g/ml) as eluent. The material so obtained was triturated under diethyl ether. There was thus obtained 4-(4-chloro-2-fluorophenoxy)-6-methoxy-7-[3-(4-methylpiperazin-1-yl)propoxy]quinazoline (1.64 g); NMR Spectrum: (DMSOd₆) 1.95 (m, 2H), 2.14 (s, 3H), 2.35 (m, 8H), 2.44 (t, 2H), 3.96 (s, 3H), 4.22 (t, 2H), 7.38 (s, 1H), 7.4 (m, 1H), 7.54 (m, 2H), 7.68 (m, 1H), 8.55 (s, 1H). After repetition of the previous reaction, a mixture of 4-(4-chloro-2-fluorophenoxy)-6-methoxy-7-[3-(4-methylpiperazin-1-yl)propoxy]-quinazoline (2.6 g) and 2N aqueous hydrochloric acid solution (45 ml) was stirred and heated to 95° C. for 2 hours. The mixture was cooled to ambient temperature and basified by the addition of solid sodium bicarbonate The mixture was evaporated and the residue was purified by column chromatography on silica using a 50:8:1 mixture of methylene chloride, methanol and a concentrated aqueous ammonium hydroxide solution (0.88 g/ml) as eluent. There was thus obtained 6-methoxy-7-[3-(4-methylpiperazin-1- yl)propoxy]-3,4-dihydroquinazolin-4-one (1.8 g,); Mass Spectrum: M + H⁺ 333. After repetition of the previous reaction, a mixture of 6-methoxy-7-[3-(4-methylpiperazin-1-yl)propoxy]-3,4-dihydroquinazolin-4-one (2.15 g), thionyl chloride (25 ml) and DMF (0.18 ml) was stirred

TABLE I-continued and heated to reflux for 2 hours. The thionyl chloride was evaporated under vacuum and the residue azeotroped twice with toluene. The residue was taken up in water, basified by the addition of a saturated aqueous sodium bicarbonate solution and extracted with methylene chloride (4 times). The combined extracts were washed in turn with water and brine and filtered through phase separating paper. The filtrate was evaporated under vacuum and the residue was purified by column chromatography on silica using a 100:8:1 mixture of methylene chloride, methanol and a concentrated aqueous ammonium hydroxide solution (0.88 g/ml) as eluent. The solid so obtained was triturated under acetone, filtered and dried to give 4-chloro-6-methoxy-7-[3-(4-methylpiperazin-1-yl)propoxy]quinazoline (1.2 g); Mass Spectrum: M + H$^+$ 351.

[4] The product gave the following characterising data; NMR Spectrum: (DMSOd$_6$ and CF$_3$COOD) 1.4 (m, 1H), 1.7–1.9 (m, 5H), 2.35 (m, 2H), 2.95 (m, 2H), 3.25 (m, 2H), 3.55 (m, 2H), 4.05 (s, 3H), 4.3 (t, 2H), 6.1 (s, 2H), 7.0 (m, 3H), 7.45 (s, 1H), 8.25 (s, 1H), 8.85 (s, 1H); Mass Spectrum: M + H$^+$ 437. The 4-chloro-7-(3-piperidinopropoxy)-6-methoxyquinazoline used as a starting material was prepared as follows:-

Sodium hydride (60% suspension in mineral oil, 1.44 g) was added portionwise during 20 minutes to a solution of 7-benzyloxy-6-methoxy-3,4-dihydroquinazolin-4-one (International Patent Application WO 97/22596, Example 1 thereof; 8.46 g) in DMF (70 ml). The mixture was stirred at ambient temperature for 1.5 hours. Chloromethyl pivalate (5.65 g) was added dropwise and the mixture was stirred at ambient temperature for 2 hours. The mixture was diluted with ethyl acetate (100 ml) and poured onto a mixture (400 ml) of ice and water containing 2N aqueous hydrochloric acid (4 ml). The organic layer was separated and the aqueous layer was extracted with ethyl acetate. The combined extracts were washed with brine, dried over magnesium sulphate and evaporated. The residue was triturated under a mixture of diethyl ether and petroleum ether (b.p. 60–80° C.) and the resultant solid was collected and dried under vacuum. There was thus obtained 7-benzyloxy-6-methoxy-3-pivaloyloxymethyl-3,4-dihydro- quinazolin-4-one (10 g); NMR Spectrum: (DMSOd$_6$) 1.11 (s, 9H), 3.89 (s, 3H), 5.3 (s, 2H), 5.9 (s, 2H), 7.27 (s, 1H), 7.35 (m, 1H), 7.47 (t, 2H), 7.49 (d, 2H), 7.51 (s, 1H), 8.34 (s, 1H). A mixture of a portion (7 g) of the material so obtained, 10% palladium-on-charcoal catalyst (0.7 g), DMF (50 ml), methanol (50 ml), acetic acid (0.7 ml) and ethyl acetate (250 ml) was stirred under an atmosphere pressure of hydrogen for 40 minutes. The catalyst was removed by filtration and the solvent was evaporated. The residue was triturated under diethyl ether and the resultant solid was collected and dried under vacuum. There was thus obtained 7-hydroxy-6-methoxy-3-pivaloyloxymethyl-3,4-dihydroquinazolin-4-one (4.36 g); NMR Spectrum: (DMSOd$_6$) 1.1 (s, 9H), 3.89 (s, 3H), 5.89 (s, 2H), 7.0 (s, 1H), 7.48 (s, 1H), 8.5 (s, 1H). Diethyl azodicarboxylate (3.9 ml) was added dropwise to a stirred mixture of 7-hydroxy-6-methoxy-3-pivaloyloxymethyl-3,4-dihydroquinazolin-4-one (5 g), 3-bromopropanol (2.21 ml), triphenyl-phosphine (6.42 g) and methylene chloride (50 ml) and the mixture was stirred at ambient temperature for 2 hours. The mixture was evaporated and the residue was purified by column chromatography on silica using a 19:1 mixture of methylene chloride and methanol as eluent. There was thus obtained 7-(3-bromopropoxy)-6-methoxy-3-pivaloyloxymethyl-3,4-dihydroquinazolin-4-one (6 g); NMR Spectrum: (DMSOd$_6$) 1.12 (s, 9H), 2.32 (t, 2H), 3.7 (t, 2H), 3.9 (s, 3H), 4.25 (t, 2H), 5.9 (s, 2H), 7.2 (s, 1H), 7.61 (s, 1H), 8.36 (s, 1H). A mixture of a portion (2.89 g) of the material so obtained and piperidine (10 ml) was stirred and heated to 100° C. for 1 hour. The mixture was evaporated and the residue was partitioned between methylene chloride and a saturated aqueous ammonium chloride solution. The organic phase was washed with brine, dried over magnesium sulphate and evaporated. There was thus obtained 6-methoxy-7-(3-piperidinopropoxy)-3-pivaloyloxymethyl-3,4- dihydroquinazolin-4-one (2.4 g); NMR Spectrum: (DMSOd$_6$) 1.15 (s, 9H), 1.35–1.5 (m, 1H), 1.6–1.8 (m, 3H), 1.8–1.9 (m, 2H), 2.2–2.3 (m, 2H), 2.95 (t, 2H), 3.25 (t, 2H), 3.55 (d, 2H), 3.95 (s, 3H), 4.25 (t, 2H), 5.94 (s, 2H), 7.24 (s, 1H), 7.56 (s, 1H), 8.36 (s, 1H). A mixture of the material so obtained and a 7N solution of ammonia in methanol (50 ml) was stirred at ambient temperature for 16 hours. The mixture was evaporated and the residue was triturated under diethyl ether. The resultant solid was isolated, washed in turn with diethyl ether and a 1:1 mixture of diethyl ether and methylene chloride and dried under vacuum. There was thus obtained 6-methoxy-7-(3-piperidinopropoxy)-3,4-dihydroquinazolin-4-one (1.65 g); NMR Spectrum: (DMSOd$_6$) 1.3–1.4 (m, 2H), 1.4–1.55 (m, 4H), 1.85–1.95 (m, 2H), 2.35 (br s, 4H), 2.4 (t, 2H), 3.9 (s, 3H), 4.15 (t, 2H), 7.11 (s, 1H), 7.44 (s, 1H), 7.9 (s, 1H). A mixture of the material so obtained, thionyl chloride (15 ml) and DMF (1.5 ml) was heated to reflux for 3 hours. The mixture was evaporated. Toluene was added and the mixture was again evaporated. The residue was partitioned between methylene chloride and a saturated aqueous sodium bicarbonate solution (the basicity of which was adjusted to pH10 by adding 6N aqueous sodium hydroxide).

The organic layer was separated, washed with brine, dried over magnesium sulphate and evaporated. There was thus obtained 4-chloro-6-methoxy-7-(3-piperidinopropoxy)quinazoline (1.2 g); NMR Spectrum: (DMSOd$_6$) 1.35–1.45 (m, 2H), 1.5–1.6 (m, 4H), 1.9–2.05 (m, 2H), 2.4 (br s, 4H), 2.45 (t, 2H), 4.0 (s, 3H), 4.29 (t, 2H), 7.41 (s, 1H), 7.46 (s, 1H), 8.9 (s, 1H).

[5] The product gave the following characterising data; NMR Spectrum: (DMSOd$_6$ and CF$_3$COOD) 1.6 (m, 2H), 2.05 (m, 2H), 2.15 (m, 1H), 2.75 (s, 3H), 3.05 (m, 2H), 3.5 (m, 2H), 4.0 (s, 3H), 4.15 (d, 2H), 6.1 (s, 2H), 7.0 (m, 3H), 7.4 (s, 1H), 8.2 (s, 1H), 8.85 (s, 1H); Mass Spectrum: M + H$^+$ 423. The 4-chloro-7-(N-methylpiperidin-4-ylmethoxy)-6-methoxyquinazoline used as a starting material was prepared as follows:-

A solution of di-tert-butyl dicarbonate (41.7 g) in ethyl acetate (75 ml) was added dropwise to a stirred solution of ethyl piperidine-4-carboxylate (30 g) in ethyl acetate (150 ml) which had been cooled to 0 to 5° C. in an ice-bath. The resultant mixture was stirred at ambient temperature for 48 hours. The mixture was poured into water (300 ml). The organic layer was separated, washed in turn with water (200 ml), 0.1N aqueous hydrochloric acid solution (200 ml), a saturated aqueous sodium bicarbonate solution (200 ml) and brine (200 ml), dried over magnesium sulphate and evaporated. There was thus obtained ethyl N-tert-butoxy-carbonylpiperidine-4-carboxylate (48 g); NMR Spectrum: (CDCl$_3$) 1.25 (t, 3H), 1.45 (s, 9H), 1.55–1.7 (m, 2H), 1.8–2.0 (d, 2H), 2.35–2.5 (m, 1H), 2.7–2.95 (t, 2H), 3.9–4.1 (br s, 2H), 4.15 (q, 2H). A solution of the material so obtained in THF (180 ml) was cooled at 0° C. and lithium aluminium hydride (1M solution in THF; 133 ml) was added dropwise. The mixture was stirred at 0° C. for 2 hours. Water (30 ml) and 2N aqueous sodium hydroxide solution (10 ml) were added in turn and the mixture was stirred for 15 minutes. The resultant mixture was filtered through diatomaceous earth and the solids were washed with ethyl acetate. The filtrate was washed in turn with water and with brine, dried over magnesium sulphate and evaporated. There was thus obtained N-tert-butoxycarbonyl-4-hydroxymethylpiperidine (36.3 g); NMR Spectrum: (CDCl$_3$) 1.05–1.2 (m, 2H), 1.35–1.55 (m, 10H), 1.6–1.8 (m, 2H), 2.6–2.8 (t, 2H), 3.4–3.6 (t, 2H), 4.0–4.2 (br s, 2H). 1,4-Diazabicyclo[2.2.2]octane (42.4 g) was added to a solution of N-tert-butoxycarbonyl-4-hydroxymethylpiperidine (52.5 g) in tert-butyl methyl ether (525 ml) and the mixture was stirred at ambient temperature for 15 minutes. The mixture was then cooled in an ice-bath to 5° C. and a solution of 4-toluenesulphonyl chloride (62.8 g) in tert- butyl methyl ether (525 ml) was added dropwise over 2 hours while maintaining the reaction temperature at approximately 0° C.. The resultant mixture was allowed to warm to ambient temperature and was stirred for 1 hour. Petroleum ether (b.p. 60–80° C., 1L) was added and the precipitate was removed by filtration. The filtrate was evaporated to give a solid residue which was dissolved in diethyl ether. The organic solution was washed in turn with 0.5N aqueous hydrochloric acid solution, water, a saturated aqueous sodium bicarbonate solution and brine, dried over magnesium sulphate and evaporated. There was thus obtained N-tert-butoxycarbonyl-4-(4-toluenesulphonyloxymethyl) piperidine (76.7 g); NMR Spectrum: (CDCl$_3$) 1.0–1.2 (m, 2H), 1.45 (s, 9H), 1.65 (d, 2H), 1.75–1.9 (m, 2H), 2.45 (s, 3H), 2.55–2.75 (m, 2H), 3.85 (d, 1H), 4.0–4.2 (br s, 2H), 7.35 (d, 2H), 7.8 (d, 2H). A portion (40 g) of the material so obtained was added to a suspension of ethyl 4-hydroxy-3- methoxybenzoate (19.6 g) and potassium carbonate (28 g) in DMF (200 ml) and the resultant mixture was stirred and heated to 95° C. for 2.5 hours. The mixture was cooled to ambient temperature and partitioned between water and a mixture of ethyl acetate and diethyl ether. The organic layer was washed in turn with water and brine, dried over magnesium sulphate and evaporated. The resulting oil was crystallised from petroleum ether (b.p. 60–80° C.) and the suspension was stored overnight at 5° C.. The resultant solid was collected by filtration, washed with petroleum ether and dried under vacuum. There was thus obtained ethyl 4-(N-tert-butoxycarbonylpiperidin-4-ylmethoxy)-3-methoxybenzoate (35 g), m.p. 81–83° C.; NMR Spectrum: (CDCl$_3$) 1.2–1.35 (m, 2H), 1.4 (t, 3H), 1.48 (s, 9H), 1.8–1.9 (d, 2H), 2.0–2.15 (m, 2H), 2.75 (t, 2H), 3.9 (d, 2H), 3.95 (s, 3H), 4.05–4.25 (br s, 2H), 4.35 (q, 2H), 6.85 (d, 1H), 7.55 (s, 1H), 7.65 (d, 1H). The material so obtained was dissolved in formic acid (35 ml), formaldehyde (12M, 37% in water, 35 ml) was added and the mixture was stirred and heated to 95° C. for 3 hours. The resultant mixture was evaporated. The residue was dissolved in methylene chloride and hydrogen chloride (3M solution in diethyl ether; 40 ml) was added. The mixture was diluted with diethyl ether and the mixture was triturated until a solid was formed. The solid was collected, washed with diethyl ether and dried under vacuum overnight at 50° C.. There was thus obtained ethyl 3-methoxy-4-(N-methylpiperidin-4-ylmethoxy)benzoate (30.6 g); NMR Spectrum: (DMSOd$_6$) 1.29 (t, 3H), 1.5–1.7 (m, 2H), 1.95 (d, 2H), 2.0–2.15 (br s, 1H), 2.72 (s, 3H), 2.9–3.1 (m, 2H), 3.35–3.5 (br s, 2H), 3.85 (s, 3H), 3.9–4.05 (br s, 2H), 4.3 (q, 2H), 7.1 (d, 1H), 7.48 (s, 1H), 7.6 (d, 1H). The material so obtained was dissolved in methylene chloride (75 ml) and

TABLE I-continued the solution was cooled in an ice-bath to 0–5° C. Trifluoroacetic acid (37.5 ml) was added followed by the dropwise addition over 15 minutes of a solution of fuming nitric acid (24M; 7.42 ml) in methylene chloride (15 ml). The resultant solution was allowed to warm to ambient temperature and was stirred for 2 hours. Volatile materials were evaporated. The residue was dissolved in methylene chloride (50 ml) and the solution was cooled in an ice-bath to 0–5° C. Diethyl ether was added and the resultant precipitate was collected and dried under vacuum at 50° C.. The solid was dissolved in methylene chloride (500 ml) and hydrogen chloride (3M solution in diethyl ether; 30 ml) was added followed by diethyl ether (500 ml). The resultant solid was collected and dried under vacuum at 50° C. There was thus obtained ethyl 5-methoxy-4-(N-methylpiperidin-4-ylmethoxy)-2-nitrobenzoate (28.4 g); NMR Spectrum: (DMSOd$_6$) 1.3 (t, 3H), 1.45–1.65 (m, 2H), 1.75–2.1 (m, 3H), 2.75 (s, 3H), 2.9–3.05 (m, 2H), 3.4–3.5 (d, 2H), 3.95 (s, 3H), 4.05 (d, 2H), 4.3 (q, 2H), 7.32 (s, 1H), 7.66 (s, 1H). A mixture of a portion (3.89 g) of the material so obtained, 10% platinum-on-activated carbon (50% wet, 0.389 g) and methanol (80 ml) was stirred under 1.8 atmospheres pressure of hydrogen until uptake of hydrogen ceased. The mixture was filtered and the filtrate was evaporated. The residue was dissolved in water (30 ml) and basified to pH10 by the addition of a saturated aqueous sodium bicarbonate solution. The mixture was diluted with a 1:1 mixture of ethyl acetate and diethyl ether and the organic layer was separated. The aqueous layer was further extracted with a 1:1 mixture of ethyl acetate and diethyl ether and the organic extracts were combined, washed in turn with water and brine, dried over magnesium sulphate and evaporated. The residue was triturated under a mixture of petroleum ether (b.p. 60–80° C.) and diethyl ether. The solid so obtained was isolated, washed with petroleum ether and dried under vacuum at 60° C. There was thus obtained ethyl 2-amino-5-methoxy-4-(N-methylpiperidin-4-ylmethoxy)benzoate (2.58 g), m.p. 111–112° C.; NMR Spectrum: (CDCl$_3$) 1.35 (t, 3H), 1.4–1.5 (m, 2H), 1.85 (m, 3H), 1.95 (t, 2H), 2.29 (s, 3H), 2.9 (d, 2H), 3.8 (s, 3H), 3.85 (d, 2H), 4.3 (q, 2H), 5.55 (br s, 2H), 6.13 (s, 1H), 7.33 (s, 1H). A mixture of ethyl 2-amino-5-methoxy-4-(N-methylpiperidin-4-ylmethoxy)benzoate (16.1 g), formamidine acetic acid salt (5.2 g) and 2-methoxyethanol (160 ml) was stirred and heated at 115° C. for 2 hours. Further formamidine acetic acid salt (10.4 g) was added in portions every 30 minutes during 4 hours and heating was continued for 30 minutes after the last addition. The resultant mixture was evaporated. The solid residue was stirred under a mixture of methylene chloride (50 ml) and ethanol (100 ml). The precipitate was removed by filtration and the filtrate was concentrated to a final volume of 100 ml. The resultant suspension was cooled to 5° C.. The solid so obtained was collected, washed with cold ethanol and with diethyl ether and dried under vacuum at 60° C. There was thus obtained 6-methoxy-7-N-methylpiperidin-4-ylmethoxy)-3,4-dihydroquinazolin-4-one (12.7 g); NMR Spectrum: (DMSOd$_6$) 1.25–1.4 (m, 2H), 1.75 (d, 2H), 1.9 (t, 1H), 1.9 (s, 3H), 2.16 (s, 2H), 2.8 (d, 2H), 3.9 (s, 3H), 4.0 (d, 2H), 7.11 (s, 1H), 7.44 (s, 1H), 7.97 (s, 1H). A mixture of a portion (2.8 g) of the material so obtained, thionyl chloride (28 ml) and DMF (0.28 ml) was heated to reflux for 1 hour. The mixture was evaporated and the precipitate was triturated under diethyl ether. The resultant solid was isolated and washed with diethyl ether. The solid was then dissolved in methylene chloride and the solution was washed with a saturated aqueous sodium bicarbonate solution. The organic layer was washed in turn with water and brine, dried over magnesium sulphate and evaporated. There was thus obtained 4-chloro-6-methoxy-7-(N-methylpiperidin-4-ylmethoxy)quinazoline (2.9 g); NMR Spectrum: (DMSOd$_6$) 1.3–1.5 (m, 2H), 1.75–1.9 (m, 4H), 2.0 (t, 1H), 2.25 (s, 3H), 2.85 (d, 2H), 4.02 (s, 3H), 4.12 (d, 2H), 7.41 (s, 1H), 7.46 (s, 1H), 8.9 (s, 1H).[6] The product gave the following characterising data; NMR Spectrum: (DMSOd$_6$ and CF$_3$COOD) 2.9 (s, 3H), 3.5–3.95 (br s, 14H), 4.05 (s, 3H), 4.4 (br s, 2H), 6.1 (s, 2H), 7.0 (m, 3H), 7.45 (s, 1H), 8.25 (s, 1H), 8.85 (s, 1H); Mass Spectrum: M + H$^+$ 482. The 4-chloro-6-methoxy-7-{2-[2-(4-methylpiperazin-1-yl)ethoxy]-ethoxy}quinazoline used as a starting material was prepared as follows:-Diisopropyl azodicarboxylate (5.78 ml) was added dropwise to a stirred mixture of 7-hydroxy-6-methoxy-3-pivaloyloxymethyl-3,4-dihydroquinazolin-4-one (6.0 g), 2-(2-chloroethoxy)ethanol (2.5 ml), triphenyl phosphine (7.7 g) and methylene chloride (150 ml) and the reaction mixture was stirred at ambient temperature for 2 hours. The solvent was evaporated and the residue was purified by column chromatography on silica using a 4:1 mixture of petroleum ether (b.p. 40–60° C.) and ethyl acetate as eluent. There was thus obtained 7-[2-(2-chloroethoxy)ethoxy]-6-methoxy-3-pivaloyloxymethyl-3,4-dihydroquinazolin-4-one (6.32 g); NMR Spectrum: (DMSOd$_6$) 1.15 (s, 9H), 3.8 (m, 4H), 3.85 (m, 2H), 3.9 (s, 3H), 4.3 (m, 2H), 5.9 (s, 2H), 7.25 (s, 1H), 7.5 (s, 1H), 8.4 (s, 1H), Mass Spectrum: M + H$^+$ 413. A mixture of a portion (4.0 g) of the material so obtained and N-methyl-piperazine (60 ml) was stirred and heated at 80° C. for 5 hours. The mixture was evaporated and the residue partitioned between methylene chloride and a saturated aqueous ammonium chloride solution. The organic phase was dried over magnesium sulphate and evaporated. There was thus obtained 6-methoxy-7-{2-[2-(4-methylpiperazin-1-yl)ethoxy]-ethoxy}-3-pivaloyloxymethyl-3,4-dihydroquinazolin-4-one (3.91 g); Mass Spectrum: M + H$^+$ 477. A mixture of the material so obtained, a 2N aqueous sodium hydroxide solution (7.95 ml) and methanol (20 ml) was stirred at ambient temperature for 2 hours. The basicity of the solution was adjusted to pH10 by the addition of 2N aqueous hydrochloric acid solution. The mixture was evaporated and the residue was triturated under methylene chloride. The resultant mixture was filtered and the filtrate was evaporated. The resultant residue was triturated under a mixture of diethyl ether and methanol. There was thus obtained 6-methoxy-7-{2-[2-(4-methylpiperazin-1-yl)ethoxy]ethoxy}-3,4-dihydroquinazolin-4-one (2.24 g); Mass Spectrum: M + H$^+$ 363. A mixture of the material so obtained, thionyl chloride (22 ml) and DMF (0.2 ml) was stirred and heated to 80° C. for 1.5 hours. The mixture was evaporated, toluene was added and the mixture was again evaporated. Methylene chloride and water were added to the residue and the resultant mixture was cooled to 0° C. and adjusted to pH12 by the successive addition of solid sodium bicarbonate and 2N aqueous sodium hydroxide solution. The organic phase was washed with brine, dried over magnesium sulphate and evaporated. The resultant yellow solid was triturated under a mixture of pentane and diethyl ether. There was thus obtained 4-chloro-6-methoxy-7-{2-[2-(4-methylpiperazin-1-yl)ethoxy]-ethoxy}quinazoline (1.19 g); NMR Spectrum: (DMSOd$_6$) 2.15 (s, 3H), 2.2–2.45 (br s, 8H), 2.5 (t, 2H), 3.6 (t, 2H), 3.85 (t, 2H), 4.05 (s, 3H), 4.4 (t, 2H), 7.45 (s, 1H), 7.5 (s, 1H), 8.9 (s, 1H), Mass Spectrum: M + H$^+$ 381.

[7] 4-Chloro-6,7-dimethoxyquinazoline, used as a starting material, is described in European Patent Application No. 0566226 (Example 1 thereof). The product was obtained as a monohydrochloride salt and gave the following characterising data; NMR Spectrum: (DMSOd$_6$) 4.0 (s, 6H), 6.05 (s, 2H), 6.95 (m, 3H), 7.35 (s, 1H), 8.2 (s, 1H), 8.8 (s, 1H); Mass Spectrum: M + H$^+$ 326.

[8] Isopropanol was used in place of pentan-2-ol as the reaction solvent and the reaction mixture was heated to 80° C. for 30 minutes. The product gave the following characterising data; NMR Spectrum: (DMSOd$_6$ and CF$_3$CO$_2$D) 4.0 (s, 3H), 5.35 (s, 2H), 6.1 (s, 2H), 6.95 (m, 3H), 7.45 (m, 4H), 7.55 (d, 2H), 8.15 (s, 1H), 8.85 (s, 1H); Mass Spectrum: M + H$^+$ 402.

[9] The product gave the following characterising data; NMR Spectrum: (DMSOd$_6$ and CF$_3$CO$_2$D) 2.35 (m, 2H), 3.15 (m, 2H), 3.35 (m, 2H), 3.55 (d, 2H), 3.8 (m, 2H), 4.0 (m, 2H), 4.05 (s, 3H), 4.35 (m, 2H), 6.15 (s, 2H), 7.05 (d, 1H), 7.15 (d, 1H), 7.45 (s, 1H), 8.25 (s, 1H), 8.9 (s, 1H); Mass Spectrum: M − H$^−$ 455 and 457. The 6-chloro-2,3-methylenedioxyaniine used as a starting material was prepared as follows:-Sulphuryl chloride (72.5 ml) was added dropwise during 1.7 hours to a stirred mixture of benzodioxole (100 g), aluminium trichloride (0.43 g) and diphenyl sulphide (0.55 ml). Once the reaction started with the evolution of sulphur dioxide, the reaction mixture was cooled in a water bath to a temperature of approximately 22° C. After completion of the addition, the reaction mixture was stirred at ambient temperature for 45 minutes. The reaction mixture was degassed under vacuum and filtered and the filtrate was distilled at atmospheric pressure using a Vigreux distillation column. There was thus obtained 5-chloro-1,3-benzodioxole; b.p. 185–187° C.; NMR Spectrum: (CDCl$_3$) 6.0 (s, 2H); 6.7 (d, 1H); 6.75–6.9 (m,2H). A mixture of diisopropylamine (4.92 ml) and THF (100 ml) was cooled to −78° C. and n-butyllithium (2.5 M in hexane, 14 ml) was added dropwise. The mixture was stirred at −78° C. for 15 minutes. 5-Chloro-1,3-benzodioxole (3.73 ml) was added dropwise and the reaction mixture was stirred at −78° C. for 30 minutes. Dry carbon dioxide gas was bubbled into the reaction mixture for 30 minutes. The resultant reaction mixture was allowed to warm to ambient temperature and was stirred for a further thus obtained tert-butyl 5-chloro-1,3-benzodioxol-4-ylcarbamate (1.1 g); thus obtained hour. Water was added and the organic solvent was evaporated. The residue was acidified to pH2 by the addition of 2N aqueous hydrochloric acid solution. The resultant solid was isolated and washed in turn with water and diethyl ether. There was thus obtained 5-chloro-1,3-benzodioxole-4-carboxylic acid (5.4 g); NMR Spectrum: (DMSOd$_6$) 6.15 (s, 2H), 7.0 (m, 2H), 13.7 (br s, 1H). A portion (1 g) of the material so obtained was dissolved in 1,4-dioxane (15 ml) and anhydrous tert-butanol (4 ml), diphenylphosphoryl azide (1.12 ml) and triethylamine (0.73 ml) were added in thus obtained tert-butyl 5-chloro-1,3-benzodioxol-4-ylcarbamate (1.1 g); turn. The resultant mixture was stirred and heated to 100° C. for 4 hours. thus obtained tert-butyl 5-chloro-1,3-benzodioxol-4-ylcarbamate (1.1 g); The mixture was evaporated and the residue was partitioned between ethyl acetate and a 5% aqueous citric acid solution. The organic phase was washed in turn with water, a saturated aqueous sodium bicarbonate solution and brine, dried over magnesium sulphate and evaporated. The TABLE I-continued resithus obtained tert-butyl 5-chloro-1,3-benzodioxol-4-ylcarbamate (1.1 g); due was purified by column chromatography on silica using a 9:1 mixture of petroleum ether (b.p. 40–60° C.) and ethyl acetate as eluent. There was thus obtained tert-butyl 5-chloro-1,3-benzodioxol-4-ylcarbamate (1.1 g); thus obtained tert-butyl 5-chloro-1,3-benzodioxol-4-ylcarbamate (1.1 g); NMR Spectrum: (DMSOd$_6$) 1.45 (s, 9H), 6.1 (s, 2H), 6.85 (d, 1H), 6.95 (d, 1H), 8.75 (s, 1H). A mixture of the material so obtained (1.1 g), trifluoroacetic acid (6 ml) and methylene chloride (20 ml) was stirred at ambient temperature for 3 hours. The solvent was evaporated and the residue was partitioned between ethyl acetate and a saturated aqueous sodium bicarbonate solution. The organic phase was washed with brine, dried over magnesium sulphate and evaporated. There was thus obtained 6-chloro-2,3-methylenedioxyaniline (0.642 g); NMR Spectrum: (DMSOd$_6$) 5.15 (s, 2H), 6.0 (s, 2H), 6.25 (d, 1H), 6.75 (d, 1H).

[10] The product gave the following characterising data; NMR Spectrum: (DMSOd$_6$ and CF$_3$CO$_2$D) 2.35 (m, 2H), 3.15 (m, 2H), 3.35 (m, 2H), 3.5 (m, 2H), 3.8 (m, 2H), 4.0 (m, 2H), 4.05 (s, 3H), 4.35 (m, 2H), 6.15 (s, 2H), 7.05 (d, 1H), 7.15 (d, 1H), 7.45 (s, 1H), 8.25 (s, 1H), 8.9 (s, 1H); Mass Spectrum: M + H$^+$ 473 and 475.

[11] The reaction product was purified by column chromatography on silica using a 4:1 mixture of methylene chloride and methanol as eluent. The material so obtained was dissolved in a mixture of methylene chloride and methanol and a 6M solution of hydrogen chloride in diethyl ether was added. The dihydrochloride salt so obtained was isolated and dried and gave the following characterising data; NMR Spectrum: (DMSOd$_6$ and CF$_3$CO$_2$D) 2.65 (m, 2H), 2.9 (s, 3H), 3.35–3.55 (br m, 6H), 3.7–3.9 (br m, 4H), 4.05 (s, 3H), 4.35 (m, 2H), 6.15 (s, 2H), 7.05 (d, 1H), 7.15 (d, 1H), 7.45 (s, 1H), 8.25 (s, 1H), 8.85 (s, 1H); Mass Spectrum: M + H$^+$ 486 and 488.

[12] The reaction product was purified by column chromatography on silica using a 9:8:2 mixture of methylene chloride, methanol and a saturated methanolic ammonia solution as eluent. The material so obtained was dissolved in a mixture of methylene chloride and methanol and a 6M solution of hydrogen chloride in diethyl ether was added. The dihydrochloride salt so obtained was isolated and gave the following characterising data; NMR Spectrum: (DMSOd$_6$ and K$_2$CO$_3$) 1.55 (m, 2H), 1.9 (m, 2H), 2.0 (m, 1H), 2.5 (m, 5H), 3.15 (m, 2H), 3.95 (s, 3H), 4.05 (m, 2H), 6.1 (s, 2H), 6.95 (d, 1H), 7.05 (d, 1H), 7.2 (s, 1H), 7.9 (s, 1H), 8.35 (d, 1H), 9.55 (s, 1H); Mass Spectrum: M − H$^−$ 455 and 457.

[13] The following variation of the standard reaction procedure was used:- A mixture of 7-benzyloxy-4-chloro-6-methoxyquinazoline (3 g), 5-chloro-2,3-methylenedioxyaniline (1.88 g), a 6M solution of hydrogen chloride in isopropanol (0.166 ml) and isopropanol (60 ml) was stirred and heated to 80° C. for 3 hours. The reaction mixture was allowed to cooled to ambient temperature and the solid was isolated, washed with isopropanol and with diethyl ether. There was thus obtained the required product as a dihydro chloride salt (4.18 g); NMR Spectrum: (DMSOd$_6$) 4.0 (s, 3H), 5.35 (s, 2H), 6.15 (s, 2H), 7.05 (d, 1H), 7.15 (d, 1H), 7.45 (m, 4H), 7.55 (d, 2H), 8.25 (s, 1H), 8.8 (s, 1H).

[14] The reaction product was purified by column chromatography on silica using increasingly polar mixture of methylene chloride and a saturated methanolic ammonia solution as eluent. The product was obtained as the free base and gave the following characterising data; NMR Spectrum: (DMSOd$_6$ and CF$_3$CO$_2$D) 2.3 (m, 2H), 3.15 (m, 2H), 3.35 (t, 2H), 3.55 (d, 2H), 3.7 (t, 2H), 4.0 (s, 3H), 4.05 (m, 2H), 4.35 (t, 2H), 6.15 (s, 2H), 7.05 (d, 1H), 7.3 (d, 1H), 7.4 (s, 1H), 8.15 (s, 1H), 8.9 (s, 1H); Mass Spectrum: M + H$^+$ 517 and 519. The 6-bromo-2,3-methylenedioxyaniline used as a starting material was prepared from 5-bromo-1,3-benzodioxole (Aldrich Chemical Company) using analogous procedures to those described in Note [9] above for the preparation of 6-chloro-2,3-methylenedioxyaniline. There were thus obtained in turn:- 5-bromo-1,3-benzodioxole-4-carboxylic acid; NMR Spectrum: (DMSOd$_6$ and CF$_3$CO$_2$D) 6.15 (s, 2H), 6.95 (d, 1H), 7.1 (d, 1H); Mass Spectrum: [M − H]$^−$ 243; tert-butyl 5-bromo-1,3-benzodioxol-4-ylcarbamate; NMR Spectrum: (DMSOd$_6$) 1.45 (s, 9H), 6.1 (s, 2H), 6.80 (d, 1H), 7.1 (d, 1H), 8.70 (s, 1H); and 6-bromo-2,3-methylenedioxyaniline; NMR Spectrum: (DMSOd$_6$) 5.05 (s, 2H), 6.0 (s, 2H), 6.25 (d, 1H), 6.9 (d, 1H); Mass Spectrum: M + H$^+$ 216 and 218.

[15] The reaction product was purified by column chromatography on silica using increasingly polar mixture of methylene chloride and a saturated methanolic ammonia solution as eluent. The product was obtained as the free base and gave the following characterising data; NMR Spectrum: (DMSOd$_6$ and CF$_3$CO$_2$D) 2.3 (m, 2H), 3.05 (s, 3H), 3.35 (t, 2H), 4.05 (s, 3H), 4.35 (t, 2H), 6.15 (s, 2H), 7.05 (d, 1H), 7.3 (d, 1H), 7.35 (s, 1H), 8.15 (s, 1H), 8.9 (s, 1H); Mass Spectrum: M + H$^+$ 510 and 512; Elemental Analysis: Found C, 47.44; H, 4.24; N, 7.92; C$_{20}$H$_{20}$BrN$_3$O$_6$S requires C, 47.07; H, 3.95; N, 8.23%. The 4-chloro-6-methoxy-7-(3-methylsulphonylpropoxy)quinazoline used as a starting material is described in International Patent Application WO 00/47212 (example 50 thereof).

[16] The product gave the following characterising data; NMR Spectrum: (DMSOd$_6$ and CF$_3$CO$_2$D) 2.35 (m, 2H), 3.15 (m, 2H), 3.35 (m, 2H), 3.55 (m, 2H), 3.75 (s, 3H), 3.8 (m, 2H), 4.0 (br s, 5H), 4.35 (m, 2H), 6.05 (s, 2H), 6.55 (s, 1H), 6.75 (s, 1H), 7.4 (s, 1H), 8.2 (s, 1H), 8.9 (s, 1H); Mass Spectrum: M + H$^+$ 469; Elemental Analysis: Found C, 51.59; H, 6.01; N, 9.46; C$_{24}$H$_{28}$N$_4$O$_6$ 2.1HCl 0.8H$_2$O requires C, 51.52; H, 5.71; N, 10.01%. The 5-methoxy-2,3-methylenedioxyaniline used as a starting material was prepared from 4-bromo-6-methoxy-1,3-benzodioxole (J Org. Chem., 1985, 50, 5077) using analogous procedures to those described in Note [9] above for the preparation of 6-chloro-2,3-methylenedioxyaniline. There were thus obtained in turn:- 6-methoxy-1,3-benzodioxole-4-carboxylic acid; NMR Spectrum: (DMSOd$_6$) 3.75 (s, 3H), 6.1 (s, 2H), 6.7 (s, 1H), 6.85 (s, 1H), 13.0 (br s, 1H); tert-butyl 6-methoxy-1,3- benzodioxol-4-ylcarbamate; NMR Spectrum: (DMSOd$_6$) 1.45 (s, 9H), 3.7 (s, 3H), 5.95 (s, 2H), 6.4 (s, 1H), 6.55 (br s, 1H), 8.85 (br s, 1H); Mass Spectrum: M + Na$^+$ 290; and 5-methoxy-2,3-methylenedioxyaniline; NMR Spectrum: (DMSOd$_6$) 3.6 (s, 3H), 4.95 (br s, 2H), 5.85 (s, 2H), 5.9 (s, 1H); Mass Spectrum: M + H$^+$ 168.

[17] The product gave the following characterising data; Mass Spectrum: M + H$^+$ 497. The 7-(2-acetoxy-3-morpholinopropoxy)-4-chloro-6-methoxyquinazoline used as a starting material was prepared as follows:-

A mixture of 7-hydroxy-6-methoxy-3-pivaloyloxymethyl-3,4-dihydroquinazolin-4-one (40 g), 2,3-epoxypropyl bromide (16.8 ml), potassium carbonate (36 g) and DMF (400 ml) was stirred and heated to 70° C. for 1.5 hours. The mixture was poured into an ice-water mixture (1.5 L) and the resultant precipitate was isolated, washed in turn with water and diethyl ether and dried under vacuum over phosphorus pentoxide. There was thus obtained 7-(2,3-epoxypropoxy)-6-methoxy-3-pivaloyloxy-methyl-3,4- dihydroquinazolin-4-one (46.7 g). A mixture of a portion (8 g) of the material so obtained, morpholine (5.8 ml) and chloroform (120 ml) was heated to reflux for 16 hours. The mixture was evaporated and the residue was purified by column chromatography on silica using a 19:1 mixture of methylene chloride and methanol as eluent. There was thus obtained 7-(2-hydroxy-3-morpholinopropoxy)-6-methoxy-3-pivaloyloxymethyl-3,4-dihydroquinazolin-4-one as a foam (8.2 g); NMR Spectrum: (CDCl$_3$) 1.2 (s, 9H), 2.5 (m, 2H), 2.6 (m, 2H), 2.7 (m, 2H), 3.5 (br s, 1H), 3.75 (m, 4H), 3.95 (s, 3H), 4.15 (m, 2H), 4.25 (m, 1H), 5.95 (s, 2H), 7.15 (s, 1H), 7.65 (s, 1H), 8.2 (s, 1H). A mixture of the material so obtained and a saturated methanolic ammonia solution was stirred at ambient temperature for 24 hours. The mixture was evaporated and the resultant solid was washed with diethyl ether and a 19:1 mixture of diethyl ether and methylene chloride. There was thus obtained 7-(2-hydroxy-3-morpholinopropoxy)- 6-methoxy-3,4-dihydroquinazolin-4-one (6.34 g); NMR Spectrum: (DMSOd$_6$) 2.4 (m, 6H), 3.55 (m, 4H), 3.85 (s, 3H), 4.0 (m, 2H), 4.15 (m, 1H), 4.95 (br s, 1H), 7.15 (s, 1H), 7.45 (s, 1H), 7.95 (s, 1H). A mixture of a portion (5.2 g) of the material so obtained, acetic anhydride (20 ml) and pyridine (1 ml) was stirred at ambient temperature for 30 minutes. The resultant mixture was poured into an ice-water mixture and stirred for 30 minutes. The mixture was then cooled in an ice-bath and a saturated solution of sodium bicarbonate was slowly added to adjust the pH to 9. The mixture was extracted with methylene chloride and the organic phase was washed with water and with brine, dried over magnesium sulphate and evaporated. The residue was purified by column chromatography on silica using a 93:7 mixture of methylene chloride and methanol as eluent. There was thus obtained 7-(2-acetoxy-3-morpholinopropoxy)-6-methoxy-3,4-dihydroquinazolin-4-one as a solid (5 g); NMR Spectrum: (DMSOd$_6$) 2.05 (s, 3H), 2.4 (m, 4H), 2.6 (m, 2H), 3.55 (m, 4H), 3.85 (s, 3H), 4.35 (m, 2H), 5.25 (m, 1H), 7.2 (s, 1H), 7.45 (s, 1H), 8.0 (s, 1H); Mass Spectrum: M + H$^+$ 378. A mixture of the material so obtained, thionyl chloride (60 ml) and DMF (0.5 ml) was heated to reflux for 1 hour. The mixture was evaporated, toluene was added and the mixture was evaporated. A mixture of ice and water was added to the residue and the mixture was basified to pH8.5 by the addition of a saturated aqueous sodium bicarbonate solution. The mixture was extracted with methylene chloride. The organic phase was washed with water and with brine, dried over magnesium sulphate and evaporated. The residue was purified by column chromatography on silica using a 97:3 mixture of methylene chloride and methanol as eluent. There was thus obtained 7-(2-acetoxy-3-morpholinopropoxy)-4-chloro-6-methoxyquinazoline as a foam (4.56 g); NMR Spectrum: (CDCl$_3$) 2.1 (s, 3H), 2.55 (m, 4H), 2.7 (d, 2H), 3.7 (m, 4H), 4.05 (s, 3H), 4.35 (m, 1H), 4.45 (m, 1H), 5.45 (m, 1H), 7.4 (d, 2H), 8.85 (s, 1H); Mass Spectrum: M + H$^+$ 396 and 398.

[18] The product gave the following characterising data; Mass Spectrum: M + H$^+$ 481. The 7-(2-acetoxy-3-pyrrolidin-1-ylpropoxy)-4-chloro-6-methoxy-quinazoline used as a starting material was prepared as follows:-

7-(2,3-Epoxypropoxy)-6-methoxy-3-pivaloyloxymethyl-3,4-dihydroquinazolin-4-one was reacted with pyrrolidine using an analogous proce- TABLE I-continued dure to that described in the second paragraph of the portion of Note [17] immediately above that is concerned with the preparation of starting materials. There was thus obtained 7-(2-hydroxy-3-pyrrolidin-1-ylpropoxy)-6-methoxy-3-pivaloyloxymethyl-3,4-dihydroquinazolin-4-one. The material so obtained was taken through an analogous sequence of reactions to those described in the third to fifth paragraphs of the portion of Note [17] immediately above that is concerned with the preparation of starting materials. There was thus obtained 7-(2-acetoxy-3-pyrrolidin-1-ylpropoxy)-4-chloro-6-methoxyquinazoline; NMR Spectrum: (CDCl$_3$ and CD$_3$CO$_2$D) 2.05 (s, 4H), 2.15 (s, 3H), 3.45 (br s, 4H), 3.65 (m, 2H), 4.05 (s, 3H), 4.4 (d, 2H), 5.65 (m, 1H), 7.4 (s, 1H), 7.55 (s, 1H), 8.9 (s, 1H).

[19] The product gave the following characterising data; Mass Spectrum: M + H$^+$ 495. The 7-(2-acetoxy-3-piperidinopropoxy)-4-chloro-6-methoxyquinazoline used as a starting material was prepared as follows:-

7-(2,3-Epoxypropoxy)-6-methoxy-3-pivaloyloxymethyl-3,4-dihydroquinazolin-4-one was reacted with piperidine using an analogous procedure to that described in the second paragraph of the portion of Note [17] immediately above that is concerned with the preparation of starting materials. There was thus obtained 7-(2-hydroxy-3-piperidinopropoxy)-6-methoxy-3-pivaloyloxymethyl-3,4-dihydroquinazolin-4-one. The material so obtained was taken through an analogous sequence of reactions to those described in the third to fifth paragraphs of the portion of Note [17] immediately above that is concerned with the preparation of starting materials. There was thus obtained 7-(2-acetoxy-3-piperidinopropoxy)-4-chloro-6-methoxyquinazoline; NMR Spectrum: (CDCl$_3$ and CD$_3$CO$_2$D) 1.6 (m, 2H), 1.9 (m, 4H), 2.1 (s, 3H), 3.2 (br s, 4H), 3.5 (m, 2H), 4.05 (s, 3H), 4.35 (m, 2H), 5.7 (m, 1H), 7.4 (s, 1H), 7.5 (s, 1H), 8.9 (s, 1H).

[20] The product gave the following characterising data; Mass Spectrum: M + H$^+$ 535. The 7-[2-acetoxy-3-(4-cyanomethylpiperazin-1-yl)propoxy]-4-chloro-6-methoxyquinazoline used as a starting material was prepared as follows:-

7-(2,3-Epoxypropoxy)-6-methoxy-3-pivaloyloxymethyl-3,4-dihydroquinazolin-4-one was reacted with 1-cyanomethylpiperazine using an analogous procedure to that described in the second paragraph of the portion of Note [17] immediately above that is concerned with the preparation of starting materials. There was thus obtained 7-[3-(4-cyanomethylpiperazin-1-yl)-2-hydroxypropoxy]-6-methoxy-3-pivaloyloxymethyl-3,4-dihydroquinazolin-4-one. The material so obtained was taken through an analogous sequence of reactions to those described in the third to fifth paragraphs of the portion of Note [17] immediately above that is concerned with the preparation of starting materials. There was thus obtained 7-[2-acetoxy-3-(4-cyanomethylpiperazin-1-yl)propoxy]-4-chloro-6-methoxyquinazoline; NMR Spectrum: (CDCl$_3$) 2.1 (s, 3H), 2.65 (br s, 10H), 3.5 (s, 2H), 4.05 (s, 3H), 4.4 (m, 2H), 5.45 (m, 1H), 7.25 (s, 1H), 7.4 (s, 1H), 8.85 (s, 1H); Mass Spectrum: M + H$^+$ 434 and 436. The 1-cyanomethylpiperazine used as a starting material was prepared as follows:-

A mixture of 1-(tert-butoxycarbonyl)piperazine (5 g), 2-chloroacetonitrile (1.9 ml), potassium carbonate (4 g) and DMF (20 ml) was stirred at ambient temperature for 16 hours. A saturated aqueous ammonium chloride solution was added and the mixture was extracted with ethyl acetate. The organic phase was dried over magnesium sulphate and evaporated. The residue was purified by column chromatography on silica using diethyl ether as eluent. There was thus obtained 1-(tert-butoxy-carbonyl)-4- cyanomethylpiperazine as a solid (5.7 g); NMR Spectrum: (CDCl$_3$) 1.45 (s, 9H), 2.5 (m, 4H), 3.45 (m, 4H), 3.55 (s, 2H). A mixture of the material so obtained, trifluoroacetic acid (20 ml) and methylene chloride (25 ml) was stirred at ambient temperature for 4 hours. The mixture was evaporated, toluene was added and the mixture was evaporated again. The residue was purified by column chromatography on silica using a 9:1 mixture of methylene chloride and methanol as eluent. There was thus obtained 1-cyanomethylpiperazine trifluoroacetate salt which was treated with solid sodium bicarbonate in a mixture of methylene chloride, ethyl acetate and methanol to give the free base form (2.9 g); NMR Spectrum: (CDCl$_3$ and DMSOd$_6$) 2.7 (m, 4H), 3.2 (m, 4H), 3.6 (s, 2H), 6.2 (br s, 1H).

[21] The product gave the following characterising data; Mass Spectrum: M + H$^+$ 483. The 7-[2-acetoxy-3-(N-isopropyl-N-methylamino)propoxy]-4-chloro-6-methoxyquinazoline used as a starting material was prepared as follows:-

7-(2,3-Epoxypropoxy)-6-methoxy-3-pivaloyloxymethyl-3,4-dihydroquinazolin-4-one was reacted with N-isopropyl-N-methylamine using an analogous procedure to that described in the second paragraph of the portion of Note [17] immediately above that is concerned with the preparation of starting materials. There was thus obtained 7-[2-hydroxy-3-(N-isopropyl-N-methylamino)propoxy]-6-methoxy-3-pivaloyloxy-methyl-3,4-dihydroquinazolin-4-one. The material so obtained was taken through an analogous sequence of reactions to those described in the third to fifth paragraphs of the portion of Note [17] immediately above that is concerned with the preparation of starting materials. There was thus obtained 7-[2-acetoxy-3-(N-isopropyl-N-methylamino)propoxy]-4-chloro-6-methoxyquinazoline; NMR Spectrum: (CDCl$_3$) 1.0 (d, 6H), 2.1 (s, 3H), 2.3 (s, 3H), 2.6 (m, 1H), 2.75 (m, 1H), 2.85 (m, 1H), 4.05 (s, 3H), 4.35 (m, 1H), 4.45 (m, 1H), 5.35 (m, 1H), 7.25 (s, 1H), 7.4 (s, 1H), 8.85 (s, 1H).

[22] The product gave the following characterising data; NMR Spectrum: (DMSOd$_6$ and CF$_3$CO$_2$D) 1.3 (m, 2H), 1.7 (m, 2H), 1.9–2.2 (m, 4H), 2.8 (s, 3H), 3.05 (m, 2H), 3.5 (m, 2H), 3.75 (m, 3H), 4.05 (s, 3H), 4.1 (m, 2H), 6.05 (s, 2H), 6.55 (s, 1H), 6.7 (s, 1H), 7.45 (s, 1H), 8.2 (s, 1H), 8.85 (s, 1H).

[23] Isopropanol was used in place of pentan-2-ol as the reaction solvent and the reaction mixture was heated to 80° C. for 1.5 hours. The reaction mixture was cooled to ambient temperature and evaporated. A mixture of the residue and methylene chloride (5 ml) was diluted with 1N aqueous sodium hydroxide solution (2 ml) and extracted with methylene chloride. The organic phase was evaporated and the residue was purified by column chromatography on silica using a 9:10:1 mixture of methylene chloride, ethyl acetate and a saturated methanolic ammonia solution as eluent. The material so obtained was dissolved in diethyl ether and a 6M solution of hydrogen chloride in isopropanol was added. The dihydro-chloride salt so obtained was isolated and dried and gave the following characterising data; NMR Spectrum: (DMSOd$_6$ and CF$_3$CO$_2$D) 1.4–1.5 (m, 2H), 1.7–1.9 (m, 3H), 2.0 (d, 2H), 2.75 (s, 3H), 2.95 (m, 2H), 3.45 (d, 2H), 4.0 (s, 3H), 4.3 (t, 2H), 6.1 (s, 2H), 7.0 (m, 3H), 7.38 (s, 1H), 8.12 (s, 1H), 8.9 (s, 1H); Mass Spectrum: M + H$^+$ 437. The 4-chloro-6-methoxy-7-[2-(N-methylpiperidin-4-yl)ethoxy]quinazoline used as a starting material is described International Patent Application WO 00/47212 (within Example 241 thereof).

[24] 7-(N-tert-Butoxycarbonylpiperidin-4-ylmethoxy)-4-chloro-6-methoxyquinazoline was used as the appropriate 4-chloroquinazoline, isopropanol was used in place of pentan-2-ol as the reaction solvent, a 6M solution of hydrogen chloride in isopropanol (0.02 ml) was added and the reaction mixture was heated to 80° C. for 1 hour. The product was obtained as the monohydrochloride salt and gave the following characterising data; NMR Spectrum: (DMSOd$_6$ and CF$_3$CO$_2$D) 1.5–1.65 (m, 2H), 2.0 (d, 2H), 2.15–2.3 (m, 1H), 2.95 (m, 2H), 3.3–3.4 (m, 2H), 4.02 (s, 3H), 4.1 (d, 2H), 6.07 (s, 2H), 7.0 (s, 3H), 7.4 (s, 1H), 8.25 (s, 1H), 8.65 (m, 1H), 8.8 (s, 1H), 8.95 (m, 1H); Mass Spectrum: M + H$^+$ 409. The 7-(N-tert-butoxycarbonylpiperidin-4-ylmethoxy)-4-chloro-6-methoxyquinazoline used as a starting material was prepared as follows:-

Sodium hydride (60% suspension in mineral oil, 1.44 g) was added portionwise during 20 minutes to a solution of 7-benzyloxy-6-methoxy-3,4-dihydroquinazolin-4-one (International Patent Application WO 97/22596, Example 1 thereof; 8.46 g) in DMF (70 ml). The mixture was stirred at ambient temperature for 1.5 hours. Chloromethyl pivalate (5.65 g) was added dropwise and the mixture was stirred at ambient temperature for 2 hours. The mixture was diluted with ethyl acetate (100 ml) and poured onto a mixture (400 ml) of ice and water containing 2N aqueous hydrochloric acid (4 ml). The organic layer was separated and the aqueous layer was extracted with ethyl acetate. The combined extracts were washed with brine, dried over magnesium sulphate and evaporated. The residue was triturated under a mixture of diethyl ether and petroleum ether (b.p. 60–80° C.) and the resultant solid was collected and dried under vacuum. There was thus obtained 7-benzyloxy-6-methoxy-3-pivaloyloxymethyl-3,4-dihydroquinazolin-4-one (10 g); NMR Spectrum: (DMSOd$_6$) 1.11 (s, 9H), 3.89 (s, 3H), 5.3 (s, 2H), 5.9 (s, 2H), 7.27 (s, 1H), 7.35 (m, 1H), 7.47 (t, 2H), 7.49 (d, 2H), 7.51 (s, 1H), 8.34 (s, 1H). A mixture of a portion (7 g) of the material so obtained, 10% palladium-on-charcoal catalyst (0.7 g), DMF (50 ml), methanol (50 ml), acetic acid (0.7 ml) and ethyl acetate (250 ml) was stirred under an atmosphere pressure of hydrogen for 40 minutes. The catalyst was removed by filtration and the solvent was evaporated. The residue was triturated under diethyl ether and the resultant solid was collected and dried under vacuum. There was thus obtained 7-hydroxy-6-methoxy-3-pivaloyloxy-methyl-3,4-dihydroquinazolin-4-one (4.36 g); NMR Spectrum: (DMSOd$_6$) 1.1 (s, 9H), 3.89 (s, 3H), 5.89 (s, 2H), 7.0 (s, 1H), 7.48 (s, 1H), 8.5 (s, 1H). A mixture of 7-hydroxy-6-methoxy-3-pivaloyloxymethyl-3,4-dihydro-quinazolin-4-one (4 g), N-tert-butoxycarbonyl-4-(4-toluenesulphonyloxy-methyl)piperidine (10 g), potassium carbonate (7 g) in DMF (50 ml) and the resultant mixture was stirred and heated to 95° C. for 2.5 hours. The mixture was cooled to ambient temperature and partitioned between water and a mixture of ethyl acetate and diethyl ether. The organic layer was washed in turn with water and brine, dried over magnesium sulphate and evaporated. The resulting oil was crystallised from petroleum ether (b.p. 60–80° C.) and the suspension

TABLE I-continued was stored overnight at 5° C. The resultant solid was collected by filtration, washed with petroleum ether and dried under vacuum. There was thus obtained 7-(N-tert-butoxy-carbonylpiperidin-4-ylmethoxy)-6-methoxy-3-pivaloyloxymethyl-3,4-dihydroquinazolin-4-one which was used without further purification. A mixture of 7-(N-tert-butoxycarbonylpiperidin-4-ylmethoxy)-6-methoxy-3-pivaloyloxymethyl-3,4-dihydroquinazolin-4-one (6 g) and a saturated methanolic ammonia solution (100 ml) was stirred at ambient temperature for 16 hours. The resultant mixture was evaporated and the residue was triturated under diethyl ether. The solid so obtained was isolated, washed with a 49:1 mixture of diethyl ether and methylene chloride and dried under vacuum. There was thus obtained 7-(N-tert-butoxycarbonylpiperidin-4-ylmethoxy)-6-methoxy-3,4-dihydroquinazolin-4-one (3.3 g); NMR Spectrum: (DMSOd$_6$) 1.12–1.3 (m, 2H), 1.42 (s, 9H), 1.8 (d, 2H), 2.02 (m, 1H), 2.7–2.9 (m, 2H), 3.9 (s, 3H), 4.02 (m, 4H), 7.15 (s, 1H), 7.45 (s, 1H), 8.0 (s, 1H). A mixture of a portion (0.2 g) of the material so obtained, carbon tetrachloride (0.15 ml), triphenylphosphine (0.25 g) and 1,2-dichloroethane (10 ml) was stirred and heated to 70° C. for 2 hours. The mixture was evaporated and the residue was purified by column chromatography on silica using a 5:4:1 mixture of methylene chloride, ethyl acetate and methanol as eluent. There was thus obtained 7-(N-tert-butoxycarbonylpiperidin-4-ylmethoxy)-4-chloro-6-methoxyquinazoline (0.07 g); NMR Spectrum: (DMSOd$_6$) 1.15–1.3 (m, 2H), 1.45 (s, 9H), 1.8 (d, 2H), 2.08 (m, 1H), 2.7–2.9 (m, 2H), 4.02 (m, 5H), 4.12 (d, 2H), 7.42 (s, 1H), 7.5 (s, 1H), 8.9 (s, 1H); Mass Spectrum: M + H$^+$ 408. The N-tert-butoxycarbonyl-4-(4-toluenesulphonyloxymethyl)piperidine used as a starting material was prepared as follows:-

A solution of di-tert-butyl dicarbonate (41.7 g) in ethyl acetate (75 ml) was added dropwise to a stirred solution of ethyl piperidine-4-carboxylate (30 g) in ethyl acetate (150 ml) which had been cooled to 0 to 5° C. in an ice-bath. The resultant mixture was stirred at ambient temperature for 48 hours. The mixture was poured into water (300 ml). The organic layer was separated, washed in turn with water (200 ml), 0.1N aqueous hydrochloric acid solution (200 ml), a saturated aqueous sodium bicarbonate solution (200 ml) and brine (200 ml), dried over magnesium sulphate and evaporated. There was thus obtained ethyl N-tert-butoxy-carbonylpiperidine-4-carboxylate (48 g); NMR Spectrum: (CDCl$_3$) 1.25 (t, 3H), 1.45 (s, 9H), 1.55–1.7 (m, 2H), 1.8–2.0 (m, 2H), 2.35–2.5 (m, 1H), 2.7–2.95 (m, 2H), 3.9–4.1 (br s, 2H), 4.15 (q, 2H). A solution of the material so obtained in THF (180 ml) was cooled at 0° C. and lithium aluminium hydride (1M solution in THF; 133 ml) was added dropwise. The mixture was stirred at 0° C. for 2 hours. Water (30 ml) and 2N aqueous sodium hydroxide solution (10 ml) were added in turn and the mixture was stirred for 15 minutes. The resultant mixture was filtered through diatomaceous earth and the solids were washed with ethyl acetate. The filtrate was washed in turn with water and with brine, dried over magnesium sulphate and evaporated. There was thus obtained N-tert-butoxycarbonyl-4-hydroxymethylpiperidine (36.3 g); NMR Spectrum: (CDCl$_3$) 1.05–1.2 (m, 2H), 1.35–1.55 (m, 10H), 1.6–1.8 (m, 2H), 2.6–2.8 (t, 2H), 3.4–3.6 (t, 2H), 4.0–4.2 (br s, 2H). 1,4-Diazabicyclo[2.2.2]octane (42.4 g) was added to a solution of N-tert-butoxycarbonyl-4-hydroxymethylpiperidine (52.5 g) in tert-butyl methyl ether (525 ml) and the mixture was stirred at ambient temperature for 15 minutes. The mixture was then cooled in an ice-bath to 5° C. and a solution of 4-toluenesulphonyl chloride (62.8 g) in tert-butyl methyl ether (525 ml) was added dropwise over 2 hours while maintaining the reaction temperature at approximately 0° C.. The resultant mixture was allowed to warm to ambient temperature and was stirred for 1 hour. Petroleum ether (b.p. 60–80° C., 1L) was added and the precipitate was removed by filtration. The filtrate was evaporated to give a solid residue which was dissolved in diethyl ether. The organic solution was washed in turn with 0.5N aqueous hydrochloric acid solution, water, a saturated aqueous sodium bicarbonate solution and brine, dried over magnesium sulphate and evaporated. There was thus obtained N-tert-butoxycarbonyl-4-(4-toluenesulphonyloxymethyl) piperidine (76.7 g); NMR Spectrum: (CDCl$_3$) 1.0–1.2 (m, 2H), 1.45 (s, 9H), 1.65 (d, 2H), 1.75–1.9 (m, 2H), 2.45 (s, 3H), 2.55–2.75 (m, 2H), 3.85 (d, 1H), 4.0–4.2 (br s, 2H), 7.35 (d, 2H), 7.8 (d, 2H).

[25] 7-[2-(N-tert-Butoxycarbonylpiperidin-4-yl)ethoxy]-4-chloro-6-methoxy-quinazoline was used as the appropriate 4-chloroquinazoline, isopropanol was used in place of pentan-2-ol as the reaction solvent, a 6M solution of hydrogen chloride in isopropanol (0.02 ml) was added and the reaction mixture was heated to 80° C. for 1 hour. The product was obtained as the monohydrochloride salt and gave the following characterising data; NMR Spectrum: (DMSOd$_6$ and CF$_3$CO$_2$D) 1.4–1.55 (m, 2H), 1.9 (br s, 2H), 1.95 (d, 2H), 2.95 (m, 3H), 3.4 (d, 2H), 4.1 (s, 3H), 4.35 (m, 2H), 6.15 (s, 2H), 7.0 (s, 3H), 7.4 (s, 1H), 8.15 (s, 1H), 8.9 (s, 1H); Mass Spectrum: M + H$^+$ 423. The 7-[2-(N-tert-butoxycarbonylpiperidin-4-yl)ethoxy]-4-chloro-6-methoxyquinazoline used as a starting material was obtained as follows:-

A mixture of 7-hydroxy-6-methoxy-3-pivaloyloxymethyl-3,4-dihydroquinazolin-4-one (2 g), N-tert-butoxycarbonyl-4-[2-(4-toluene-sulphonyloxy)ethyl]piperidine (2.84 g), potassium carbonate (1.8 g) and DMF (20 ml) was stirred and heated to 95° C. for 2.5 hours. The resultant mixture was cooled to ambient temperature and poured onto a mixture of ice and water. The mixture was extracted with methylene chloride. The organic layer was washed with brine, dried over magnesium sulphate and evaporated. There was thus obtained 7-[2-(N-tert-butoxy-carbonylpiperidin-4-yl)ethoxy]-6-methoxy-3-pivaloyloxymethyl-3,4-dihydroquinazolin-4-one (2 g); NMR Spectrum: (DMSOd$_6$) 1.0–1.15 (m, 2H), 1.15 (s, 9H), 1.4 (s, 9H), 1.6–1.8 (m, 3H), 2.6–2.8 (m, 2H), 3.92 (s, 3H), 3.9–4.0 (m, 2H), 4.2 (m, 2H), 5.92 (s, 2H), 7.2 (s, 1H), 7.5 (s, 1H), 8.3 (s, 1H). A mixture of 7-[2-(N-tert-butoxycarbonylpiperidin-4-yl)ethoxy]-6-methoxy-3-pivaloyloxymethyl-3,4-dihydroquinazolin-4-one (2 g) and a saturated methanolic ammonia solution (30 ml) was stirred at ambient temperature for 16 hours. The resultant mixture was evaporated and the residue was triturated under diethyl ether. The solid so obtained was isolated, washed with a 49:1 mixture of diethyl ether and methylene chloride and dried under vacuum. There was thus obtained 7-[2-(N-tert-butoxycarbonylpiperidin-4-yl)ethoxy]-6-methoxy-3,4-dihydroquinazolin-4-one (1.3 g); NMR Spectrum: (DMSOd$_6$) 1.0–1.15 (m, 2H), 1.4 (s, 9H), 1.6–1.8 (m, 3H), 2.6–2.8 (m, 2H), 3.3-3.5 (m, 2H), 3.9 (s, 3H), 3.9–4.0 (m, 2H), 4.18 (m, 2H), 7.15 (s, 1H), 7.45 (s, 1H), 8.0 (s, 1H); Mass Spectrum: M + H$^+$ 404. Using an analogous procedure to that described in the last paragraph of the portion of Note [24] immediately above that is concerned with the preparation of 7-N-tert-butoxycarbonylpiperidin-4-ylmethoxy)-4-chloro-6-methoxyquinazoline, 7-[2-(N-tert-butoxycarbonylpiperidin-4-yl)ethoxy]-6-methoxy-3,4- dihydroquinazolin-4-one (0.2 g) was reacted with carbon tetrachloride and triphenylphosphine to give 7-[2-(N-tert-butoxycarbonylpiperidin-4-yl)ethoxy]-4-chloro-6-methoxyquinazoline (0.03 g); NMR Spectrum: (DMSOd$_6$) 1.0–1.2 (m, 2H), 1.4 (s, 9H), 1.6–1.8 (m, 5H), 2.6–2.8 (m, 2H), 3.92 (d, 2H), 4.0 (s, 3H), 4.3 (m, 2H), 7.4 (s, 1H), 7.5 (s, 1H), 8.9 (s, 1H). The N-tert-butoxycarbonyl-4-[2-(4-toluenesulphonyloxy)ethyl]piperidine used as a starting material was prepared by the reaction of 4-toluene-sulphonyl chloride with N-tert-butoxycarbonyl-4-(2-hydroxyethyl)-piperidine (International Patent Application WO 00/47212, in example 126 thereof) using an analogous procedure to that described in the last paragraph of the portion of Note [24] immediately above that is concerned with the preparation of N-tert-butoxycarbonyl-4-(4-toluene-sulphonyloxymethyl)piperidine.

[26] Isopropanol was used in place of pentan-2-ol as the reaction solvent, a 6M solution of hydrogen chloride in isopropanol was added and the reaction mixture was heated to 80° C. for 3 hours. The reaction mixture was evaporated and the residue was purified by column chromatography on silica using increasingly polar mixture of methylene chloride and a saturated methanolic ammonia solution as eluent. The material so obtained was dissolved in diethyl ether and a 3M solution of hydrogen chloride in diethyl ether was added. The precipitate was isolated and dried. The resultant product was obtained as the monohydrochloride salt and gave the following characterising data; NMR Spectrum: (DMSOd$_6$ and CF$_3$CO$_2$D) 1.7–1.9 (m, 2H), 2.15 (d, 2H), 2.37 (m, 1H), 3.1–3.35 (m, 6H), 3.6–3.7 (m, 6H), 3.8 (m, 4H), 4.05 (s, 3H), 4.2 (br s, 2H), 6.1 (s, 2H), 7.02 (s, 3H), 7.4 (s, 1H), 8.15 (s, 1H), 8.9 (s, 1H); Mass Spectrum: M + H$^+$ 522. The 4-chloro-6-methoxy-7- [N-(2-morpholinoethyl)piperidin-4-ylmethoxy] quinazoline used as a starting material was prepared as follows:-

A mixture of 7-(N-t-butoxycarbonylpiperidin-4-ylmethoxy)-6-methoxy-3-pivaloyloxymethyl-3,4-dihydroquinazolin-4-one (12 g), trifluoroacetic acid (25 ml) and methylene chloride (100 ml) was stirred at ambient temperature for 1.5 hours. The mixture was evaporated and the residue was partitioned between methylene chloride and a dilute aqueous sodium bicarbonate solution. The organic layer was washed with water and with brine, dried over magnesium sulphate and evaporated. The residue was triturated under a mixture of diethyl ether and pentane. The resultant solid was isolated and dried under vacuum. There was thus obtained 6-methoxy-7-piperidin-4-ylmethoxy-3-pivaloyloxymethyl-3,4-dihydroquinazolin-4-one (9.1 g); NMR Spectrum: (DMSOd$_6$) 1.15 (s, 9H), 1.2–1.35 (m, 2H), 1.78 (m, 2H, 1.95 (m, 1H), 2.6 (m, 2H), 3.05 (d, 2H, 3.9 (s, 3H), 4.0 (d, 2H, 5.92 (s, 2H, 7.14 (s, 1H), 7.5 (s, 1H), 8.34 (s, 1H); Mass Spectrum: M + H$^+$ 404. A mixture of a portion (1 g) of the material so obtained, 2-morpholinoethyl chloride hydrochloride salt (0.55 g), potassium iodide (0.21 g), sodium bicarbonate (0.625 g) and methanol (23 ml) was stirred and heated to reflux for 2.5 hours. The mixture was evaporated and the residue was partitioned between methylene chloride and water. The organic layer was washed with water and with brine, dried over magnesium sulphate and evaporated. The residue was purified by column chromatography on silica using a 9:1 mixture of methylene chloride and a saturated methanolic ammonia solution as eluent. The residue was triturated under a mixture of diethyl ether and pentane. The resultant solid was isolated and dried under

TABLE I-continued vacuum. There was thus obtained 6-methoxy-7-[N-(2-morpholinoethyl)piperidin-4-ylmethoxy]-3-pivaloyloxymethyl-3,4-dihydroquinazolin-4-one (0.42 g); NMR Spectrum: (DMSOd$_6$) 1.15 (s, 9H), 1.25–1.4 (m, 2H), 1.7–1.9 (m, 3H), 1.9–2.1 (m, 2H), 2.4 (m, 8H), 2.95. (br s, 2H), 3.58 (m, 4H), 3.9 (s, 3H), 4.01 (d, 2H), 5.9 (s, 2H), 7.18 (s, 1H), 7.5 (s, 1H), 8.38 (s, 1H); Mass Spectrum: M − H⁻ 517. A mixture of the material so obtained and a saturated methanolic ammonia solution (10 ml) was stirred at ambient temperature for 16 hours. The mixture was evaporated and the residue was triturated under a 4:1 mixture of diethyl ether and methylene chloride. The resultant solid was isolated, washed with diethyl ether and dried under vacuum. There was thus obtained 6-methoxy-7-[N-(2-morpholinoethyl)piperidin-4- ylmethoxy]-3,4-dihydroquinazolin-4-one (0.29 g); NMR Spectrum: (DMSOd$_6$) 1.25–1.4 (m, 2H), 1.7–1.85 (m, 3H), 1.9–2.1 (m, 2H), 2.4 (d, 8H), 2.92 (br s, 2H), 3.55 (m, 4H), 3.88 (s, 3H), 3.98 (d, 2H), 7.1 (s, 1H), 7.45 (s, 1H), 7.98 (s, 1H); Mass Spectrum: M + H⁺ 403. A mixture of the material so obtained, thionyl chloride (5 ml) and DMF (0.05 ml) was heated to reflux for 1.5 hours. The mixture was evaporated, toluene was added and the mixture was evaporated. The residue was partitioned between methylene chloride and a cooled 2N aqueous sodium hydroxide solution. The organic layer was separated, washed with water and with brine, dried over magnesium sulphate and evaporated. There was thus obtained 4-chloro-6-methoxy-7-[N-(2-morpholinoethyl)-piperidin-4-ylmethoxy]quinazoline (0.115 g); NMR Spectrum: (DMSOd$_6$) 1.25–1.4 (m, 2H), 1.7–1.9 (m, 3H), 1.98 (m, 2H), 2.4 (d, 8H), 2.92 (d, 2H), 3.55 (m, 4H), 4.02 (s, 3H), 4.1 (d, 2H), 7.4 (s, 1H),7.45 (s, 1H), 8.88 (s, 1H); Mass Spectrum: M + H⁺ 421 and 423.

EXAMPLE 3

7-hydroxy-6-methoxy-4-(2,3-methylenedioxyanilino)quinazoline

A mixture of 7-benzyloxy-6-methoxy-4-(2,3methylenedioxyanilino)quinazoline hydrochloride (21 g), ammonium formate (30.2 g), 10% palladium-on-charcoal catalyst (4.8 g), water (26 ml) and DMF (350 ml) was stirred at ambient temperature for 2 hours. The mixture was filtered and the filtrate was evaporated. The residual oil was triturated under diethyl ether. The solid so obtained was triturated under water, collected by filtration, washed with water and with diethyl ether and dried under vacuum over phosphorus pentoxide. The material so obtained was purified by column chromatography on silica using a 9:1 mixture of methylene chloride and methanol as eluent. There was thus obtained the title compound (15 g); NMR Spectrum: (DMSOd$_6$) 3.95 (s, 3H), 6.0 (s, 2H), 6.85 (m, 2H), 6.95 (d, 1H), 7.05 (s, 1H), 7.8 (s, 1H), 8.3 (s, 1H), 9.4 (s, 1H), 10.3 (s, 1H); Mass Spectrum: M+H⁺ 312.

EXAMPLE 4

4-(6-chloro-2,3-methylenedioxyanilino)-7-hydroxy-6-methoxyquinazoline

A mixture of 7-benzyloxy-4-(6-chloro-2,3-methylenedioxyanilino)-6-methoxyquinazoline dihydrochloride (3.3 g) and trifluoroacetic acid (60 ml) was heated to reflux for 4 hours. The mixture was evaporated. The residue was diluted with water and methanol and the mixture was basified to pH 7.5 by the addition of a saturated aqueous sodium carbonate solution. The methanol was evaporated and the resultant solid was isolated and washed with water. There was thus obtained the title compound as a solid (2.5 g); NMR Spectrum: (DMSOd$_6$ and CF$_3$CO$_2$D) 3.95 (s, 3H), 6.1 (s, 2H), 6.95 (d, 1H), 7.1 (m, 2H), 8.1 (s, 1H), 8.4 (s, 1H), 9.85 (br s, 1H), 10.7 (br s, 1H); Mass Spectrum: M+H⁺ 346 and 348.

EXAMPLE 5

6-methoxy-4-(2,3-methylenedioxyanilino)-7-(3-methylsulphonylpropoxy)quinazoline monohydrochloride salt Diethyl azodicarboxylate (0.101 ml) was added dropwise to a stirred mixture of 7-hydroxy-6-methoxy-4-(2,3-methylenedioxyanilino)quinazoline (0.1 g), 3-methylsulphonylpropan-1-ol (0.057 g), triphenylphosphine (0.168 g) and methylene chloride (5 ml) and the reaction mixture was stirred at ambient temperature. After a few minutes further portions of triphenylphosphine (0.084 g) and 3-methylsulphonylpropan-1-ol (0.022 g) were added followed by the dropwise addition of diethyl azodicarboxylate (0.050 ml). After another few minutes third portions of the same amounts of these reagents were added. The reaction mixture was evaporated and the residue was purified by column chromatography on silica using a 10:6:1 mixture of methylene chloride, ethyl acetate and methanol as eluent. The material so obtained was triturated under a 6M solution of hydrogen chloride in diethyl ether. There was thus obtained the title compound (0.108 g) as a white solid; NMR Spectrum: (DMSOd$_6$ and CF$_3$CO$_2$D) 2.3 (m, 2H), 3.05 (s, 3H), 3.35 (m, 2H), 4.0 (s, 3H), 4.35 (t, 2H), 6.1 (s, 2H), 7.0 (m, 3H), 7.3 (s, 1H), 8.1 (s, 1H), 8.15 (s, 1H); Mass Spectrum: M+H⁺ 432.

The 3-methylsulphonylpropan-1-ol used as a starting material was obtained as follows:

3-Chloroperoxybenzoic acid (67%, 25 g) was added portionwise to a stirred mixture of 3-methylthiopropan-1-ol (5 ml) and methylene chloride and the resultant mixture was stirred at ambient temperature for 1 hour. The resultant mixture was filtered and the filtrate was evaporated. The residue was purified by column chromatography on alumina using a 19:1 mixture of methylene chloride and methanol as eluent to give the required starting material as an oil (4.18 g); NMR Spectrum: (CDCl$_3$) 2.1 (m, 2H), 2.96 (s, 3H), 3.2 (t, 2H), 3.8 (t, 2H); Mass Spectrum: M+H⁺ 139.

EXAMPLE 6

6,7-di-(2-methoxyethoxy)-4-(2,3-methylenedioxyanilino)quinazoline monohydrochloride salt Using an analogous procedure to that described in Example 1, 4-chloro-6,7-di-(2-methoxyethoxy)quinazoline (U.S. Pat. No. 5,747,498; 0.1 g) was reacted with 2,3-methylenedioxyaniline (0.048 g) to give the title compound (0.121 g); NMR Spectrum: (DMSOd$_6$ and CF$_3$CO$_2$D) 3.5 (s, 6H), 3.8 (m, 4H), 4.35 (m, 4H), 6.05 (s, 2H), 6.95 (m, 3H), 7.4 (s, 1H), 8.2 (s, 1H), 8.85 (s, 1H); Mass Spectrum: M+H⁺ 414.

EXAMPLE 7

4-(6-chloro-2,3-methylenedioxyanilino)-6-methoxy-7-(2-pyrrolidin-1-ylethoxy)quinazoline Diethyl azodicarboxylate (0.182 ml) was added dropwise to a stirred mixture of 4-(6-chloro-2,3-methylenedioxyanilino)-7-hydroxy-6-methoxyquinazoline (0.2 g), N-(2-hydroxyethyl)pyrrolidine (0.086 g), triphenylphosphine (0.303 g) and methylene chloride (3 ml) and the reaction mixture was stirred at ambient temperature for 15 minutes. The reaction mixture was evaporated and the residue was purified by column chromatography on silica using a 45:4:1 mixture of methylene chloride, methanol and a saturated methanolic ammonia solution as eluent. There was thus obtained the title compound (0.033 g) as a white solid; NMR Spectrum: (DMSOd$_6$ and CF$_3$CO$_2$D) 1.9 (m, 2H), 2.1 (m, 2H), 3.2 (m, 2H), 3.7 (m, 2H), 3.8 (m, 2H), 4.05 (s, 3H), 4.6 (m, 2H), 6.2 (s, 2H), 7.1 (d, 1H), 7.5 (s, 1H), 8.2 (s, 1H), 8.95 (s, 1H); Mass Spectrum: M−H$^-$ 441 and 443.

EXAMPLE 8

Using an analogous procedure to that described in Example 7, the appropriate 7-hydroxyquinazoline was reacted with the appropriate alcohol to give the compounds described in Table II. Unless otherwise stated, each compound described in Table II was obtained as the free base.

TABLE II

| Compound No. & Note | R$^1$ | R$^2$ |
|---|---|---|
| [1] | 3-diisopropylaminopropoxy | hydrogen |
| [2] | 3-(1,1-dioxotetrahydro-4H-1,4-thiazin-4-yl)propoxy | 6-chloro |
| [3] | 3-piperidinopropoxy | 6-chloro |
| [4] | 3-methylsulphonylpropoxy | 6-chloro |
| [5] | 3-diisopropylaminopropoxy | 6-chloro |
| [6] | 2-(4-methylpiperazin-1-yl)ethoxy | hydrogen |
| [7] | 2-piperidinoethoxy | 6-chloro |
| [8] | 2-(4-methylpiperazin-1-yl)ethoxy | 6-chloro |
| [9] | 2-pyrrol-1-ylethoxy | 6-chloro |
| [10] | 2-(2-oxopyrrolidin-1-yl)ethoxy | 6-chloro |
| [11] | 2-(4-pyridyloxy)ethoxy | 6-chloro |
| [12] | 3-(4-pyridyloxy)propoxy | 6-chloro |
| [13] | 3-(4-pyridyloxy)propoxy | hydrogen |
| [14] | 3-(6-methylpyrid-2-yloxy)propoxy | hydrogen |
| [15] | 3-(6-methylpyrid-2-yloxy)propoxy | 6-chloro |
| [16] | 3-(2-pyridyloxy)propoxy | hydrogen |
| [17] | 3-(2-pyridyloxy)propoxy | 6-chloro |
| [18] | 2-(6-chloropyrid-2-yloxy)ethoxy | hydrogen |
| [19] | 2-(6-chloropyrid-2-yloxy)ethoxy | 6-chloro |
| [20] | 2-cyanopyrid-4-ylmethoxy | 6-chloro |
| [21] | 2-cyanopyrid-4-ylmethoxy | hydrogen |
| [22] | 2-(N-tert-butoxycarbonyl-4-hydroxypiperidin-4-yl)ethoxy | hydrogen |
| [23] | 2-(4-hydroxytetrahydropyran-4-yl)ethoxy | hydrogen |
| [24] | 2-(4-hydroxytetrahydropyran-4-yl)ethoxy | 6-chloro |
| [25] | ethoxy | hydrogen |
| [26] | 3-(4-tert-butoxycarbonylpiperazin-1-yl)propoxy | 6-chloro |
| [27] | 3-(4-tert-butoxycarbonylpiperazin-1-yl)propoxy | hydrogen |
| [28] | 2-(4-pyridyloxy)ethoxy | hydrogen |
| [29] | N-tert-butoxycarbonylpiperidin-4-ylmethoxy | 6-chloro |
| [30] | 3-(cis-4-cyanomethyl-3,5-dimethylpiperazin-1-yl)propoxy | hydrogen |
| [31] | 3-(cis-3,5-dimethylpiperazin-1-yl)propoxy | hydrogen |
| [32] | 3-(4-mesylpiperazin-1-yl)propoxy | 6-chloro |
| [33] | 3-[4-(2-cyanoethyl)piperazin-1-yl]propoxy | 6-chloro |
| [34] | 3-(4-isobutyrylpiperazin-1-yl)propoxy | 6-chloro |

Notes

[1] The product gave the following characterising data; NMR Spectrum: (DMSOd$_6$ and CF$_3$CO$_2$D) 1.3 (m, 12H), 2.25 (m, 2H), 3.4 (m, 2H), 3.8 (m, 2H), 4.0 (s, 3H), 4.3 (t, 2H), 6.1 (s, 2H), 7.0 (m, 3H), 7.35 (s, 1H), 8.1 (s, 1H), 8.9 (s, 1H); Mass Spectrum: M + H$^+$ 453.
The 3-diisopropylaminopropan-1-ol used as a starting material was prepared as described in Tet. Lett., 1994, 35, 761.

[2] The product gave the following characterising data; NMR Spectrum: (DMSOd$_6$ and CF$_3$CO$_2$D) 2.35 (m, 2H), 3.5 (m, 2H), 3.65 (m, 4H), 3.85 (m, 4H), 4.05 (s, 3H), 4.35 (m, 2H), 6.15 (s, 2H), 7.05 (d, 1H), 7.15 (d, 1H), 7.4 (s, 1H), 8.15 (s, 1H), 8.9 (s, 1H); Mass Spectrum: M + H$^+$ 521 and 523.

[3] The product gave the following characterising data; NMR Spectrum: (DMSOd$_6$ and CF$_3$CO$_2$D) 1.4 (m, 1H), 1.7 (m, 3H), 1.85 (m, 2H), 2.3 (m, 2H), 2.95 (m, 2H), 3.3 (m, 2H), 3.55 (m, 2H), 4.05 (s, 3H), 4.3 (m, 2H), 6.15 (s, 2H), 7.05 (d, 1H), 7.15 (d, 1H), 7.4 (s, 1H), 8.15 (s, 1H), 8.95 (s, 1H); Mass Spectrum: M + H$^+$ 471 and 473.

[4] The product gave the following characterising data; NMR Spectrum: (DMSOd$_6$ and CF$_3$CO$_2$D) 2.3 (m, 2H), 3.05 (s, 3H), 3.35 (m, 2H), 4.05 (s, 3H), 4.35 (m, 2H), 6.15 (s, 2H), 7.05 (d, 1H), 7.15 (d, 1H), 7.35 (s, 1H), 8.15 (s, 1H), 8.9 (s, 1H); Mass Spectrum: M + H$^+$ 466 and 468.

[5] The product gave the following characterising data; NMR Spectrum: (DMSOd$_6$) 0.95 (d, 12H), 1.85 (m, 2H), 2.6 (m, 2H), 3.0 (m, 2H), 3.95 (s, 3H), 4.15 (m, 2H), 6.1 (s, 2H), 6.95 (d, 1H), 7.05 (d, 1H), 7.15 (s, 1H), 7.8 (s, 1H), 8.3 (s, 1H), 9.45 (s, 1H); Mass Spectrum: M − H$^-$ 485 and 487.

[6] The product gave the following characterising data; NMR Spectrum: (DMSOd$_6$ and CF$_3$CO$_2$D) 2.9 (s, 3H), 3.3–3.9 (br s, 8H), 3.8 (m, 2H), 4.0 (s, 3H), 4.6 (m, 2H), 6.1 (s, 2H), 7.0 (m, 3H), 7.45 (s, 1H), 8.15 (s, 1H), 8.9 (s, 1H); Mass Spectrum: M + H$^+$ 438; Elemental Analysis: Found C, 61.75; H, 6.24; N, 15.6; C$_{23}$H$_{27}$N$_5$O$_4$ 0.5H$_2$O requires C, 61.87; H, 6.32; N, 15.68%.
The 1-(2-hydroxyethyl)-4-methylpiperazine used as a starting material was prepared as follows:-
A mixture of 2-bromoethanol (2.36 g), N-methylpiperazine (1.26 g), potassium carbonate (5.0 g) and ethanol (150 ml) was stirred and heated to reflux for 18 hours. The mixture was cooled to ambient temperature and filtered. The filtrate was evaporated and the residue was triturated under a mixture of methylene chloride and acetone. The resultant mixture was filtered and the filtrate was evaporated to give the required starting material as an oil (0.87 g); NMR Spectrum: (CDCl$_3$) 2.18 (s, 3H), 2.3–2.7 (br m, 8H), 2.56 (t, 2H), 3.61 (t, 2H).

[7] The product gave the following characterising data; NMR Spectrum: (DMSOd$_6$ and CF$_3$CO$_2$D) 1.4 (m, 1H), 1.7 (m, 3H), 1.85 (m, 2H), 3.1 (m, 2H), 3.6 (m, 2H), 3.7 (m, 2H), 4.05 (s, 3H), 4.6 (m, 2H), 6.15 (s, 2H), 7.05 (d, 1H), 7.15 (d, 1H), 7.45 (s, 1H), 8.15 (s, 1H), 8.95 (s, 1H); Mass Spectrum: M + H$^+$ 455 and 457.

[8] The product gave the following characterising data; NMR Spectrum: (DMSOd$_6$ and CF$_3$CO$_2$D) 2.9 (s, 3H), 3.3–3.9 (br s, 8H), 3.75 (m, 2H), 4.05 (s, 3H), 4.6 (m, 2H), 6.15 (s, 2H), 7.05 (d, 1H), 7.15 (d, 1H), 7.5 (s, 1H), 8.2 (s, 1H), 8.9 (s, 1H); Mass Spectrum: M + H$^+$ 472 and 474.

[9] The product gave the following characterising data; NMR Spectrum: (DMSOd$_6$ and CF$_3$CO$_2$D) 4.05 (s, 3H), 4.4 (m, 2H), 4.5 (m, 2H), 6.05 (d, 2H), 6.15 (s, 2H), 6.9 (d, 2H), 7.05 (d, 1H), 7.15 (d, 1H), 7.3 (s, 1H), 8.15 (s, 1H), 8.9 (s, 1H); Mass Spectrum: M + H$^+$ 439 and 441.
The 2-pyrrol-1-ylethanol was prepared as a starting material using an analogous procedure to that described in J.C.S. Chem. Comm., 1974, 931.

[10] The product gave the following characterising data; NMR Spectrum: (DMSOd$_6$ and CF$_3$CO$_2$D) 1.95 (m, 2H), 2.25 (t, 2H), 3.5 (t, 2H), 3.65 (t, 2H), 3.95 (s, 3H), 4.25 (t, 2H), 6.1 (s, 2H), 6.95 (d, 1H), 7.05 (d, 1H), 7.2 (s, 1H), 7.85 (s, 1H), 8.3 (s, 1H), 9.45 (s, 1H); Mass Spectrum: M + H$^+$ 457 and 459.

[11] The product gave the following characterising data; NMR Spectrum: (DMSOd$_6$) 3.95 (s, 3H), 4.5 (m, 4H), 6.05 (s, 2H), 6.95 (d, 1H), 7.05 (m, 3H), 7.25 (s, 1H), 7.85 (s, 1H), 8.35 (s, 1H), 8.4 (d, 2H), 9.5 (s, 1H); Mass Spectrum: M + H$^+$ 467 and 469.
The 4-(2-hydroxyethoxy)pyridine used as a starting material was prepared according to the procedure disclosed in J. Chem. Soc. Perkin II, 1987, 1867.

[12] The product gave the following characterising data; NMR Spectrum: (DMSOd$_6$) 2.3 (m, 2H), 3.9 (s, 3H), 4.3 (m, 4H), 6.05 (s, 2H), 6.95 (d, 1H), 7.0 (d, 2H), 7.05 (d, 1H), 7.25 (s, 1H), 7.85 (s, 1H), 8.3 (s, 1H), 8.4 (d, 2H), 9.45 (s, 1H); Mass Spectrum: M + H$^+$ 481 and 483.
The 4-(3-hydroxypropoxy)pyridine used as a starting material was prepared as follows:-
Sodium hydroxide (6.66 g) was added to a mixture of 4-chloropyridine hydrochloride (10 g), 1,3-propanediol (24 ml) and DMSO (100 ml) and the mixture was stirred and heated to 100° C. for 20 hours. The mixture was concentrated by evaporation under vacuum of DMSO (about 80 ml) and the residual mixture was diluted with ice-water and extracted with ethyl acetate (4×). The organic phases were combined, dried over magnesium sulphate and evaporated. The residue was purified by column chromatography on silica using a 12:7:1 mixture of methylene chloride, ethyl acetate and methanol as eluent. There was thus obtained

TABLE II-continued 4-(3-hydroxypropoxy)pyridine (3.13 g) as an oil; NMR Spectrum: (CDCl$_3$) 2.05 (m, 2H), 3.0 (br s, 1H), 3.85 (m, 2H), 4.15 (t, 2H), 6.75 (d, 2H), 8.35 (d, 2H); Mass Spectrum: M + H$^+$ 154.

[13] DMF was used in place of methylene chloride as the reaction solvent. The product gave the following characterising data; NMR Spectrum: (DMSOd$_6$) 2.3 (m, 2H), 3.95 (s, 3H), 4.3 (m, 4H), 6.05 (s, 2H), 6.85 (m, 2H), 6.95 (d, 1H), 7.05 (d, 2H), 7.2 (s, 1H), 7.8 (s, 1H), 8.35 (s, 1H), 8.4 (d, 2H), 9.5 (s, 1H); Mass Spectrum: M − H$^−$ 445.

[14] The product gave the following characterising data; NMR Spectrum: (DMSOd$_6$) 2.25 (m, 2H), 2.4 (s, 3H), 3.95 (s, 3H), 4.3 (t, 2H), 4.45 (t, 2H), 6.1 (s, 2H), 6.65 (d, 1H), 6.85 (m, 3H), 6.95 (d, 1H), 7.2 (s, 1H), 7.6 (t, 1H), 7.85 (s, 1H), 8.35 (s, 1H), 9.5 (s, 1H); Mass Spectrum: M + H$^+$ 461.

The 2-(3-hydroxypropoxy)-6-methylpyridine used as a starting material was prepared as follows:-
Sodium hydroxide (3 g) was added to a mixture of 6-chloro-2-methylpyridine (3.3 ml), 1,3-propanediol (11 ml) and DMSO (35 ml) and the mixture was stirred and heated to 100° C. for 20 hours. The mixture was cooled to ambient temperature, diluted with ice-water and extracted with ethyl acetate (3×). The organic phases were combined, dried over magnesium sulphate and evaporated. The residue was purified by column chromatography on silica using a 4:1 mixture of methylene chloride and ethyl acetate as eluent. There was thus obtained 2-(3-hydroxypropoxy)-6-methylpyridine (3.5 g) as an oil; NMR Spectrum: (CDCl$_3$) 1.95 (m, 2H), 2.45 (s, 3H), 3.7 (m, 2H), 4.1 (br s, 1H), 4.5 (t, 2H), 6.55 (d, 1H), 6.75 (d, 1H), 7.45 (t, 1H).

[15] The product gave the following characterising data; NMR Spectrum: (DMSOd$_6$) 2.25 (m, 2H), 2.4 (s, 3H), 3.95 (s, 3H), 4.3 (t, 2H), 4.45 (t, 2H), 6.1 (s, 2H), 6.65 (d, 1H), 6.85 (d, 1H), 6.95 (d, 1H), 7.1 (d, 1H), 7.25 (s, 1H), 7.6 (t, 1H), 7.85 (s, 1H), 8.35 (s, 1H), 9.5 (s, 1H); Mass Spectrum: M + H$^+$ 495 and 497.

[16] DMF was used in place of methylene chloride as the reaction solvent. The product gave the following characterising data; NMR Spectrum: (DMSOd$_6$) 2.2 (m, 2H), 3.95 (s, 3H), 4.1 (t, 2H), 4.2 (t, 2H), 6.05 (s, 2H), 6.2 (t, 1H), 6.4 (d, 1H), 6.9 (m, 2H), 6.95 (d, 1H), 7.15 (s, 1H), 7.4 (m, 1H), 7.7 (d, 1H), 7.85 (s, 1H), 8.4 (s, 1H), 9.6 (s, 1H); Mass Spectrum: M + H$^+$ 447.

The 2-(3-hydroxypropoxy)pyridine used as a starting material was prepared by the reaction of 2-chloropyridine and 1,3-propanediol using an analogous procedure to that described in Note [14] immediately above.

[17] DMF was used in place of methylene chloride as the reaction solvent. The product gave the following characterising data; NMR Spectrum: (DMSOd$_6$) 2.2 (m, 2H), 3.95 (s, 3H), 4.1 (t, 2H), 4.2 (t, 2H), 6.1 (s, 2H), 6.2 (t, 1H), 6.4 (d, 1H), 6.95 (d, 1H), 7.1 (d, 1H), 7.2 (s, 1H), 7.4 (m, 1H), 7.65 (d, 1H), 7.85 (s, 1H), 8.35 (s, 1H), 9.5 (s, 1H); Mass Spectrum: M + H$^+$ 481 and 483.

[18] DMF was used in place of methylene chloride as the reaction solvent. The reaction product was purified by column chromatography on silica ([Isolute SCX column) using an 18:1 mixture of methylene chloride and a saturated methanolic ammonia solution as eluent. The product so obtained gave the following characterising data; NMR Spectrum: (DMSOd$_6$) 3.95 (s, 3H), 4.5 (m, 2H), 4.65 (m, 2H), 6.05 (s, 2H), 6.9 (m, 4H), 7.15 (d, 1H), 7.25 (s, 1H), 7.8 (m, 1H), 8.4 (s, 1H), 9.5 (s, 1H); Mass Spectrum: M + H$^+$ 467 and 469.

The 6-chloro-2-(2-hydroxyethoxy)pyridine used as a starting material was prepared as follows:-
Sodium hydride (50% dispersion in mineral oil; 0.48 g) was added portionwise to a stirred mixture of 2-tetrahydropyran-2-yloxyethanol (1.36 ml) and DMF (5 ml) and the mixture was stirred at ambient temperature for 30 minutes and then heated to 80° C. for 15 minutes. The mixture was cooled to ambient temperature. 2,6-Dichloropyridine (1.48 g) was added and the resultant mixture was heated to 80° C. for 16 hours. The mixture was cooled to ambient temperature and partitioned between ethyl acetate and water. The organic phase was washed with brine, dried over magnesium sulphate and evaporated. The residue was purified by column chromatography on silica using methylene chloride as eluent. There was thus obtained 2-chloro-6-(2-tetrahydropyran-2-yloxyethoxy)pyridine (2 g) as an oil; NMR Spectrum: (CDCl$_3$) 1.4–1.9 (m, 6H), 3.5 (m, 1H), 3.75 (m, 1H), 3.85 (m, 1H), 4.05 (m, 1H), 4.5 (m, 2H), 4.7 (m, 1H), 6.7 (d, 1H), 6.9 (d, 1H), 7.5 (t, 1H).

A mixture of the material so obtained, acetic acid (20 ml), water (4 ml) and THF (8 ml) was stirred and heated to 80° C. for 5 hours. The solvent was evaporated and the residue was purified by column chromatography on silica using a 3:2 mixture of petroleum ether (b.p. 40–60° C.) and diethyl ether as eluent. There was thus obtained 6-chloro-2-(2-hydroxyethoxy)pyridine (0.98 g) as an oil; NMR Spectrum: (DMSOd$_6$ and CF$_3$CO$_2$D) 2.5 (br s, 1H), 3.9 (m, 2H), 4.45 (m, 2H), 6.7 (d, 1H), 6.9 (d, 1H), 7.5 (t, 1H); Mass Spectrum: M + H$^+$ 174 and 176.

[19] The reaction product was purified by column chromatography on silica (Isolute SCX column) using an 18:1 mixture of methylene chloride and a saturated methanolic ammonia solution as eluent. The product so obtained gave the following characterising data; NMR Spectrum: (DMSOd$_6$) 4.05 (s, 3H), 4.5 (m, 2H), 4.65 (m, 2H), 6.1 (s, 2H), 6.9 (t, 2H), 7.05 (d, 1H), 7.15 (d, 1H), 7.3 (s, 1H), 7.8 (t, 1H), 7.85 (s, 1H), 8.35 (s, 1H), 9.5 (br s, 1H); Mass Spectrum: M + H$^+$ 501 and 503.

[20] The product gave the following characterising data; NMR Spectrum: (DMSOd$_6$ and CF$_3$CO$_2$D) 4.05 (s, 3H), 5.55 (s, 2H), 6.15 (s, 2H), 7.05 (d, 1H), 7.15 (d, 1H), 7.35 (s, 1H), 7.85 (d, 1H), 8.14 (s, 1H), 8.18 (s, 1H), 8.85 (d, 1H), 8.9 (s, 1H); Mass Spectrum: M + H$^+$ 462 and 464.

The 2-cyano-4-hydroxymethylpyridine used as a starting material was prepared as follows:-
Using an analogous procedure to that disclosed in J. Het. Chem., 1993, 30, 631, 4-hydroxymethylpyridine was converted into 4-(tert-butyldimethylsilyloxymethyl)pyridine-2-carbonitrile.

A mixture of the material so obtained (3.37 g) tert-butylammonium fluoride (1M solution in THF; 24 ml) and THF (20 ml) was stirred at ambient temperature for 1 hour. The mixture was evaporated and the residue was partitioned between ethyl acetate and a saturated aqueous ammonium chloride solution. The organic phase was washed with water and with brine, dried over magnesium sulphate and evaporated. The residue was purified by column chromatography on silica using increasingly polar mixtures of petroleum ether (b.p. 40-60° C.) and ethyl acetate as eluent. There was thus obtained 2-cyano-4-hydroxymethyl-pyridine as a solid (1.37 g); NMR Spectrum: (CDCl$_3$) 2.25 (br s, 1H), 4.85 (s, 2H), 7.55 (d, 1H), 7.75 (s, 1H), 8.7 (d, 1H).

[21] DMF was used in place of methylene chloride as the reaction solvent. The product gave the following characterising data; NMR Spectrum: (DMSOd$_6$ and CF$_3$CO$_2$D) 4.0 (s, 3H), 5.45 (s, 2H), 6.0 (s, 2H), 6.85–7.0 (m, 3H), 7.3 (s, 1H), 7.85 (d, 1H), 7.9 (s, 1H), 8.1 (s, 1H), 8.4 (s, 1H), 8.8 (d, 1H); Mass Spectrum: M + H$^+$ 428.

[22] The product gave the following characterising data; NMR Spectrum: (CDCl$_3$) 1.45 (s, 9H), 1.6 (m, 4H), 2.1 (m, 2H), 3.2 (s, 1H), 3.25 (m, 2H), 3.8 (m, 2H), 4.0 (s, 3H), 4.4 (t, 2H), 6.05 (s, 2H), 6.7 (d, 1H), 6.9 (t, 1H), 7.0 (s, 1H), 7.05 (s, 1H), 7.25 (s, 1H), 7.75 (d, 1H), 8.7 (s, 1H); Mass Spectrum: M + H$^+$ 539.

The N-tert-butoxycarbonyl-4-hydroxy-4-(2-hydroxyethyl)piperidine used as a starting material was prepared as follows:-
A mixture of tert-butyl 4-oxopiperidine-1-carboxylate (5 g), ethyl bromoacetate (4.17 ml), zinc powder (2.46 g) and THF (40 ml) was stirred and heated to reflux to initiate reaction. Once the reaction had started, the temperature of the reaction mixture was controlled by the occasional immersion of the mixture in an ice bath. After 2 hours the reaction mixture was evaporated and the residue was partitioned between ethyl acetate and water. The organic phase was washed with brine, dried over magnesium sulphate and evaporated. The residue was purified by column chromatography on silica using a 6:1 mixture of methylene chloride and ethyl acetate as eluent. There was thus obtained tert-butyl 4-ethoxycarbonylmethyl-4-hydroxypiperidine-1-carboxylate as an oil (6.5 g); NMR Spectrum: (CDCl$_3$) 1.3 (t, 3H), 1.45 (s, 9H), 1.5 (m, 2H), 1.7 (m, 2H), 2.5 (s, 2H), 3.2 (m, 2H), 3.6 (s, 1H), 3.85 (br s, 2H), 4.2 (m, 2H).

TABLE II-continued

A solution of the material so obtained in THF (30 ml) was added to a stirred suspension of lithium aluminium hydride (0.86 g) in THF (45 ml) which was cooled in an ice-bath to 0° C.. After completion of the addition, the reaction mixture was heated to reflux for 2 hours. The mixture was cooled to 0° C. and a concentrated (40%) aqueous sodium hydroxide solution was added. The mixture was filtered and the filtrate was concentrated by partial evaporation. The residue was extracted with methylene chloride and the extract was dried over magnesium sulphate and evaporated. There was thus obtained N-tert-butoxycarbonyl-4-hydroxy-4-(2-hydroxyethyl)piperidine as an oil; NMR Spectrum: ($CDCl_3$) 1.45 (s, 9H), 1.5 (m, 2H), 1.7 (m, 2H), 1.75 (m, 2H), 2.2 (br s, 1H), 2.9 (s, 1H), 3.2 (m, 2H), 3.75 (m, 2H), 3.95 (m, 2H).

[23] The product gave the following characterising data; NMR Spectrum: ($DMSOd_6$ and $CF_3CO_2D$) 1.5 (m, 2H), 1.65 (m, 2H), 2.0 (m, 2H), 3.65 (m, 4H), 4.0 (s, 3H), 4.35 (t, 2H), 6.05 (s, 2H), 7.0 (m, 3H), 7.35 (s, 1H), 8.05 (s, 1H), 8.85 (s, 1H); Mass Spectrum: M + $H^+$ 440.

The 4-hydroxy-4-(2-hydroxyethyl)tetrahydropyran used as a starting material was prepared as follows:-

Using analogous procedures to those described in Note [22] immediately above for the conversion of tert-butyl 4-oxopiperidine-1-carboxylate into N-tert-butoxycarbonyl-4-hydroxy-4-(2-hydroxyethyl)piperidine, tetrahydropyran-4-one was reacted with ethyl bromoacetate to give ethyl 2-(4-hydroxytetrahydropyran-4-yl)acetate; NMR Spectrum: ($CDCl_3$) 1.3 (t, 3H), 1.65 (m, 4H), 2.5 (s, 2H), 4.6 (s, 1H), 3.75 (m, 2H), 3.85 (m, 2H), 4.2 (q, 2H); which, in turn, was reduced to give 4-hydroxy-4-(2-hydroxyethyl)tetrahydropyran; NMR Spectrum: ($CDCl_3$) 1.7 (m, 4H), 1.8 (m, 2H), 2.25 (br s, 1H), 2.9 (br s, 1H), 3.8 (m, 4H), 3.95 (m, 2H).

[24] The product gave the following characterising data; NMR Spectrum: ($DMSOd_6$ and $CF_3CO_2D$) 1.5 (m, 2H), 1.65 (m, 2H), 2.0 (m, 2H), 3.6 (m, 4H), 4.0 (m, 5H), 6.15 (s, 2H), 7.05 (d, 1H), 7.15 (d, 1H), 7.35 (s, 1H), 8.1 (s, 1H), 8.9 (s, 1H); Mass Spectrum: M + $H^+$ 474 and 476.

[25] Chloroform was used in place of methylene chloride as the reaction solvent. The product gave the following characterising data; NMR Spectrum: ($DMSOd_6$) 1.45 (t, 3H), 3.95 (s, 3H), 4.2 (q, 2H), 6.05 (s, 2H), 6.9 (m, 2H), 6.95 (d, 1H), 7.15 (s, 1H), 7.8 (s, 1H), 8.35 (s, 1H), 9.5 (s, 1H); Mass Spectrum: M + $H^+$ 340.

[26] The product gave the following characterising data; NMR Spectrum: ($DMSOd_6$ and $CF_3CO_2D$) 1.4 (s, 9H), 2.05 (m, 2H), 2.45 (m, 4H), 2.6 (m, 2H), 3.35 (m, 4H), 3.95 (s, 3H), 4.2 (m, 2H), 6.1 (s, 2H), 6.95 (d, 1H), 7.05 (d, 1H), 7.2 (s, 1H), 7.85 (s, 1H), 8.3 (s, 1H); Mass Spectrum: M + $H^+$ 572 and 574.

The 1-(tert-butoxycarbonyl)-4-(3-hydroxypropyl)piperazine used as a starting material was prepared as follows using an analogous procedure to that described in European Patent Application No. 0388309:-

A mixture of 3-bromopropanol (2 ml), 1-(tert-butoxycarbonyl)piperazine (29 ml), potassium carbonate (83 g) and ethanol (200 ml) was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distillation to give the required starting material as an oil.

[27] The product gave the following characterising data; NMR Spectrum: ($DMSOd_6$) 1.4 (s, 9H), 1.95 (m, 2H), 2.35 (m, 4H), 2.45–2.6 (m, 6H), 3.95 (s, 3H), 4.2 (t, 2H), 6.05 (s, 2H), \ 6.8–7.0 (m, 3H), 7.2 (s, 1H), 7.8 (s, 1H), 8.35 (s, 1H), 9.5 (s, 1H); Mass Spectrum: M + $H^+$ 538.

[28] The free base form of the reaction product was treated with a 6M solution of hydrogen chloride in diethyl ether to give the dihydrocloride salt which gave the following characterising data; NMR Spectrum: ($DMSOd_6$ and $CF_3CO_2D$) 4.0 (s, 3H), 4.68 (br s, 2H), 4.9 (br s, 2H), 6.1 (s, 2H), 7.0 (2s, 2H), 7.5 (s, 1H), 7.7 (d, 2H), 8.2 (s, 1H), 8.85 (d, 2H), 8.9 (s, 1H); Mass Spectrum: M + $H^+$ 433.

[29] DMF was used in place of methylene chloride as the reaction solvent. The product gave the following characterising data; Mass Spectrum: M + $H^+$ 543 and 545.

[30] DMF was used in place of methylene chloride as the reaction solvent and the reaction mixture was stirred at ambient temperature for 16 hours. The product gave the following characterising data; NMR Spectrum: ($DMSOd_6$ and $CF_3CO_2D$) 1.12 (s, 3H), 1.13 (s, 3H), 2.3 (m, 2H), 2.8 (m, 4H), 3.3 (m, 2H), 3.65 (d, 2H), 4.0 (s, 3H), 4.05 (m, 2H), 4.35 (m, 2H), 6.1 (s, 2H), 7.0 (m, 3H), 7.35 (s, 1H), 8.1 (s, 1H), 8.9 (s, 1H); Mass Spectrum: M + $H^+$ 505.

The cis-3,5-dimethyl-4-cyanomethyl-1-(3-hydroxypropyl)piperazine used as a starting material was prepared as follows:-

A mixture of cis-2,6-dimethylpiperazine (4.3 g), 3-bromopropanol (5.2 g), potassium carbonate (15.6 g) and acetonitrile (30 ml) was stirred and heated to 80° C. for 2.5 hours. The mixture was filtered and the filtrate was evaporated. The residue was purified by column chromatography on silica using a 21:1 mixture of methylene chloride and a saturated methanolic ammonia solution as eluent. There was thus obtained cis-3,5-dimethyl-1-(3-hydroxypropyl)piperazine (5.84 g).

A mixture of a portion (2.5 g) of the material so obtained, trityl chloride (4.25 g), 4-dimethylaminopyridine (0.018 g), triethylamine (2.2 ml) and DMF (40 ml) was stirred and heated to 40° C. for 5 hours. The mixture was evaporated and the residue was partitioned between ethyl acetate and water. The organic phase was washed with water and with brine, dried over magnesium sulphate and evaporated to give cis-3,5-dimethyl-1-(3-trityloxypropyl)piperazine as a foam (5 g); NMR Spectrum: ($DMSOd_6$ and $CD_3CO_2D$) 1.18 (s, 3H), 1.2 (s, 3H), 1.7 (m, 2H), 1.95 (m, 2H), 2.45 (m, 2H), 2.9 (m, 2H), 3.05 (t, 2H), 3.15 (m, 2H), 7.2–7.5 (m, 15H).

A mixture of the material so obtained, 2-bromoacetonitrile (0.925 ml), potassium carbonate (5 g), tri-n-butylammonium iodide (0.44 g) and DMF (12 ml) was stirred and heated to 40° C. for 6 hours. The mixture was filtered and the filtrate was evaporated. The residue was partitioned between ethyl acetate and water. The organic phase was washed with water and with brine, dried over magnesium sulphate and evaporated. The material so obtained was purified by column chromatography on silica a 17:3 mixture of methylene chloride and methanol as eluent. There was thus obtained cis-3,5-dimethyl-4-cyanomethyl-1-(3-trityloxypropyl)-piperazine (2.7 g) as a gum.

A mixture of cis-3,5-dimethyl-4-cyanomethyl-1-(3-tntyloxypropyl)-piperazine (3 g), a 1N aqueous hydrochloric acid solution (20 ml) and methanol (100 ml) was stirred at ambient temperature for 17 hours. The solvent was evaporated and the residual aqueous solution was basified to pH 11 by the addition of a a saturated aqueous sodium carbonate solution. The mixture was extracted with ethyl acetate and the organic phase was washed with water and with brine, dried and evaporated. The material so obtained was purified by column chromatography on silica using a 9:1 mixture of methylene chloride and methanol as eluent. There was thus obtained cis-3,5-dimethyl-4-cyanomethyl-1-(3-hydroxypropyl)piperazine as a gum (0.4 g); NMR Spectrum: ($CDCl_3$) 1.07 (s, 3H), 1.09 (s, 3H), 1.75 (m, 2H), 1.9 (t, 2H), 2.55 (t, 2H), 2.7 (m, 2H), 2.95 (d, 2H), 3.75 (s, 2H), 3.8 (t, 2H).

[31] The reaction mixture was stirred at ambient temperature for 5 hours. The product gave the following characterising data; NMR Spectrum: ($DMSOd_6$ and $CF_3CO_2D$) 1.28 (s, 3H), 1.3 (s, 3H), 2.35 (m, 2H), 3.05 (t, 2H), 3.4 (m, 2H), 3.65 (m, 2H), 3.9 (d, 2H), 4.0 (s,3H), 4.3 (t, 2H), 6.1 (s, 2H), 7.0 (m, 3H), 7.4 (s, 1H), 8.1 (s, 1H), 8.9 (s, 1H); Mass Spectrum: M + $H^+$ 466.

[32] The reaction mixture was stirred at ambient temperature for 1 hour. The product gave the following characterising data; NMR Spectrum: ($DMSOd_6$ and $CF_3CO_2D$) 2.3 (m, 2H), 3.05 (s, 3H), 3.1–3.3 (m, 4H), 3.4 (t, 2H), 3.6–3.9 (m, 4H), 4.05 (s, 3H), 4.35 (t, 2H), 6.15 (s, 2H), 7.1 (d, 1H), 7.2 (d, 1H), 7.4 (s, 1H), 8.15 (s, 1H), 8.9 (s, 1H); Mass Spectrum: M + $H^+$ 550.

The 1-(3-hydroxypropyl)-4-mesylpiperazine used as a starting material was prepared as follows:-

Mesyl chloride (0.966 ml) was added dropwise to a stirred mixture of 1-benzylpiperazine (2 g), triethylamine (1.74 ml) and methylene chloride (30 ml) which was cooled to 0° C.. The reaction mixture was allowed to warm to ambient temperature and stirred for 1 hour. The mixture was partitioned between methylene chloride and water. The organic phase was washed with water and with brine, dried over magnesium sulphate and evaporated. The residue was purified by column chromatography on silica using a 7:3 mixture of methylene chloride and ethyl acetate as eluent. There was thus obtained 1-benzyl-4-mesylpiperazine (2.5 g) as a solid; NMR Spectrum: ($CDCl_3$) 2.6 (m, 4H), 2.8 (s, 3H), 3.3 (m, 4H), 3.55 (s, 2H), 7.3 (m, 5H); Mass Spectrum: M + $H^+$ 255.

A mixture of the material so obtained, cyclohexene (30 ml), palladium oxide on charcoal catalyst (20%; 0.5 g) and ethanol (70 ml) was stirred and heated to 80° C. for 4 hours. The catalyst was removed by filtration and the solvent was evaporated to give 1-mesylpiperazine (1.58 g) as a solid; NMR Spectrum: ($CDCl_3$) 2.8 (s, 3H), 3.0 (m, 4H), 3.2 (m, 4H); Mass Spectrum: M + $H^+$ 165.

A mixture of the material so obtained, 3-bromopropanol (1.13 ml), potassium carbonate (1.73 g) and acetonitrile (10 ml) was stirred and heated to 40° C. for 4 hours and then to 70° C. for 2 hours. The excess of potassium carbonate was removed by filtration and the filtrate was evaporated. The residue was purified by column chromatography on silica using increasingly polar solvent mixtures of methylene chloride and methanol as eluent. There was thus obtained 1-(3-hydroxypropyl)-4-mesylpiperazine (1.95 g) as a solid; NMR Spectrum: ($CDCl_3$) 1.8 (m, 2H), 2.6–2.7 (m, 6H), 2.8 (s, 3H), 3.3 (m, 4H), 3.8 (t, 2H), 4.5 (br s, 1H); Mass Spectrum: M + $H^+$ 223.

TABLE II-continued

[33] The reaction mixture was stirred at ambient temperature for 5 hours. The product gave the following characterising data; NMR Spectrum: (DMSOd$_6$ and CF$_3$CO$_2$D) 2.3 (m, 2H), 2.95 (t, 2H), 3.2 (t, 2H), 3.4 (t, 2H), 2.9–3.7 (br m, 8H), 4.05 (s, 3H), 4.35 (t, 2H), 6.2 (s, 2H), 7.05 (d, 1H), 7.15 (d, 1H), 7.4 (s, 1H), 8.15 (s, 1H), 8.9 (s, 1H); Mass Spectrum: M + H$^+$ 525.
The 3-[4-(3-hydroxypropyl)piperazin-1-yl]propiomtrile used as a starting material was prepared as follows:-
Acrylonitrile (0.827 ml) was added to a mixture of 1-benzylpiperazine (2 g), methylene chloride (20 ml) and methanol (20 ml) and the resultant mixture was stirred at ambient temperature for 24 hours. The mixture was evaporated and the residue was purified by column chromatography on silica using a 97:3 mixture of methylene chloride and methanol as eluent. There was thus obtained 3-(4-benzylpiperazin-1-yl)propionitrile (2.63 g) as a liquid; NMR Spectrum: (CDCl$_3$) 2.5 (m, 10H), 2.7 (t, 2H), 3.55 (s, 2H), 7.3 (m, 5H); Mass Spectrum: M + H$^+$ 230.
The material so obtained was treated according to the procedures described in the last two paragraphs of the portion of Note [32] immediately above that is concerned with the preparation of starting materials. There was thus obtained 3-[4-(3-hydroxypropyl)piperazin-1-yl]propionitrile as a liquid (1.36 g); NMR Spectrum: (CDCl$_3$) 1.7 (m, 2H), 2.3–2.7 (m, 14H), 3.8 (t, 2H); Mass Spectrum: M + H$^+$ 198.
[34] The reaction mixture was stirred at ambient temperature for 5 hours. The product gave the following characterising data; NMR Spectrum: (DMSOd$_6$ and CF$_3$CO$_2$D) 0.95 (d, 6H), 2.05 (t, 2H), 2.45 (m, 4H), 2.6 (m, 2H), 2.85 (m, 1H), 3.5 (m, 4H), 3.95 (s, 3H), 4.2 (t, 2H), 6.05 (s, 2H), 6.9 (d, 1H), 7.05 (d, 1H), 7.2 (s, 1H), 7.85 (s, 1H), 8.3 (s, 1H); Mass Spectrum: M + H$^+$ 542 and 544.
The 1-(3-hydroxypropyl)-4-isobutyrylpiperazine used as a starting material was prepared as follows:-
Isobutyryl chloride (1.3 ml) was added dropwise to a stirred mixture of 1-benzylpiperazine (2 g), triethylamine (1.74 ml) and methylene chloride (30 ml) which was cooled to 0° C.. The reaction mixture was allowed to warm to ambient temperature and stirred for 1 hour. The mixture was partitioned between methylene chloride and water. The organic phase was washed with water and with brine, dried over magnesium sulphate and evaporated. The residue was purified by column chromatography on silica using a 3:2 mixture of methylene chloride and ethyl acetate as eluent. There was thus obtained 1-benzyl-4-isobutyrylpiperazine (2.6 g) as an oil; NMR Spectrum: (DMSOd$_6$ and CF$_3$CO$_2$D) 1.15 (d, 6H), 2.45 (m, 4H), 2.8 (m, 1H), 3.5 (m, 4H), 3.65 (m, 2H), 7.3 (m, 5H); Mass Spectrum: M + H$^+$ 247.
The material so obtained was treated according to the procedures described in the last two paragraphs of the portion of Note [32] immediately above that is concerned with the preparation of starting materials. There was thus obtained 1-(3-hydroxypropyl)-4-isobutyrylpiperazine as a liquid (1.7 g); NMR Spectrum: (CDCl$_3$) 1.1 (d, 6H), 1.7 (m, 2H), 2.45 (m, 4H), 2.6 (t, 2H), 2.75 (m, 1H), 3.5 (m, 2H), 3.6 (m, 2H), 3.8 (t, 2H), 4.7 (br s, 1H); Mass Spectrum: M + H$^+$ 215.

EXAMPLE 9

7-(2-homopiperidin-1-ylethoxy)-4-(2,3-methylenedioxyanilino)-6-methoxyquinazoline A mixture of 7-(2-bromoethoxy)-4-(2,3-methylenedioxyanilino)-6-methoxyquinazoline (0.48 g) homopiperidine (0.322 ml), sodium iodide (0.002 g), DMF (5 ml) and acetonitrile (6 ml) was stirred and heated to 45° C. for 5 hours. The mixture was evaporated and the residue was partitioned between methylene chloride and water. The organic phase was washed with brine, dried over magnesium sulphate and evaporated. The residue was purified by column chromatography on silica using a 19:1 mixture of methylene chloride and a saturated methanolic ammonia solution as eluent. The material so obtained was triturated under diethyl ether to give the title compound as a solid (0.4 g); NMR Spectrum: (DMSOd$_6$ and CF$_3$CO$_2$D) 1.65 (m, 4H), 1.9 (m, 4H), 3.35 (m, 2H), 3.55 (m, 2H), 3.7 (m, 2H), 4.0 (s, 3H), 4.6 (m, 2H), 6.1 (s, 2H), 7.0 (m, 3H), 7.45 (s, 1H), 8.15 (s, 1H), 8.9 (s, 1H); Mass Spectrum: M+H$^+$ 437.

The 7-(2-bromoethoxy)-4-(2,3-methylenedioxyanilino)-6-methoxyquinazoline used as a starting material was prepared as follows:-
1,1'-(Azodicarbonyl)dipiperidine (6 g) was added to a stirred mixture of 7-hydroxy-4-(2,3-methylenedioxyanilino)-6-methoxyquinazoline (3 g), 2-bromoethanol (1 ml), tributylphosphine (5.9 ml) and chloroform (300 ml) which was heated to 40° C. The mixture was heated to 40° C. for 10 minutes and then stirred at ambient temperature for 2 hours. The mixture was evaporated and the residue was purified by column chromatography on silica using a 11:9 mixture of methylene chloride and acetonitrile as eluent. There was thus obtained 7-(2-bromoethoxy)-4-(2,3-methylenedioxyanilino)-6-methoxyquinazoline (1.8 g); NMR Spectrum: (DMSOd$_6$) 3.9 (t, 2H), 3.95 (s, 3H), 4.55 (t, 2H), 6.05 (s, 2H), 6.9 (m, 3H), 7.2 (s, 1H), 7.9 (s, 1H), 8.4 (s, 1H), 9.65 (br s, 1H).

EXAMPLE 10

Using an analogous procedure to that described in Example 9, the appropriate 7-haloalkoxyquinazoline was reacted with the appropriate amine to give the compounds described in Table III. Unless otherwise stated, each compound described in Table III was obtained as the free base.

TABLE III

| Compound No. & Note | R$^1$ | R$^2$ |
|---|---|---|
| [1] | 2-pyrrolidin-1-ylethoxy | hydrogen |
| [2] | 2-piperidinoethoxy | hydrogen |
| [3] | 3-homopiperidin-1-ylpropoxy | hydrogen |
| [4] | 3-(cis-3,5-dimethylpiperazin-1-yl)propoxy | 6-chloro |
| [5] | 3-(4-hydroxypiperidin-1-yl)propoxy | 6-chloro |
| [6] | 3-[N,N-di-(2-hydroxyethyl)amino]propoxy | 6-chloro |

Notes
[1] 7-(2-Bromoethoxy)-4-(2,3-methylenedioxyanilino)-6-methoxyquinazoline was used as a starting material, DMF was used as the sole reaction solvent and the reaction mixture was warmed to 27° C. for 4 hours. The product gave the following characterising data; NMR Spectrum: (DMSOd$_6$ and CF$_3$CO$_2$D) 1.9 (m, 2H), 2.1 (m, 2H), 3.2 (m, 2H), 3.7 (m, 2H), 3.75 (m, 2H), 4.0 (s, 3H), 4.55 (m, 2H), 6.1 (s, 2H), 7.0 (m, 3H), 7.45 (s, 1H), 8.15 (s, 1H), 8.9 (d, 1H); Mass Spectrum: M − H$^-$ 407.
[2] 7-(2-Bromoethoxy)-4-(2,3-methylenedioxyanilino)-6-methoxyquinazoline was used as a starting material, DMF was used as the sole reaction solvent and the reaction mixture was warmed to 30° C. for 3.5 hours. The product gave the following characterising data; NMR Spectrum: (DMSOd$_6$ and CF$_3$CO$_2$D) 1.4 (m, 1H), 1.7 (m, 3H), 1.9 (m, 2H), 3.1 (t, 2H), 3.6 (m, 2H), 3.65 (m, 2H), 4.05 (s, 3H), 4.6 (t, 2H), 6.1 (s, 2H), 7.0 (m, 3H), 7.4 (s, 1H), 8.15 (s, 1H), 8.9 (s, 1H); Mass Spectrum: M + H$^+$ 423.
[3] The product gave the following characterising data; NMR Spectrum: (DMSOd$_6$ and CF$_3$CO$_2$D) 1.6 (m, 4H), 1.8 (m, 4H), 2.3 (m, 2H), 3.2 (m, 2H), 3.3 (m, 2H), 3.45 (m, 2H), 4.0 (s, 3H), 4.3 (t, 2H), 6.1 (s, 2H), 7.0 (m, 3H), 7.4 (s, 1H), 8.1 (s, 1H), 8.9 (s, 1H); Mass Spectrum: M + H$^+$ 451.
The 7-(3-chloropropoxy)-4-(2,3-methylenedioxyanilino)-6-methoxyquinazoline used as a starting material was prepared as follows:-
A mixture of 7-hydroxy-4-(2,3-methylenedioxyanilino)-6-methoxyquinazoline (2 g) and DMF (40 ml) was warmed until the

TABLE III-continued starting material was completely dissolved. The solution was cooled to ambient temperature and 3-chloropropyl bromide (0.826 ml), tetrabutylammonium iodide (0.237 g) and caesium carbonate (4.2 g) were added in turn. The resultant mixture was stirred at ambient temperature for 20 hours. Water was added and the mixture was extracted with ethyl acetate (2×). The combined organic phases were washed with water and with brine, dried over magnesium sulphate and evaporated. The residue was purified by column chromatography on silica using a 24:1 mixture of methylene chloride and methanol as eluent. There was thus obtained 7-(3-chloropropoxy)-4-(2,3-methylenedioxyanilino)-6-methoxyquinazoline (1.8 g); NMR Spectrum: (DMSOd$_6$ and CF$_3$CO$_2$D) 2.3 (m, 2H), 3.85 (t, 2H), 4.0 (s, 3H), 4.35 (t, 2H), 6.1 (s, 2H), 7.0 (m, 3H), 7.35 (s, 1H), 8.1 (s, 1H), 8.85 (s, 1H); Mass Spectrum: M + H$^+$ 388 and 390.

[4] Acetonitrile was used as the sole reaction solvent and the reaction mixture was warmed to 60° C. for 5 hours. The product gave the following characterising data; NMR Spectrum: (DMSOd$_6$ and CF$_3$CO$_2$D) 1.29 (s, 3H), 1.31 (s, 3H), 2.35 (m, 2H), 3.0 (m, 2H), 3.4 (m, 2H), 3.65 (m, 2H), 3.85 (m, 2H), 4.0 (s, 3H), 4.35 (m, 2H), 6.15 (s, 2H), 7.05 (d, 1H), 7.15 (d, 1H), 7.4 (s, 1H), 8.15 (s, 1H), 8.9 (s, 1H); Mass Spectrum: M − H$^-$ 498 and 500.

The 7-(3-bromopropoxy)-4-(6-chloro-2,3-methylenedioxyanilino)-6-methoxyquinazoline used as a starting material was prepared as follows:- 1,1'-(Azodicarbonyl)dipiperidine (0.725 g) was added to a stirred mixture of 4-(6-chloro-2,3-methylenedioxyanilino)-7-hydroxy-6-methoxyquinazoline (0.5 g), 3-bromopropanol (0.234 ml), tributylphosphine (0.715 ml), methylene chloride (50 ml) and THF (20 ml) and the reaction mixture was stirred at ambient temperature for 1 hour. Second portions of tributylphosphine (0.357 ml) and 1,1'-(azodicarbonyl)dipiperidine (0.362 g) were added and the reaction mixture was stirred for another 2 hours. The resultant mixture was evaporated and the residue was purified by column chromatography on silica using a 7:3 mixture of methylene chloride and acetonitrile as eluent. There was thus obtained 7-(3-bromopropoxy)-4-(6-chloro-2,3-methylenedioxyanilino)-6-methoxyquinazoline as a solid (0.3 g); NMR Spectrum: (DMSOd$_6$) 2.35 (m, 2H), 3.7 (t, 2H), 3.95 (s, 3H), 4.25 (t, 2H), 6.1 (s, 2H), 6.95 (d, 1H), 7.05 (d, 1H), 7.2 (s, 1H), 7.85 (s, 1H), 8.3 (s, 1H), 9.5 (s, 1H); Mass Spectrum: M + H$^+$ 466.

[5] The reaction mixture was heated to reflux for 16 hours. The product gave the following characterising data; NMR Spectrum: (DMSOd$_6$) 1.4 (m, 2H), 1.75 (m, 2H), 1.95 (m, 2H), 2.0 (m, 2H), 2.4 (t, 2H), 2.75 (m, 2H), 3.5 (m, 1H), 3.95 (s, 3H), 4.2 (t, 2H), 4.55 (s, 1H), 6.1 (s, 2H), 6.95 (d, 1H), 7.1 (d, 1H), 7.2 (s, 1H), 7.85 (s, 1H), 8.35 (s, 1H), 9.5 (s, 1H); Mass Spectrum: M + H$^+$ 487.

The 4-(6-chloro-2,3-methylenedioxyanilino)-7-(3-chloropropoxy)-6-methoxyquinazoline used as a starting material was prepared as follows:- A mixture of 4-(6-chloro-2,3-methylenedioxyanilino)-7-hydroxy-6-methoxyquinazoline (1.5 g), 3 chloropropyl bromide (0.54 ml), potassium carbonate (1.5 g) and DMF (20 ml) was stirred at ambient temperature for 16 hours. The mixture was partitioned between ethyl acetate and water. The organic phase was washed with water and with brine, dried over magnesium sulphate and evaporated. The residue was triturated under diethyl ether and the resultant solid was isolated, washed with diethyl ether and dried under vacuum. There was thus obtained 4-(6-chloro-2,3-methylenedioxyanilino)-7-(3-chloropropoxy)-6-methoxyquinazoline (1.34 g); NMR Spectrum: (DMSOd$_6$) 2.25 (m, 2H), 3.85 (t, 2H), 3.95 (t, 3H), 4.3 (t, 2H), 6.1 (s, 2H), 6.95 (d, 1H), 7.05 (d, 1H), 7.15 (s, 1H), 7.85 (s, 1H), 8.35 (s, 1H), 9.5 (br s, 1H).

[6] 4-(6-Chloro-2,3-methylenedioxyanilino)-7-(3-chloropropoxy)-6-methoxyquinazoline was used as a starting material and the reaction mixture was heated to reflux for 16 hours. The product gave the following characterising data; NMR Spectrum: (DMSOd$_6$) 1.9 (m, 2H), 2.7 (m, 2H), 3.35–3.5 (m, 8H), 3.95 (s, 3H), 4.2 (t, 2H), 4.35 (t, 2H), 6.1 (s, 2H), 6.95 (d, 1H), 7.1 (d, 1H), 7.2 (s, 1H), 7.85 (s, 1H), 8.3 (s, 1H), 9.5 (s, 1H); Mass Spectrum: M + H$^+$ 491.

EXAMPLE 11

4-(6-chloro-2,3-methylenedioxyanilino)-6-methoxy-7-(3-piperazin-1-ylpropoxy)quinazoline dihydrochloride salt A mixture of 7-[3-(4-tert-butoxycarbonylpiperazin-1-yl)propoxy]-4-(6-chloro-2,3-methylenedioxyanilino)-6-methoxyquinazoline (0.286 g), trifluoroacetic acid (0.5 ml) and methylene chloride (6 ml) was stirred at ambient temperature for 3 hours. The solvent was evaporated and the residue was partitioned between methylene chloride and a saturated aqueous sodium bicarbonate solution. The organic phase was washed with water and with brine, dried over magnesium sulphate and evaporated. The material so obtained was triturated under a 6M solution of hydrogen chloride in diethyl ether. There was thus obtained the title compound (0.205 g); NMR Spectrum: (DMSOd$_6$ and CF$_3$CO$_2$D) 2.35 (m, 2H), 3.2–3.9 (m, 10H), 4.0 (s, 3H), 4.35 (m, 2H), 6.12 (s, 2H), 7.0 (s, 1H), 7.1 (s, 1H), 7.38 (s, 1H), 8.15 (s, 1H), 8.85 (s, 1H); Mass Spectrum: M+H$^+$ 472 and 474

EXAMPLE 12

4-(6-chloro-2,3-methylenedioxyanilino)-7-[3-(4-cyanomethylpiperazin-1-yl)propoxy]-6-methoxyquinazoline A mixture of 4-(6-chloro-2,3-methylenedioxyanilino)-6-methoxy-7-(3-piperazin-1-ylpropoxy)quinazoline (0.19 g), 2-chloroacetonitrile (0.038 ml), potassium iodide (0.020 g), potassium carbonate (0.139 g) and DMF (2.5 ml) was stirred at ambient temperature for 16 hours. The reaction mixture was partitioned between ethyl acetate and water. The organic phase was washed with water and with brine, dried over magnesium sulphate and evaporated. The crude product was purified by column chromatography on silica using a 93:7 mixture of methylene chloride and methanol as eluent. There was thus obtained the title compound (0.13 g) as a solid; NMR Spectrum: (DMSOd$_6$ and CF$_3$CO$_2$D) 2.3 (m, 2H), 2.6 (m, 2H), 3.05 (m, 2H), 3.15 (m, 2H), 3.35 (m, 2H), 3.65 (m, 2H), 3.9 (s, 2H), 4.05 (s, 3H), 4.35 (m, 2H), 6.15 (s, 2H), 7.05 (d, 1H), 7.15 (d, 1H), 7.4 (s, 1H), 8.15 (s, 1H), 8.9 (s, 1H); Mass Spectrum: [M−H]$^-$ 509 and 511; Elemental Analysis: Found C, 58.41; H, 5.62; N, 15.93. C$_{25}$H$_{27}$ClN$_6$O$_4$ 0.2H$_2$O requires C, 58.35; H, 5.37; N, 16.33%.

EXAMPLE 13

6-methoxy-4-(2,3-methylenedioxyanilino)-7-(3-piperazin-1-ylpropoxy)quinazoline dihydrochloride salt Using an analogous procedure to that described in Example 11, 7-[3-(4-tert-butoxycarbonylpiperazin-1-yl)propoxy]-6-methoxy-4-(2,3-methylenedioxyanilino)quinazoline was reacted with trifluoroacetic acid to give the title compound; NMR Spectrum: (DMSOd$_6$ and CF$_3$CO$_2$D) 2.3–2.4 (m, 2H), 3.2–3.95 (m, 10H), 4.05 (s, 3H), 4.38 (m, 2H), 6.1 (s, 2H), 7.0 (s, 3H), 7.4 (s, 1H), 8.2 (s, 1H), 8.9 (s, 1H); Mass Spectrum: M+H$^+$ 438.

EXAMPLE 14

7-[3-(4-cyanomethylpiperazin-1-yl)propoxy]-6-methoxy-4-(2,3-methylenedioxyanilino)quinazoline Using an analogous procedure to that described in Example 12, 6-methoxy-4-(2,3-methylenedioxyanilino)-7-(3-piperazin-1-ylpropoxy)quinazoline was reacted with 2-chloroacetonitrile to give the title compound as a solid; NMR Spectrum: (DMSOd$_6$) 2.1 (m, 2H), 2.45–2.7 (m, 11H), 3.5 (s, 2H), 4.0 (s, 3H), 4.25 (t, 2H), 6.0 (s, 2H), 6.7 (d, 1H), 6.9 (t, 1H), 7.0 (m, 2H), 7.75 (d, 1H), 8.7 (s, 1H); Mass Spectrum: M+H$^+$ 477.

EXAMPLE 15

4-(6-bromo-2,3-methylenedioxyanilino)-6-methoxy-7-(3-piperidinopropoxy)quinazoline Sodium hexamethyldisilazane (1M solution in THF; 0.626 ml) was added to a solution of 6-bromo-2,3-methylenedioxyaniline (0.135 g) in DMF (2 ml) and the mixture was stirred at ambient temperature for 30 minutes. A solution of 4-chloro-6-methoxy-7-(3-piperidinopropoxy)quinazoline (0.1 g) in DMF (3.5 ml) was added and the resultant mixture was stirred at ambient temperature for 3 hours. The reaction mixture was diluted with water and extracted with ethyl acetate (2×). The organic phase was washed with water and with brine, dried over magnesium sulphate and evaporated. The residue was purified by column chromatography on silica using an 80:17:3 mixture of methylene chloride, methanol and a saturated methanolic ammonia solution as eluent. There was thus obtained the title compound as a solid (0.045 g); NMR Spectrum: (DMSOd$_6$ and CF$_3$CO$_2$D) 1.4 (m, 1H), 1.7 (m, 3H), 1.85 (m, 2H), 2.3 (m, 2H), 2.95 (m, 2H), 3.25 (m, 2H), 3.55 (m, 2H), 4.05 (s, 3H), 4.3 (m, 2H), 6.15 (s, 2H), 7.05 (d, 1H), 7.3 (d, 1H), 7.4 (s, 1H), 8.15 (s, 1H), 8.9 (s, 1H); Mass Spectrum: M+H$^+$ 515 and 517; Elemental Analysis: Found C, 55.74; H, 5.30; N, 10.76. C$_{24}$H$_{27}$BrN$_4$O$_4$ requires C, 55.93; H, 5.28; N, 10.87%.

EXAMPLE 16

4-(6-bromo-2,3-methylenedioxyanilino)-6-methoxy-7-[3-(4-methylpiperazin-1-yl)propoxy]quinazoline Using an analogous procedure to that described in Example 15, 4-chloro-6-methoxy-7-[3-(4-methylpiperazin-1-yl)propoxy]quinazoline was reacted with 6-bromo-2,3-Methylenedioxyaniline to give the title compound as a solid; NMR Spectrum: DMSOd$_6$ and CF$_3$CO$_2$D) 2.3 (m, 2H), 2.95 (s, 3H), 3.2–3.9 (br s, 8H), 3.4 (m, 2H), 4.0 (s, 3H), 4.35 (m, 2H), 6.15 (s, 2H), 7.05 (d, 1H), 7.3 (d, 1H), 7.4 (s, 1H), 8.15 (s, 1H), 8.9 (s, 1H); Mass Spectrum: M+H$^+$ 530 and 532; Elemental Analysis: Found C, 54.25; H, 5.54; N, 12.8. C$_{24}$H$_{28}$BrN$_5$O$_4$ requires C, 54.35; H, 5.32; N, 13.2%.

EXAMPLE 17

7-[2-(4-hydroxypiperidin-4-yl)ethoxy]-6-methoxy-4-(2,3-methylenedioxyanilino)quinazoline A mixture of 7-[2-(N-tert-butoxycarbonyl-4-hydroxypiperidin-4-yl)ethoxy]-6-methoxy-4-(2,3-methylenedioxyanilino)quinazoline (0.067 g), trifluoroacetic acid (0.5 ml) and methylene chloride (3 ml) was stirred at ambient temperature for 1 hour. The solvent was evaporated and the residue was partitioned between methylene chloride and a saturated aqueous sodium bicarbonate solution. The organic phase was washed with brine, dried over magnesium sulphate and evaporated. There was thus obtained the title compound (0.015 g); NMR Spectrum: (DMSOd$_6$ and CF$_3$CO$_2$D) 1.75 (m, 4H), 2.05 (t, 2H), 3.1 (m, 4H), 4.0 (s, 3H), 4.35 (t, 2H), 6.1 (s, 2H), 6.95 (m, 3H), 7.4 (s, 1H), 8.1 (s, 1H), 8.85 (s, 1H); Mass Spectrum: M+H$^+$ 439.

EXAMPLE 18

7-[2-(4-hydroxy-N-methylpiperidin-4-yl)ethoxy]-6-methoxy-4-(2,3-methylenedioxyanilino)quinazoline A mixture of 7-[2-(4-hydroxypiperidin-4-yl)ethoxy]-6-methoxy-4-(2,3-methylenedioxyanilino)quinazoline (0.065 g), formaldehyde (40% aqueous solution; 0.2 ml) and formic acid (2 ml) was stirred and heated to 100° C. for 1.5 hours. The mixture was basified to pH9.5 by the addition of 2N aqueous sodium hydroxide solution and extracted with ethyl acetate. The organic phase was washed with water and with brine, dried over magnesium sulphate and evaporated. The residue was purified by column chromatography on silica using an 80:17:3 mixture of methylene chloride, methanol and a saturated methanolic ammonia solution as eluent. There was thus obtained the title compound as a solid (0.021 g); NMR Spectrum: (DMSOd$_6$ and CF$_3$CO$_2$D) 1.8 (m, 4H), 2.05 (m, 2H), 2.8 (s, 3), 3.15 (m, 2H), 3.3 (m, 2H), 4 (s, 3H), 4.35 (m, 2H), 6.05 (s, 2H), 6.95 (m, 3H), 7.4 (s, 1H), 8.1 (s, 1H), 8.85 (s, 1H); Mass Spectrum: M+H$^+$ 453.

EXAMPLE 19

4-(6-chloro-2,3-methylenedioxyanilino)-6-methoxy-7-(piperidin-4-ylmethoxy)quinazoline dihydrochloride salt Using an analogous procedure to that described in Example 11, 7-(N-tert-butoxycarbonylpiperidin-4-ylmethoxy)-4-(6-chloro-2,3-methylenedioxyanilino)-6-methoxyquinazoline was reacted with trifluoroacetic acid. The material so obtained was triturated under a 6M solution of hydrogen chloride in diethyl ether. There was thus obtained the title compound; NMR Spectrum: (DMSOd$_6$) 1.5–1.65 (m, 2H), 2.0 (d, 2H), 2.2 (m, 1H), 2.95 (m, 2H), 3.2–3.4 (m, 2H), 4.02 (s, 3H), 4.12 (d, 2H), 6.15 (s, 2H), 7.05 (d, 1H), 7.15 (d, 1H), 7.42 (s, 1H), 8.22 (s, 1H), 8.8 (s, 1H); Mass Spectrum: M+H$^+$ 443 and 445.

EXAMPLE 20

4-(6chloro-2,3-methylenedioxyanilino)-7-(N-cyanomethylpiperidin-4-ylmethoxy)-6-methoxyquinazoline Using an analogous procedure to that described in Example 12, 4-(6-chloro-2,3-methylenedioxyanilino)-6-methoxy-7-(piperidin-4-ylmethoxy)quinazoline was reacted with 2-chloroacetonitrile to give the title compound as a solid; NMR Spectrum: (DMSOd$_6$) 1.65 (m, 2H), 2.1 (m, 2H), 2.2 (m, 1H), 3.15 (m, 2H), 3.6 (m, 2H), 4.05 (s, 3H), 4.15 (m, 2H), 4.55 (s, 2H), 6.15 (s, 2H), 7.05 (d, 1H), 7.15 (d, 1H), 7.4 (s, 1H), 8.15 (s, 1H), 8.9 (s, 1H); Mass Spectrum: M−H$^-$ 480 and 482.

EXAMPLE 21

7-(2-hydroxy-3-morpholinopropoxy)-6-methoxy-4-(2,3-methylenedioxyanilino)quinazoline dihydrochloride salt A mixture of 7-(2-acetoxy-3-morpholinopropoxy)-6-methoxy-4-(2,3-methylenedioxyanilino)quinazoline dihydrochloride (0.104 g) and a saturated methanolic ammonia solution (3 ml) was stirred at ambient temperature for 16 hours. The mixture was evaporated and the residue was purified by column chromatography on silica (Isolute ammonia-treated silica from International Sorbent Technology Limited, catalogue reference 9470-0100) using a 19:1 mixture of methylene chloride and methanol as eluent. The material so obtained was dissolved in methylene chloride (3 ml) and a 6M solution of hydrogen chloride in isopropanol (0.3 ml) was added with stirring. Diethyl ether (10 ml) was added and the resultant precipitate was isolated, washed with diethyl ether and dried under vacuum. There was thus obtained the title compound (0.095 g); NMR Spectrum: (DMSOd$_6$ and CF$_3$CO$_2$D) 3.15–3.45 (m, 4H), 3.54 (d, 2H), 3.74–3.91 (d, 2H), 3.97 (d, 2H), 4.02 (s, 3H), 4.24 (d, 2H), 4.49–4.58 (m, 1H), 6.08 (s, 2H), 6.96–7.04 (m, 3H), 7.47 (s, 1H), 8.23 (s, 1H), 8.88 (s, 1H); Mass Spectrum: M+H$^+$ 455.

EXAMPLE 22

Using an analogous procedure to that described in Example 21, the appropriate 7-(2-acetoxypropoxy)quinazoline was cleaved to give the compounds described in Table IV. Unless otherwise stated, each compound described in Table IV was obtained as a dihydrochloride salt.

TABLE IV

| Compound No. & Note | R$^1$ | R$^2$ |
|---|---|---|
| [1] | 2-hydroxy-3-pyrrolidin-1-ylpropoxy | hydrogen |
| [2] | 2-hydroxy-3-piperidinopropoxy | hydrogen |
| [3] | 3-(4-cyanomethylpiperazin-1-yl)-2-hydroxypropoxy | hydrogen |
| [4] | 2-hydroxy-3-(N-isopropyl-N-methylamino)propoxy | hydrogen |

Notes
[1] The product gave the following characterising data; NMR Spectrum: (DMSOd$_6$ and CF$_3$CO$_2$D) 1.85–1.98 (m, 2H), 1.99–2.1 (m, 2H), 3.07–3.2 (m, 2H), 3.33–3.42 (m, 2H), 3.57–3.68 (m, 2H), 4.02 (s, 3H), 4.22 (d, 2H), 4.34–4.43 (m, 1H), 6.08 (s, 2H), 6.94–7.04 (m, 3H), 7.45 (s, 1H), 8.22 (s, 1H), 8.87 (s, 1H); Mass Spectrum: M + H$^+$ 439.
[2] The product gave the following characterising data; NMR Spectrum: (DMSOd$_6$ and CF$_3$CO$_2$D) 1.36–1.51 (m, 1H), 1.65–1.78 (m, 2H), 1.79–1.92 (m, 3H), 2.93–3.11 (m, 2H), 3.2–3.74 (m, 2H), 3.54 (t, 2H), 4.02 (s, 3H), 4.24 (d, 2H), 4.46–4.54 (m, 1H), 6.08 (s, 2H), 6.95–7.03 (m, 3H), 7.44 (s, 1H), 8.2 (s, 1H), 8.88 (s, 1H); Mass Spectrum: M + H$^+$ 453.
[3] The product gave the following characterising data; NMR Spectrum: (DMSOd$_6$ and CF$_3$CO$_2$D) 2.54–3.12 (m, 4H), 3.13–3.48 (m, 3H), 3.55–3.73 (m, 2H), 3.89 (s, 3H), 4.03 (s, 3H), 4.22–4.3 (m, 2H), 4.46–4.59 (m, 1H), 6.08 (s, 2H), 7.95–7.03 (m, 3H), 7.49 (s, 1H), 8.27 (s, 1H), 8.87 (s, 1H); Mass Spectrum: M + H$^+$ 493.
[4] The product gave the following characterising data; NMR Spectrum: (DMSOd$_6$ and CF$_3$CO$_2$D) 1.2–1.36 (m, 6H), 2.78 (d, 3H), 3.04–3.71 (m, 3H), 4.03 (s, 3H), 4.24 (d, 2H), 4.41–4.55 (m, 1H), 6.05 (s, 2H), 5.88–6.06 (m, 3H), 7.48 (d, 1H), 8.36 (s, 1H), 8.82 (s, 1H), 9.5–10.1 (m, 1H), 11.65 (s, 1H); Mass Spectrum: M + H$^+$ 441.

EXAMPLE 23

7-[(2R)-2-hydroxy-3-pyrrolidin-1-ylpropoxy]-6-methoxy-4-(2,3-methylenedioxyanilino)quinazoline dihydrochloride salt A mixture of pyrrolidine (0.016 ml), 7-[(2R)-2,3-epoxypropoxy]-6-methoxy-4-(2,3-methylenedioxyanilino)quinazoline (0.03 g), chloroform (0.5 ml) and ethanol (0.5 ml) was stirred and heated to 40° C. for 7 hours. The mixture was evaporated and the residue was dissolved in methylene chloride (4 ml). A polystyrene isocyanate resin (prepared according to J. Amer. Chem. Soc., 1997, 119, 4882; loading: 1 mmol/g; 0.3 g) was added and the mixture was shaken at ambient temperature for 1.5 hours. The resin was removed by filtration and washed with methylene chloride. The filtrate was evaporated and the crude product so obtained was purified by column chromatography on silica using increasingly polar mixtures of methylene chloride and a saturated methanolic ammonia solution as eluent. The material so obtained was dissolved in a 9:1 mixture of methylene chloride and methanol (3 ml) and a 2.2M solution. of hydrogen chloride in diethyl ether (1 ml) was added. The precipitate was isolated and dried under vacuum. There was thus obtained the title compound (0.026 g); NMR Spectrum: (DMSOd$_6$ and CF$_3$CO$_2$D) 1.85–2.15 (m, 4H), 3.06–3.25 (m, 2H), 3.31–3.47 (m, 2H), 3.6–3.74 (m, 2H), 4.04 (s, 3H), 4.8 (d,2H), 4.38–4.46 (m, 1H), 6.1 (s, 2H), 6.94–7.05 (m, 3H), 7.49 (s, 1H), 8.27 (s, 1H), 8.88 (s, 1H); Mass Spectrum: M+H$^+$ 439.

The 7-[(2R)-2,3-epoxypropoxy]-6-methoxy-4-(2,3-methylenedioxyanilino)quinazoline used as a starting material was prepared as follows:

(2R)-(−)-Glycidyl tosylate (3.2 g) was added to a mixture of 7-hydroxy-4-(2,3-methylenedioxyanilino)-6-methoxyquinazoline (4 g), potassium carbonate (8.8 g) and DMF (80 ml) and the mixture was stirred at ambient temperature for 16 hours. The resultant precipitate was isolated and the filtrate was evaporated to give a first batch of the reaction product. The precipitate was triturated under a mixture of ethyl acetate and a 5% aqueous ammonium hydroxide solution. The mixture was filtered and the filtrate was washed with water and with brine, dried over magnesium sulphate and evaporated to give a further batch of the reaction product. The batches of product were combined and purified by column chromatography on silica using a 12:7:1 mixture of methylene chloride, ethyl acetate and methanol as eluent. There was thus obtained 7-[(2R)-2,3-epoxypropoxy]-6-methoxy-4-(2,3-methylenedioxyanilino)quinazoline as a solid (3.11 g); NMR Spectrum: (DMSOd$_6$ and CF$_3$CO$_2$D) 2.85 (m, 1H), 2.95 (m, 1H), 3.5 (m, 1H), 4.0 (s, 3H), 4.1 (m, 1H), 4.65 (m, 1H), 6.1 (s, 2H), 7.0 (m, 3H), 7.35 (s, 1H), 8.1 (s, 1H), 8.85 (s, 1H).

EXAMPLE 24

Using an analogous procedure to that described in Example 22, 7-[(2R)-2,3-epoxypropoxy]-6-methoxy-4-(2,3-methylenedioxyanilino)quinazoline was reacted with the appropriate amine to give the compounds described in Table V. Unless otherwise stated, each compound described in Table V was obtained as a dihydrochloride salt.

TABLE V

[Structure: Quinazoline core with MeO at 6-position, R¹ at 7-position, and HN-linked benzodioxole with R² substituent at 4-position]

| Compound No. & Note | R¹ | R² |
|---|---|---|
| [1] | (2R)-2-hydroxy-3-piperidinopropoxy | hydrogen |
| [2] | (2R)-3-homopiperidin-1-yl-2-hydroxypropoxy | hydrogen |
| [3] | (2R)-2-hydroxy-3-(N-isopropyl-N-methylamino)propoxy | hydrogen |
| [4] | (2R)-2-hydroxy-3-(N-isobutyl-N-methylamino)propoxy | hydrogen |
| [5] | 3-[(2S)-2-(N,N-dimethylcarbamoyl)-pyrrolidin-1-yl]-(2R)-2-hydroxypropoxy | hydrogen |
| [6] | (2R)-3-(N-allyl-N-cyclopentylamino)-2-hydroxypropoxy | hydrogen |
| [7] | (2R)-3-N-allyl-N-methylamino)-2-hydroxypropoxy | hydrogen |
| [8] | (2R)-2-hydroxy-3-pyrrolidin-1-ylpropoxy | 6-chloro |
| [9] | (2R)-2-hydroxy-3-piperidinopropoxy | 6-chloro |
| [10] | (2R)-3-homopiperidin-1-yl-2-hydroxypropoxy | 6-chloro |
| [11] | (2R)-2-hydroxy-3-(N-isopropyl-N-methylamino)propoxy | 6-chloro |
| [12] | (2R)-2-hydroxy-3-(N-isobutyl-N-methylamino)propoxy | 6-chloro |
| [13] | 3-[(2S)-2-(N,N-dimethylcarbamoyl)-pyrrolidin-1-yl]-(2R)-2-hydroxypropoxy | 6-chloro |
| [14] | (2R)-3-(N-allyl-N-methylamino)-2-hydroxypropoxy | 6-chloro |

Notes
[1] The product gave the following characterising data; NMR Spectrum: (DMSOd$_6$ and CF$_3$CO$_2$D) 1.35–1.5 (m, 1H), 1.65–1.94 (m, 5H), 2.93–3.13 (m, 2H), 3.2–3.4 (m, 2H), 3.49–3.61 (m, 2H), 4.03 (s, 3H), 4.24 (d, 2H), 4.47–4.57 (m, 1H), 6.08 (s, 2H), 6.94–7.05 (m, 3H), 7.47 (s, 1H), 8.24 (s, 1H), 8.88 (s, 1H); Mass Spectrum: M − H⁻ 451.
[2] The product gave the following characterising data; NMR Spectrum: (DMSOd$_6$ and CF$_3$CO$_2$D) 1.55–1.75 (m, 4H), 1.76–1.96 (m, 4H), 3.2–3.34 (m, 3H), 3.38–3.57 (m, 3H), 4.03 (s, 3H), 4.24 (d, 2H), 4.42–4.52 (m, 1H), 6.09 (s, 2H), 6.94–7.04 (m, 3H), 7.45 (s, 1H), 8.21 (s, 1H), 8.88 (s, 1H); Mass Spectrum: M + H⁺ 467.
[3] The product gave the following characterising data; NMR Spectrum: (DMSOd$_6$ and CF$_3$CO$_2$D) 1.21–1.39 (m, 6H), 2.81 (s, 3H), 3.08–3.77 (m, 3H), 4.02 (s, 3H), 4.26 (d, 2H), 4.39–4.53 (m, 1H), 6.08 (s, 2H), 6.92–7.05 (m, 3H), 7.46 (s, 1H), 8.22 (s, 1H), 8.83 (s, 1H); Mass Spectrum: M − H⁻ 439.
[4] The product gave the following characterising data; NMR Spectrum: (DMSOd$_6$ and CF$_3$CO$_2$D) 0.91–1.1 (m, 6H), 2.05–2.22 (m, 1H), 2.91 (br s, 3H), 2.92–3.04 (m, 1H), 3.08–3.48 (m, 3H), 4.03 (m, 3H), 4.17–4.34 (m, 2H.), 4.45–4.59 (m, 1H), 6.08 (s, 2H), 6.92–7.06 (m, 3H), 7.49 (s, 1H), 8.28 (br s, 1H), 8.87 (s, 1H); Mass Spectrum: M + H⁺ 455.
[5] The amine starting material was N,N-dimethyl-L-prolinamide. The product gave the following characterising data; NMR Spectrum: (DMSOd$_6$ and CF$_3$CO$_2$D) 1.78–2.0 (m, 2H), 2.09–2.2 (m, 1H), 2.52–2.63 (m, 1H), 2.95 (s, 3H), 3.02 (m, 3H), 3.23–3.36 (m, 2H), 3.51 (m, 1H), 3.86–3.96 (m, 1H), 4.03 (s, 3H), 4.16–4.3 (m, 2H), 4.39–4.48 (m, 1H), 4.85 (m, 1H), 6.09 (s, 2H), 6.93–7.06 (m, 3H), 7.44 (s, 1H), 8.23 (s, 1H), 8.88 (s, 1H); Mass Spectrum: M + H⁺ 510.
[6] The product gave the following characterising data; NMR Spectrum: (DMSOd$_6$ and CF$_3$CO$_2$D) 1.5–2.16 (m, 8H), 3.25–3.44 (m, 2H), 3.65–4.02 (m, 2H), 3.92 (d, 1H), 4.03 (s, 3H), 4.19–4.33 (m, 2H), 4.42–4.57 (m, 1H), 5.55–5.73 (m, 2H), 6.02–6.17 (m, 3H), 6.96–7.03 (m, 3H), 7.41 (s, 1H), 8.18 (s, 1H), 8.89 (s, 1H); Mass Spectrum: M + H⁺ 493.
[7] The product gave the following characterising data; NMR Spectrum: (DMSOd$_6$ and CF$_3$CO$_2$D) 2.86 (br s, 3H), 3.19–3.46 (m, 2H), 3.76–3.98 (m, 2H), 4.03 (s, 3H), 4.25 (d, 2H), 4.42–4.53 (m, 1H), 5.52–5.65 (m, 2H), 5.94–6.06 (m, 1H), 6.08 (s, 2H), 6.94–7.05 (m, 3H), 7.43 (br s, 1H), 8.18 (s, 1H), 8.89 (s, 1H); Mass Spectrum: M − H⁻ 437.
[8] The product gave the following characterising data; NMR Spectrum: (DMSOd$_6$ and CF$_3$CO$_2$D) 1.8.–1.99 (m, 2H), 2.0–2.11 (m, 2H), 3.08–3.22 (m, 2H), 3.33–3.46 (m, 2H), 3.59–3.71 (m, 2H), 4.03 (s, 3H), 4.25 (d, 2H), 4.36–4.45 (m, 1H), 6.16 (d, 2H), 7.07 (d, 1H), 7.16 (d, 1H), 7.49 (s, 1H), 8.24 (s, 1H), 8.91 (s, 1H); Mass Spectrum: M − H⁻ 471 and 473.
The 4-(6-chloro-2,3-methylenedioxyanilino)-7-[(2R)-2,3-epoxypropoxy]-6-methoxyquinazoline used as a starting material was prepared by the reaction of 4-(6-chloro-2,3-methylenedioxyanilino)-7-hydroxy-6-methoxyquinazoline and (2R)-(−)-glycidyl tosylate using an analogous procedure to that described in the portion of Example 23 that is concerned with the preparation of starting materials. The material so obtained gave the following characterising data; NMR Spectrum: (DMSOd$_6$ and CF$_3$CO$_2$D) 2.85 (m, 1H), 2.95 (t, 1H), 3.45 (m, 1H), 4.05 (s, 3H), 4.65 (m, 1H), 6.15 (s, 2H), 7.05 (d, 1H), 7.15 (d, 1H), 7.35 (s, 1H), 8.15 (s, 1H), 8.9 (s, 1H); Mass Spectrum: M − H⁻ 400 and 402.
[9] The product gave the following characterising data; NMR Spectrum: (DMSOd$_6$ and CF$_3$CO$_2$D) 1.31–1.52 (m, 1H), 1.65–1.97 (m, 5H), 2.9–3.13 (m, 2H), 3.19–3.42 (m, 2H), 3.47–3.61 (m, 2H), 4.03 (s, 3H), 4.26 (d, 2H), 4.45–4.59 (m, 1H), 6.16 (s, 2H), 7.07 (d, 1H), 7.16 (d, 1H), 7.49 (s, 1H), 8.24 (s, 1H), 8.91 (s, 1H); Mass Spectrum: M − H⁻ 485 and 487.
[10] The product gave the following characterising data; NMR Spectrum: (DMSOd$_6$ and CF$_3$CO$_2$D) 1.52–1.76 (m, 4H, 1.77–2.02 (m, 4H), 3.15–3.34 (m, 3H), 3.36–3.59 (m, 3H), 4.03 (s, 3H), 4.26 (d, 2H), 4.42–4.57 (m, 1H), 6.52 (s, 2H), 7.06 (d, 1H), 7.16 (d, 1H), 7.53 (s, 1H), 8.29 (s, 1H), 8.9 (s, 1H; Mass Spectrum: M − H⁻ 499 and 501.
[11] The product gave the following characterising data; NMR Spectrum: (DMSOd$_6$ and CF$_3$CO$_2$D) 1.2–1.4 (m, 6H), 2.81 (s, 3H, 3.07–3.74 (m, 3H), 4.04 (s, 3H), 4.27 (d, 2H), 4.4–4.54 (m, 1H), 6.16 (m, 2H), 7.07 (d, 1H), 7.15 (d, 1H), 7.51 (br s, 1H), 8.28 (br s, 1H), 8.9 (s, 1H); Mass Spectrum: M − H⁻ 473 and 475.
[12] The product gave the following characterising data; NMR Spectrum: (DMSOd$_6$ and CF$_3$CO$_2$D) 0.91–1.13 (m, 6H), 2.06–2.22 (m, 1H), 2.91 (s, 3H), 2.92–3.04 (m, 1H), 3.06–3.47 (m, 3H), 4.04 (s, 3H), 4.26 (d, 2H), 4.44–4.61 (m, 1H), 6.16 (s, 2H), 7.07 (d, 1H), 7.16 (d, 1H), 7.51 (s, 1H), 8.28 (s, 1H), 8.9 (s, 1H); Mass Spectrum: M − H⁻ 487 and 489.
[13] The product gave the following characterising data; NMR Spectrum: (DMSOd$_6$ and CF$_3$CO$_2$D) 1.77–2.01 (m, 2H), 2.08–2.22 (m, 1H), 2.53–2.63 (m, 1H), 2.95 (s, 3H), 3.01 (s, 3H), 3.22–3.56 (m, 2H), 3.51 (m, 1H), 3.85–3.96 (m, 1H), 4.03 (s, 3H), 4.17–4.3 (m, 2H), 4.39–4.49 (m, 1H), 4.84 (t, 1H), 6.16 (s, 2H), 7.07 (d, 1H), 7.16 (d, 1H), 7.45 (s, 1H), 8.22 (s, 1H), 8.91 (s, 1H); Mass Spectrum: M − H⁻ 542 and 544.
[14] The product gave the following characterising data; NMR Spectrum: (DMSOd$_6$ and CF$_3$CO$_2$D) 2.83 (br s, 3H), 3.16–3.44 (m, 2H), 3.73–4.0 (m, 2H), 4.03 (s, 3H), 4.26 (d, 2H), 4.42–4.55 (m, 1H), 5.51–5.64 (m, 2H), 5.91–6.02 (m, 1H), 6.16 (s, 2H), 7.07 (d, 1H), 7.16 (d, 1H), 7.50 (br s, 1H), 8.27 (br s, 1H), 8.9 (s, 1H; Mass Spectrum: M − H⁻ 471 and 473.

EXAMPLE 25

4-(2,2-difluoro-1,3-benzodioxol-4-ylamino)-6-methoxy-7-(3-morpholinopropoxy)quinazoline dihydrochloride salt Using an analogous procedure to that described in Example 1, except that isopropanol was used in place of pentan-2-ol as the reaction solvent and the reaction mixture was heated to 80° C. for 3.5 hours, 4-chloro-6-methoxy-7-(3-morpholinopropoxy)quinazoline (0.15 g) was reacted with 2,2-difluoro-1,3-benzodioxol-4-ylamine (0.092 g). The precipitate so obtained was purified by column chromatography on silica using a 19:1 mixture of methylene chloride and a saturated methanolic ammonia solution as eluent. The material so obtained was dissolved in methylene chloride and a 6M solution of hydrogen chloride in diethyl ether was added. The dihydrochloride salt so obtained was isolated and dried to give the title compound (0.045 g); NMR Spectrum: (DMSOd$_6$ and CF$_3$CO$_2$D) 2.35 (m, 2H), 3.15 (m, 2H), 3.35 (m, 2H), 3.55 (d, 2H), 3.8 (t, 2H), 3.9 (m, 2H), 4.0 (s, 3H), 4.35 (t, 2H), 7.35 (m, 2H), 7.45 (m, 2H), 8.3 (s, 1H), 8.95 (s, 1H); Mass Spectrum: M+H⁺ 475.

EXAMPLE 26

6-methoxy-7-[2-(5-methyl-2-morpholinomethylimidazol-1-yl)ethoxy]-4-(2,3-methylenedioxyanilino)quinazoline Di-tert-butyl azodicarboxylate (0.063 g) was added dropwise to a stirred mixture of 7-hydroxy-6-methoxy-4-(2,3-methylenedioxyanilino)quinazoline (0.055 g), 1-(2-hydroxyethyl)-5-methyl-2-morpholinomethylimidazole (0.046 g), triphenylphosphine (0.072 g) and methylene chloride (1 ml). The reaction mixture was stirred at ambient temperature for 2 hours. The resultant precipitate was isolated, washed with methylene chloride and dried under vacuum to give the title compound (0.052 g); NMR Spectrum: (DMSOd$_6$ and CF$_3$CO$_2$D) 2.55 (s, 3H), 3.1 (br s, 4H), 3.8 (br s, 4H), 4.05 (s, 3H), 4.6 (s, 2H), 4.9 (m, 2H), 6.1 (s, 2H), 7.0 (m, 3H), 7.3 (s, 1H), 7.6 (s, 1H), 8.12 (s, 1H), 8.9 (s, 1H); Mass Spectrum: M+H$^+$ 519.

The 1-(2-hydroxyethyl)-5methyl-2-morpholinomethylimidazole used as a starting material was prepared as follows:

A mixture of 4-methyl-1-tritylimidazole (*J. Heterocyclic Chem.*, 1982, 19, 253; 32.5 g), methyl bromoacetate (11.4 ml) and acetone (500 ml) was heated to reflux for 2 hours. The solvent was removed by evaporation and the residue was dissolved in methanol (100 ml) and heated to reflux for 45 minutes. The mixture was evaporated and the residue was triturated under diethyl ether. The resultant precipitate was isolated and stirred at ambient temperature for 1 hour in a mixture of diethyl ether (200 ml) and a saturated methanolic ammonia solution (20 ml). The mixture was filtered and the filtrate was evaporated. The residue was purified by column chromatography on silica using a 49:1 mixture of methylene chloride and methanol as eluent. There was thus obtained methyl 2-(5-methylimidazol-1-yl)acetate (6 g); NMR Spectrum: (CDCl$_3$) 2.16 (s, 3H), 3.78 (s, 3H), 4.61 (s, 3H), 6.8 (s, 1H), 7.42 (s, 1H).

A solution of a portion (1.7 g) of the material so obtained in diethyl ether (20 ml) was added dropwise to a stirred suspension of lithium aluminium hydride (0.76 g) in diethyl ether (70 ml) which was cooled to 0° C. The resultant mixture was stirred at ambient temperature for 1 hour. The mixture was cooled to 0° C. and a 6N aqueous sodium hydroxide solution (0.8 ml) and water (2.4 ml) were added dropwise in turn. The mixture was stirred at ambient temperature for 30 minutes and then evaporated. The residue was dissolved in methylene chloride, dried over magnesium sulphate and evaporated to give 1-(2-hydroxyethyl)-5-methylimidazole (1.1 g); NMR Spectrum: (CDCl$_3$) 2.17 (s, 3H), 3.81 (t, 2H), 3.92 (t, 2H), 6.6 (s, 1H), 7.24 (s, 1H).

Tert-butyldimethylsilyl chloride (9.05 g) was added to a stirred mixture of 1-(2-hydroxyethyl)-5-methylimidazole (6.4 g), imidazole (7.5 g) and methylene chloride (30 ml) which was cooled to 0° C. The reaction mixture was stirred at ambient temperature for 4 hours. The mixture was poured into water. The organic layer was washed with brine, dried over magnesium sulphate and evaporated to give 1-(2-tert-butyldimethylsilyloxyethyl)-5-methylimidazole (11.7 g); NMR Spectrum: (CDCl$_3$)−0.04 (s, 6H), 0.85 (s, 6H), 2.2 (s, 3H), 3.8 (m, 2H), 3.94 (m, 2H), 6.75 (s, 1H), 7.43 (s, 1H).

The material so obtained was dissolved in THF (400 ml) and the solution was cooled at −60° C. n-Butyllithium (2.5M in hexane, 40 ml) was added dropwise and the mixture was stirred at −50° C. for 1 hour. The mixture was cooled to −60° C. and DMF (12.5 ml) was added dropwise. The resultant mixture was allowed to warm to ambient temperature and was stirred for 2 hours. Diethyl ether (500 ml) was added and the reaction mixture was poured into a saturated aqueous ammonium chloride solution. The organic layer was separated, washed with brine, dried over magnesium sulphate and evaporated. The material so obtained was purified by column chromatography on silica using increasingly polar mixtures of methylene chloride and a saturated methanolic ammonia solution as eluent. There was thus obtained 1-(2-tert-butyldimethylsilyloxyethyl)-2-formyl-5-methylimidazole (11 g); NMR Spectrum: (CDCl$_3$) −0.1 (s, 6H), 0.79 (s, 9H), 2.32 (s, 3H), 3.91 (t, 2H), 4.4 (t, 2H), 7.07 (s, 1H), 9.71 (s, 1H).

A portion (0.79 g) of the material so obtained was dissolved in methylene chloride (24 ml) and morpholine (0.263 ml) and acetic acid (0.175 ml) were added. Sodium borohydride triacetate (0.8 g) was added portionwise and the mixture was stirred at ambient temperature for 16 hours. The mixture was evaporated and the residue was purified by column chromatography on silica using a 49:1 mixture of methylene chloride and a saturated methanolic ammonia solution as eluent. There was thus obtained 1-(2-tert-butyldimethylsilyloxyethyl)-5-methyl-2-morpholinomethylimidazole (0.5 g); NMR Spectrum: (CDCl$_3$) 0 (s, 6H), 0.82 (s, 9H), 2.25 (s, 3H), 2.45 (m, 4H), 3.6 (s, 2H), 3.68 (m, 4H), 3.85 (t, 2H), 4.1 (t, 2H), 6.7 (s, 1H).

A mixture of the material so obtained, 12N aqueous hydrochloric acid (0.26 ml) and methanol (10 ml) was stirred at ambient temperature for 5 hours. The mixture was evaporated and the residue was triturated under pentane. The resultant solid was isolated and dried under vacuum. The solid was stirred at ambient temperature for 1 hour in a mixture of methylene chloride and a saturated methanolic ammonia solution. The mixture was filtered and the filtrate was evaporated. The residue was purified by column chromatography on silica using a 19:1 mixture of methylene chloride and a saturated methanolic ammonia solution as eluent. There was thus obtained 1-(2-hydroxyethyl)-5-methyl-2-morpholinomethylimidazole (0.25 g); NMR Spectrum: (CDCl$_3$) 2.2 (s, 3H), 2.6 (br s, 4H), 3.58 (s, 2H), 3.7 (m, 4H), 3.85 (t, 2H), 4.1 (t, 2H), 6.5–6.9 (br s, 1H), 6.65 (s, 1H).

EXAMPLE 27

Using an analogous procedure to that described in Example 26 except that the reaction mixture was stirred at ambient temperature for 16 hours, the appropriate 7-hydroxyquinazoline was reacted with the appropriate alcohol to give the compounds described in Table VI. When each reaction was complete, the reaction mixture was evaporated and the residue was purified by column chromatography on silica using increasingly polar mixtures of methylene chloride and a saturated methanolic ammonia solution as eluent. The product obtained after chromatographic purification was dissolved in diethyl ether and a 6.3M solution of hydrogen chloride in isopropanol was added. The resultant dihydrochloride salt was isolated, washed with diethyl ether and dried under vacuum. Unless otherwise stated, each compound described in Table VI was obtained as a dihydrochloride salt.

TABLE VI

[Structure: quinazoline with MeO- at position 6, R¹ at position 7, and at position 4 an HN linked to a benzodioxole bearing R² at position 6]

| No. & Note | R¹ | R² |
|---|---|---|
| [1] | 2-[2-(N,N-dimethylcarbamoyl)pyrrolidin-1-yl]ethoxy | hydrogen |
| [2] | 2-[2-(N-methylcarbamoyl)pyrrolidin-1-yl]ethoxy | hydrogen |
| [3] | 2-(carbamoylpyrrolidin-1-yl)ethoxy | hydrogen |
| [4] | 2-(2-piperidinocarbonylpyrrolidin-1-yl)ethoxy | hydrogen |
| [5] | 2-(2-morpholinocarbonylpyrrolidin-1-yl)ethoxy | hydrogen |
| [6] | 2-[2-(4-methylpiperazin-1-ylcarbonyl)-pyrrolidin-1-yl]ethoxy | hydrogen |
| [7] | 2-[2-(pyrrolidin-1-ylcarbonyl)pyrrolidin-1-yl]ethoxy | hydrogen |
| [8] | 2-(2-methylpyrrolidin-1-yl)ethoxy | hydrogen |
| [9] | 2-(2-methoxymethylpyrrolidin-1-yl)ethoxy | hydrogen |
| [10] | 3-pyridylmethoxy | hydrogen |
| [11] | 4-pyridylmethoxy | hydrogen |

Notes

[1] The free base was obtained from the chromatographic purification and gave the following data; NMR Spectrum: (DMSOd$_6$ and CF$_3$CO$_2$D) 1.8–1.95 (m, 3H), 2.05–2.2 (m, 1H), 2.7 (s, 3H), 3.0 (s, 3H), 3.35 (m, 1H), 3.8–3.9 (m, 2H), 4.02 (s, 3H), 4.5 (m, 2H), 4.8 (m, 2H), 6.06 (s, 2H), 6.96 (s, 3H), 7.35 (s, 1H), 8.15 (s, 1H), 8.9 (s, 1H); Mass Spectrum: M + H$^+$ 480.

The (2S)-1-(2-hydroxyethyl)-N,N-dimethylpyrrolidine-2-carboxamide used as a starting material was prepared as follows:-
A mixture of 1-(tert-butoxycarbonyl)-L-proline (10.75 g), 1-(3-dimethyl-aminopropyl)-3-ethylcarbodiimide hydrochloride (10.6 g), dimethylamine hydrochloride (5.33 g), 4-dimethylaminopyridine (6.1 g) and methylene chloride (200 ml) was stirred at ambient temperature for 4 hours. The mixture was poured into water. The organic layer was separated, washed in turn with a 1N aqueous potassium hydrogen sulphate solution, with a 5% aqueous sodium bicarbonate solution and brine, dried over magnesium sulphate and evaporated to give 1-(tert-butoxycarbonyl)-N,N-dimethyl-L-prolinamide (11.2 g); NMR Spectrum: (CDCl$_3$) 1.4 and 1.5 (2 s, 9H), 1.8–1.9 (m, 2H), 1.95–2.2 (m, 2H), 3.0 and 3.1 (2 d, 6H), 3.35–3.6 (m, 2H), 4.55 and 4.7 (2 m, 1H).
A mixture of a portion (0.24 g) of the material so obtained and trifluoroacetic acid (3 ml) was stirred at ambient temperature for 2 hours. The mixture was evaporated and the residue was triturated under diethyl ether. A slight excess of a 2M solution of hydrogen chloride in diethyl ether was added and the precipitate was isolated and dried under vacuum to give N,N-dimethyl-L-prolinamide hydrochloride salt (0.25 g); NMR Spectrum: (DMSOd$_6$ and CF$_3$CO$_2$D) 1.7–2.0 (m, 3H), 2.3–2.5 (m, 1H), 2.95 (s, 3H), 3.05 (s, 3H), 3.1–3.4 (m, 2H), 4.6 (m, 1H).
A mixture of N,N-dimethyl-L-prolinamide hydrochloride salt (6.3 g), 2-bromoethanol (3.8 ml), potassium carbonate (14 g) and acetonitrile (70 ml) was stirred and heated to reflux for 16 hours. The mixture was filtered and the filtrate was evaporated. The residue was purified by column chromatography on silica using a 24:1 mixture of methylene chloride and a saturated methanolic ammonia solution as eluent. There was thus obtained (2S)-1-(2-hydroxyethyl)-N,N-dimethylpyrrolidine-2-carboxamide (3.4 g); NMR Spectrum: (CDCl$_3$) 1.6 (m, 1H), 1.6–2.0 (m, 4H), 2.1–2.3 (m, 2H), 2.4 (m, 1H), 2.9 (m, 1H), 3.0 (s, 3H), 3.05 (s, 3H), 3.25–3.4 (m, 2H), 3.75 (m, 1H), 3.9 (m, 1H), 5.1 (br s, 1H); Mass Spectrum: M + H$^+$ 187.

[2] (2S)-1-(2-Hydroxyethyl)-N-methylprolinamide was used as a starting material. The dihydrochloride salt gave the following data; Mass Spectrum: M + H$^+$ 466.
The (2S)-1-(2-hydroxyethyl)-N-methylprolinamide used as a starting material was obtained as follows:-
A mixture of 1-(tert-butoxycarbonyl)-L-proline (5.4 g), 1-(3-dimethylaminopropyl)-3-ethylcarbodiimide (5.3 g), methylamine hydrochloride (2.2 g), 4-dimethylaminopyridine (3 g) and methylene chloride (50 ml) was stirred at ambient temperature for 16 hours. The resultant mixture was poured in water and the organic layer was separated, washed in turn with a 1M aqueous potassium hydrogen sulphate solution, a saturated aqueous sodium bicarbonate solution and brine, dried over magnesium sulphate and evaporated. There was thus obtained 1-(tert-butoxycarbonyl)-N-methyl-L-prolinamide (5.6 g); Mass Spectrum: M + H$^+$ 229.
A mixture of a portion (4.4 g) of the material so obtained and trifluoroacetic acid (10 ml) was stirred at ambient temperature for 2 hours. The mixture was evaporated and the residue was triturated under diethyl ether. The resultant solid was isolated, washed with diethyl ether and dried under vacuum. There was thus obtained to give N-methyl-L-prolinamide trifluoroacetic acid salt (3.7 g); NMR Spectrum: (DMSOd$_6$ and CF$_3$CO$_2$D) 1.85–2.05 (m, 3H), 2.2–2.3 (m, 1H), 2.73 (s, 3H), 3.2–3.4 (m, 2H), 4.2 (m, 1H).
A mixture of a portion (2.5 g) of the material so obtained, 2-bromoethanol (2.15 ml), potassium carbonate (5.5 g) and acetonitrile (20 ml) was stirred and heated to reflux for 18 hours. The mixture was cooled to ambient temperature, filtered and evaporated and the residue was purified by column chromatography on silica using a 49:1 mixture of methylene chloride and a saturated methanolic ammonia solution as eluent. There was thus obtained (2S)-1-(2-hydroxyethyl)-N-methyl-prolinamide (0.5 g); NMR Spectrum: (CDCl$_3$) 1.6–2.0 (m, 4H), 2.1–2.3 (m, 1H), 2.3–2.45 (m, 1H), 2.6–2.7 (m, 1H), 2.85 (d, 3H), 2.8–2.9 (m, 1H), 3.1–3.2 (m, 1H), 3.2–3.3 (m, 1H), 3.6–3.8 (m, 2H); Mass Spectrum: M + H$^+$ 173.

[3] (2S)-1-(2-Hydroxyethyl)prolinamide was used as a starting material. The dihydrochloride salt gave the following data; NMR Spectrum: (DMSOd$_6$ and CF$_3$CO$_2$D) 1.75–2.02(m, 2H), 2.03–2.19 (m, 1H), 2.56–2.67 (m, 1H), 3.3–3.43 (m, 1H), 3.7-3.91 (m, 3H), 4.03 (s, 3H), 4.28–4.43 (m, 1H), 4.45–4.65 (m, 2H), 6.08 (s, 2H), 6.94–7.04 (m, 3H), 7.42 (s, 1H), 8.21 (s, 1H), 8.88 (s, 1H); Mass Spectrum: M + H$^+$ 452.
The (2S)-1-(2-hydroxyethyl)prolinamide used as a starting material was prepared by the reaction of L-prolinamide and 2-bromoethanol using an analogous procedure to that described in Note [2] immediately above.
There was thus obtained the required starting material; NMR Spectrum: (CDCl$_3$) 1.6–2.0 (m, 4H), 2.1–2.25 (m, 1H), 2.35–2.45 (m, 1H), 2.6–2.7 (m, 1H), 2.8–3.0 (m, 1H), 3.1 (m, 1H), 3.2–3.3 (m, 1H), 3.6–3.8 (m, 2H), 5.6 (br s, 1H), 7.4 (br s, 1H); Mass Spectrum: M + H$^+$ 159.

[4] (2S)-1-(2-Hydroxyethyl)-2-piperidinocarbonylpyrrolidine was used as a starting material. The dihydrochloride salt gave the following data; NMR Spectrum: (DMSOd$_6$ and CF$_3$CO$_2$D) 1.28–1.75 (m, 7H), 1.76–1.99 (m, 2H), 2.02–2.25 (m, 1H), 3.02–3.19 (m, 1H), 3.22–3.5 (m, 3H), 3.53–3.65 (m, 1H), 3.68–3.9 (m, 3H), 4.04 (s, 3H), 4.44–4.63 (m, 2H), 4.74–4.89 (m, 1H), 6.36 (s, 2H), 6.91–7.07 (m, 3H), 7.45 (s, 1H), 8.25 (s, 1H), 8.89 (s, 1H); Mass Spectrum: M + H$^+$ 520.
The (2S)-1-(2-hydroxyethyl)-2-piperidinocarbonylpyrrolidine used as a starting material was prepared as follows:-
Using analogous procedures to those described in Note [2] immediately above, 1-(tert-butoxycarbonyl)-L-proline was reacted with piperidine to give (2S)-1-(tert-butoxycarbonyl)-2-piperidinocarbonylpyrrolidine which was deprotected and reacted with 2-bromoethanol. There was thus obtained the required starting material; NMR Spectrum: (CDCl$_3$) 1.5–1.9 (m, 10H), 1.9–2.0 (m, 1H), 2.1–2.2 (m, 1H), 2.4–2.5 (m, 1H), 2.55–2.65 (m, 1H), 2.8–2.9 (m, 1H), 3.3–3.7 (m, 6H), 4.3 (br s, 1H; Mass Spectrum: M + H$^+$ 227.

[5] (2S)-1-(2-Hydroxyethyl)-2-morpholinocarbonylpyrrolidine was used as a starting material. The dihydrochloride salt gave the following data; NMR Spectrum: (DMSOd$_6$ and CF$_3$CO$_2$D) 1.3–1.5 (m, 2H), 1.8–2.0 (m, 3H), 2.15 (m, 1H), 3.2 (m, 1H), 3.3–3.9 (m, 8H), 4.05 (s, 3H), 4.55 (m, 2H), 4.8 (m, 1H), 6.1 (s, 2H), 7.0 (m, 3H), 7.4 (s, 1H), 8.2 (s, 1H), 8.9 (s, 1H); Mass Spectrum: M + H$^+$ 522.
The (2S)-1-(2-hydroxyethyl)-2-morpholinocarbonylpyrrolidine used as a starting material was prepared as follows:-
Using analogous procedures to those described in Note [2] immediately above, 1-(tert-butoxycarbonyl)-L-proline was reacted with morpholine to give (2S)-1-(tert-butoxycarbonyl)-2-morpholinocarbonylpyrrolidine which was deprotected and reacted with 2-bromoethanol. There was thus obtained the required starting material; NMR Spectrum: (CDCl$_3$) 1.7–2.0 (m, 4H), 2.1–2.2 (m, 1H), 2.4–2.5 (m, 1H), 2.6–2.7 (m, 1H), 2.8–2.9 (m, 1H), 3.3–3.4 (m, 2H), 3.4–3.8 (m, 10H); Mass Spectrum: M + H$^+$ 229.

[6] (2S)-1-(2-Hydroxyethyl)-2-(4-methylpiperazin-1-ylcarbonyl)-pyrrolidine was used as a starting material. The free base was obtained from the chromatographic purification and gave the following data; NMR Spectrum: (CDCl$_3$) 1.41–1.49 (m, 2H), 1.81–1.91 (m, 2H), 1.92–2.02 (m, 1H), 2.09–2.2 (m, 1H), 2.28 (s, 3H), 2.29–2.36 (m, 2H), 2.37–2.48 (m, 2H), 2.49–2.57 (m, 1H), 2.93–3.03 (m, 1H), 3.19–3.28 (m, 1H), 3.35–3.42 (m, 1H), 3.56–3.77(m, 3H), 4.01 (s, 3H), 4.25–4.38 (m, 2H), 6.03 (s, 2H), 6.4–6.45 (m, 1H), 6.69 (d, 1H), 6.91 (m, 1H), 7.04 (s, 1H), 7.24 (s, 1H),

TABLE VI-continued 7.52 (d, 1H); Mass Spectrum: M + H⁺ 535.
The (2S)-1-(2-hydroxyethyl)-2-(4-methylpiperazin-1-ylcarbonyl)-pyrrolidine used as a starting material was prepared as follows:-
Using analogous procedures to those described in Note [2] immediately above, 1-(tert-butoxycarbonyl)-L-proline was reacted with 1-methylpiperazine to give (2S)-1-(tert-butoxycarbonyl)-2-(4-methylpiperazin-1-ylcarbonyl)pyrrolidine which was deprotected and reacted with 2-bromoethanol. There was thus obtained the required starting material; NMR Spectrum: (CDCl$_3$) 1.7–2.05 (m, 4H), 2.1–2.25 (m, 1H), 2.32 (s, 3H), 2.35–2.5 (m, 4H), 2.6–2.7 (m, 1H), 2.8–2.9 (m, 1H), 3.3–3.7 (m, 8H), 4.15 (br s, 1H); Mass Spectrum: M + H⁺ 242.
[7] (2S)-1-(2-Hydroxyethyl)-2-(pyrrolidin-1-ylcarbonyl)pyrrolidine was used as a starting material. The dihydrochloride salt gave the following data; NMR Spectrum: (DMSOd$_6$ and CF$_3$CO$_2$D) 1.29–1.52 (m, 2H), 1.55–2.03 (m, 5H), 2.07–2.23 (m, 1H), 2.93–3.08 (m, 1H), 3.18–3.45 (m, 3H), 3.46–3.59 (m, 1H), 3.72–3.93 (m, 3H), 4.03 (s, 3H), 4.43–4.71 (m, 3H), 6.09 (s, 2H), 7.94–7.06 (m, 3H), 7.39 (s, 1H), 8.2 (s, 1H), 8.89 (s, 1H); Mass Spectrum: M − H⁻ 504.
The (2S)-1-(2-hydroxyethyl)-2-(pyrrolidin-1-ylcarbonyl)pyrrolidine used as a starting material was prepared as follows:-
Using analogous procedures to those described in Note [2] immediately above, 1-(tert-butoxycarbonyl)-L-proline was reacted with pyrrolidine to give (2S)-1-(tert-butoxycarbonyl)-2-(pyrrolidin-1-ylcarbonyl)pyrrolidine which was deprotected and reacted with 2-bromoethanol. There was thus obtained the required starting material; NMR Spectrum: (CDCl$_3$) 1.7–2.05 (m, 8H), 2.1–2.3 (m, 1H), 2.4–2.5 (m, 1H), 2.55–2.7 (m, 1H), 2.8–2.9 (m, 1H), 3.2–3.3 (m, 2H), 3.4–3.7 (m, 5H), 4.1 (br s, 1H); Mass Spectrum: M + H⁺ 213.
[8] (2R)-1-(2-Hydroxyethyl)-2-methylpyrrolidine was used as a starting material. The dihydrochloride salt gave the following data; NMR Spectrum: (DMSOd$_6$ and CF$_3$CO$_2$D) 1.45 (d, 3H), 1.6–1.7 (m, 1H), 1.9–2.1 (m, 2H), 2.1–2.3 (m, 1H), 3.35 (m, 1H), 3.5–3.7 (m, 2H), 3.7–3.8 (m, 1H), 3.9 (m, 1H), 4.05 (s, 3H), 4.6 (br s, 2H), 6.1 (s, 2H), 7.0 (s, 3H), 7.45 (s, 1H), 8.25 (s, 1H), 8.9 (s, 1H); Mass Spectrum: M + H⁺ 423.
The (2R)-1-(2-hydroxyethyl)-2-methylpyrrolidine used as a starting material was obtained as follows:-
A mixture of (2R)-2-methylpyrrolidine (0.853 g), 2-bromoethanol (1.1 ml), potassium carbonate (2.8 g) and acetonitrile (10 ml) was stirred and heated to reflux for 18 hours. The mixture was filtered and the filtrate was evaporated. The resultant residue was purified by column chromatography on silica using a 49:1 mixture of methylene chloride and a saturated methanolic ammonia solution as eluent. There was thus obtained (2R)-1-(2-hydroxyethyl)-2-methylpyrrolidine (0.35 g); NMR Spectrum: (CDCl$_3$) 1.1 (d, 3H), 1.3–1.5 (m, 1H), 1.6–1.8 (m, 3H), 1.95 (m, 1H), 2.15 (m, 1H), 2.28 (m, 1H), 2.4–2.5 (m, 1H), 2.95–3.05 (m, 1H), 3.2 (m, 1H), 3.5–3.8 (m, 2H); Mass Spectrum: M + H⁺ 130.
[9] (2S)-1-(2-Hydroxyethyl)-2-methoxymethylpyrrolidine was used as a starting material. The dihydrochloride salt gave the following data; NMR Spectrum: (DMSOd$_6$ and CF$_3$CO$_2$D) 1.4–1.5 (m, 1H), 1.65–1.8 (m, 1H), 1.8–2.0 (m, 1H), 2.0–2.12 (m, 1H), 2.12–2.25 (m, 1H), 3.35 (s, 3H), 3.7 (m, 4H), 3.8–4.0 (m, 2H), 4.05 (s, 3H), 4.6 (m, 2H), 6.1 (s, 2H), 7.0 (m, 3H), 7.45 (s, 1H), 8.25 (s, 1H), 8.9 (s, 1H); Mass Spectrum: M + H⁺ 453.
The (2S)-1-(2-hydroxyethyl)-2-methoxymethylpyrrolidine used as a starting material was obtained as follows:-
Using an analogous procedure to those described in Note [8] immediately above, (2S)-2-methoxymethylpyrrolidine was reacted with 2-bromoethanol to give (2S)-1-(2-hydroxyethyl)-2-methoxymethyl-pyrrolidine; NMR Spectrum: (CDCl$_3$) 1.5–1.65 (m, 1H), 1.65–1.8 (m, 2H), 1.8–2.0 (m, 2H), 2.3 (m, 1H), 2.6 (m, 1H), 2.8 (m, 1H), 2.95–3.05 (m, 1H), 3.17 (m, 1H), 3.3 (t, 1H), 3.35 (t, 1H), 3.37 (s, 3H), 3.5–3.7 (m, 2H).
[10] The dihydrochloride salt gave the following data; NMR Spectrum: (DMSOd$_6$ and CF$_3$CO$_2$D) 4.05 (s, 3H), 5.6 (s, 2H), 6.1 (s, 2H), 7.0 (s, 3H), 7.6 (s, 1H), 8.2 (m, 1H), 8.3 (s, 1H), 8.8 (d, 1H), 8.9 (s, 1H), 9.05 (d, 1H), 9.2 (s, 1H); Mass Spectrum: M + H⁺ 403.
[11] The dihydrochloride salt gave the following data; NMR Spectrum: (DMSOd$_6$ and CF$_3$CO$_2$D) 4.1 (s, 3H), 5.75 (s, 2H), 6.1 (s, 2H), 7.0 (s, 3H), 7.5 (s, 1H), 8.2 (d, 2H), 8.3 (s, 1H), 8.9 (s, 1H), 9.05 (d, 2H); Mass Spectrum: M + H⁺ 403.

EXAMPLE 28

Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium | 1.5 |

| (e) Injection I | (50 mg/ml) |
|---|---|
| Compound X | 5.0% w/v |
| 1M Sodium hydroxide solution | 15.0% v/v |
| 0.1M Hydrochloric acid | |
| (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

-continued

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:

1. A quinazoline derivative of the Formula I

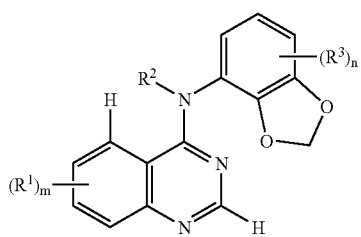

I wherein m is 0, 1, 2 or 3;

each $R^1$ group, which may be the same or different, is located at the 6- and/or 7-positions of the quinazoline ring and is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$Q^1$-$X^1$— wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein adjacent carbon atoms in any (2–6C) alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1–6C)alkyl or, when the inserted group is $N(R^5)$, $R^5$ may also be (2–6C)alkanoyl, and wherein any $CH_2$=CH— or HC≡C— group within a $R^1$ substituent optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^2$-$X^2$— wherein $X^2$ is a direct bond or is selected from CO and $N(R^6)CO$, wherein $R^6$ is hydrogen or (1–6C) alkyl, and $Q^2$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^3$-$Q^3$ wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C) alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C) alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^4$—$R^8$ wherein $X^4$ is a direct bond or is selected from O and N($R^9$), wherein $R^9$ is hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, or from a group of the formula:

—$X^5$-$Q^4$ wherein $X^5$ is a direct bond or is selected from O, N($R^{10}$) and CO, wherein $R^{10}$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and wherein any heterocyclyl group within a substituent on $R^1$ optionally bears 1 or 2 oxo or thioxo substituents;

$R^2$ is hydrogen or (1–6C)alkyl;

n is 0, 1, 2 or 3; and $R^3$ is halogeno, trifluoromethyl, cyano, nitro, hydroxy, amino, carboxy, carbamoyl, (1–6C)alkyl, (2–8C)alkenyl, (2–6C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^6$—$R^{11}$ wherein $X^6$ is a direct bond or is selected from O and N($R^{12}$), wherein $R^{12}$ is hydrogen or (1–6C)alkyl, and $R^{11}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^7$-$Q^5$ wherein $X^7$ is a direct bond or is selected from O, S, SO, $SO_2$, N($R^{13}$), CO, CH(O$R^{13}$), CON($R^{13}$), N($R^{13}$)CO, $SO_2$N($R^{13}$), N($R^{13}$)$SO_2$, C($R^{13}$)$_2$O, C($R^{13}$)$_2$S and N($R^{13}$)C($R^{13}$)$_2$, wherein $R^{13}$ is hydrogen or (1–6C)alkyl, and $Q^5$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and any heterocyclyl group within $Q^5$ optionally bears 1 or 2 oxo or thioxo substituents, or a pharmaceutically-acceptable salt thereof.

2. A quinazoline derivative of the Formula I according to claim 1, or a pharmaceutically-acceptable salt thereof, wherein each of $R^2$, n and $R^3$ has any of the meanings defined in claim 1, m is 1 or 2, and each $R^1$ group, which may be the same or different, is selected from halogeno, trifluoromethyl, hydroxy, amino, carbamoyl, (1–6C)alkyl, (2–8C)alkenyl, (2–8C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino and N-(1–6C)alkyl-(3–6C)alkynoylamino, or from a group of the formula:

$Q^1$-$X^1$— wherein $X^1$ is a direct bond or is selected from O, N($R^4$), CON($R^4$), N($R^4$)CO and OC($R^4$)$_2$ wherein $R^4$ is hydrogen or (1–6C)alkyl, and $Q^1$ is aryl, aryl-(1–6C)alkyl, cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C) alkylene chain within a $R^1$ substituent are optionally separated by the insertion into the chain of a group selected from O, N($R^5$), CON($R^5$), N($R^5$)CO, CH=CH and C≡C wherein $R^5$ is hydrogen or (1–6C)alkyl, or, when the inserted group is N($R^5$), $R^5$ may also be (2–6C)alkanoyl, and wherein any $CH_2$=CH— or HC≡C— group within a $R^1$ substituent optionally bears at the terminal $CH_2$= or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^2$-$X^2$— wherein $X^2$ is a direct bond or is CO or N($R^6$)CO wherein $R^6$ is hydrogen or (1–6C)alkyl, and $Q^2$ is heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group a substituent selected from hydroxy, amino, (1–6C)alkoxy, (1–6C)alkylsulphonyl, (1–6C)alkylamino, di-[(1–6C)alkyl]amino, (2–6C)alkanoyloxy, (2–6C)alkanoylamino and N-(1–6C)alkyl-(2–6C)alkanoylamino, or from a group of the formula:

—X³-Q³ wherein X³ is a direct bond or is selected from O, N(R⁶), CON(R⁷), N(R⁷)CO and C(R⁷)₂O, wherein R⁷ is hydrogen or (1–6C)alkyl, and Q³ is heteroaryl, heteroaryl-(1–6C)alkyl, heterocyclyl or heterocyclyl-(1–6C)alkyl, and wherein any aryl, heteroaryl or heterocyclyl group within a substituent on R¹ optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or optionally bears 1 substituent selected from a group of the formula:

—X⁴—R⁸ wherein X⁴ is a direct bond or is selected from O and N(R⁹), wherein R⁹ is hydrogen or (1–6C)alkyl, and R⁸ is hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, and from a group of the formula:

—X⁵-Q⁴ wherein X⁵ is a direct bond or is selected from O, N(R¹⁰) and CO, wherein R¹⁰ is hydrogen or (1–6C)alkyl, and Q⁴ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on R¹ optionally bears 1 or 2 oxo substituents.

3. A quinazoline derivative of the Formula I according to claim 1, or a pharmaceutically-acceptable salt thereof, wherein each of R², n and R³ has any of the meanings defined in claim 1, m is 2 and each R¹ group, which may be the same or different, is located at the 6- and/or 7-positions and is selected from hydroxy, amino, methyl, ethyl, methoxy, ethoxy, propoxy, isopropoxy, butoxy, methylamino, ethylamino, dimethylamino, diethylamino, acetamido, propionamido, benzyloxy, 2-pyrrol-1-ylethoxy, 3-pyrrol-1-ylpropoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, 2-pyridylmethoxy, 3-pyridylmethoxy, 4-pyridylmethoxy, 2-tetrahydropyran-4-ylethoxy, 3-tetrahydropyran-4-ylpropoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy or 3-homopiperazin-1-ylpropoxy, and wherein adjacent carbon atoms in any (2–6C)alkylene chain within a R¹ substituent are optionally separated by the insertion into the chain of a group selected from O, NH, CH=CH and C≡C, and wherein any CH₂ or CH₃ group within a R¹ substituent optionally bears on each said CH₂ or CH₃ group a substituent selected from hydroxy, amino, methoxy, methylsulphonyl, methyl amino, dimethylamino, diethylamino, diisopropylamino, N-ethyl-N-methylamino, N-isopropyl-N-methylamino, N-isobutyl-N-methylamino, N-allyl-N-methylamino, acetoxy, acetamido, N-methylacetamido, 2-pyridyloxy, 3-pyridyloxy and 4-pyridyloxy, and wherein any phenyl, pyrrolyl, imidazolyl, triazolyl, pyridyl or heterocyclyl group within a substituent on R¹ optionally bears 1, 2 or 3 substituents, which may be the same or different, selected from fluoro, chloro, trifluoromethyl, cyano, hydroxy, amino, carbamoyl, methyl, ethyl, N-methylcarbamoyl, N,N-dimethylcarbamoyl, methoxy, methoxymethyl and morpholinomethyl, and a pyrrolidin-2-yl, piperidin-3-yl, piperidin-4-yl, piperazin-1-yl or homopiperazin-1-yl group within a R¹ substituent is optionally N-substituted with methyl, ethyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on R¹ optionally bears 1 or 2 oxo substituents.

4. A quinazoline derivative of the Formula I according to claim 1, or a pharmaceutically-acceptable salt thereof, wherein each of m, R¹, n and R³ has any of the meanings defined in claim 1, and R² is hydrogen.

5. A quinazoline derivative of the Formula I according to claim 1, or a pharmaceutically-acceptable salt thereof, wherein each of m, R¹ and R² has any of the meanings defined in claim 1, n is 1 or 2 and the R³ groups, which may be the same or different, are located at the 5- and/or 6-positions of the 2,3-methylenedioxyphenyl group and are selected from halogeno, trifluoromethyl, cyano, hydroxy, (1–6C)alkyl, (2–8C)alkenyl, (2–8C)alkynyl and (1–6C)alkoxy.

6. A quinazoline derivative of the Formula I according to claim 1, or a pharmaceutically-acceptable salt thereof, wherein each of m, R¹ and R² has any of the meanings defined in claim 1 and n is 0.

7. A quinazoline derivative of the Formula I according to claim 1 wherein:

m is 1 or 2 and each R¹ group, which may be the same or different, is located at the 6- and/or 7-positions and is selected from hydroxy, amino, methyl, ethyl, propyl, butyl, methoxy, ethoxy, propoxy, isopropoxy, butoxy, methylamino, ethylamino, dimethylamino, diethylamino, acetamido, propionamido, 2-imidazol-1-ylethoxy, 2-(1,2,4-triazol-1-yl)ethoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy and 3-homopiperazin-1-ylpropoxy, and wherein adjacent carbon atoms in any (2–6C) alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino, dimethylamino, diethylamino, N-ethyl-N-methylamino, N-isopropyl-N-methylamino, N-methyl-N-propylamino and acetoxy;

and wherein any heteroaryl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, methoxy, N-methylcarbamoyl and N,N-dimethylcarbamoyl and a pyrrolidin-2-yl, piperidin-3-yl, piperidin-4-yl, piperazin-1-yl or homopiperazin-1-yl group within a $R^1$ substituent is optionally N-substituted with 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

$R^2$ is hydrogen;

n is 0 or 1 and the $R^3$ group, if present, is located at the 5- or 6-position of the 2,3-methylenedioxyphenyl group and is selected from fluoro, chloro, trifluoromethyl, cyano, hydroxy, methyl, ethyl, vinyl, allyl, ethynyl, methoxy and ethoxy;

or a pharmaceutically-acceptable acid-addition salt thereof.

8. A quinazoline derivative of the Formula I according to claim 1 wherein:

m is 2 and each $R^1$ group, which may be the same or different, is located at the 6- and/or 7-positions and is selected from hydroxy, amino, methyl, ethyl, methoxy, ethoxy, propoxy, isopropoxy, butoxy, methylamino, ethylamino, dimethylamino, diethylamino, acetamido, propionamido, benzyloxy, 2-pyrrol-1-ylethoxy, 3-pyrrol-1-ylpropoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, 2-pyridylmethoxy, 3-pyridylmethoxy, 4-pyridylmethoxy, 2-tetrahydropyran-4-ylethoxy, 3-tetrahydropyran-4-ylpropoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy or 3-homopiperazin-1-ylpropoxy, and wherein adjacent carbon atoms in any (2–6C) alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino, dimethylamino, diethylamino, diisopropylamino, N-ethyl-N-methylamino, N-isopropyl-N-methylamino, N-isobutyl-N-methylamino, N-allyl-N-methylamino, acetoxy, acetamido, N-methylacetamido, 2-pyridyloxy, 3-pyridyloxy and 4-pyridyloxy, and wherein any phenyl, pyrrolyl, imidazolyl, triazolyl, pyridyl or heterocyclyl group within a substituent on $R^1$ optionally bears 1, 2 or 3 substituents, which may be the same or different, selected from fluoro, chloro, trifluoromethyl, cyano, hydroxy, amino, carbamoyl, methyl, ethyl, N-methylcarbamoyl, N,N-dimethylcarbamoyl, methoxy, methoxymethyl and morpholinomethyl, and a pyrrolidin-2-yl, piperidin-3-yl, piperidin-4-yl, piperazin-1-yl or homopiperazin-1-yl group within a $R^1$ substituent is optionally N-substituted with methyl, ethyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

$R^2$ is hydrogen;

n is 0 or 1 and the $R^3$ group, if present, is located at the 6-position of the, 2,3-methylenedioxyphenyl group and is selected from chloro, bromo and trifluoromethyl;

or a pharmaceutically-acceptable acid-addition salt thereof.

9. A quinazoline derivative of the Formula I according to claim 1 wherein:
m is 2 and
the first $R^1$ group is located at the 6-position and is selected from hydroxy, methoxy, ethoxy and propoxy, and
the second $R^1$ group is located at the 7-position and is selected from 2-dimethylaminoethoxy, 3-dimethylaminopropoxy, 4-dimethylaminobutoxy, 2-diethylaminoethoxy, 3-diethylaminopropoxy, 4-diethylaminobutoxy, 2-diisopropylaminoethoxy, 3-diisopropylaminopropoxy, 4-diisopropylaminobutoxy, 2-(N-isopropyl-N-methylamino)ethoxy, 3-(N-isopropyl-N-methylamino)propoxy, 4-(N-isopropyl-N-methylamino)butoxy, 2-pyrrolidin-1-ylethoxy, 3-pyrrolidin-1-ylpropoxy, 4-pyrrolidin-1-ylbutoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 4-(4-methylpiperazin-1-yl)butoxy, 2-(4-cyanomethylpiperazin-1-yl)ethoxy, 3-(4-cyanomethylpiperazin-1-yl)propoxy, 4-(4-cyanomethylpiperazin-1-yl)butoxy, 2-[2-(4-methylpiperazin-1-yl)ethoxy]ethoxy, 2-methylsulphonylethoxy and 3-methylsulphonylpropoxy,
and wherein any $CH_2$ group within the second $R^1$ group that is attached to two carbon atoms optionally bears a hydroxy group or acetoxy group on said $CH_2$ group,
and wherein any heterocyclyl group within the second $R^1$ group optionally bears 1 or 2 oxo substituents;
$R^2$ is hydrogen; and
n is 0 or
n is 1 and the $R^3$ group is located at the 5- or 6-position of the 2,3-methylenedioxyphenyl group and is selected from fluoro, chloro, trifluoromethyl, cyano, methyl, ethyl, ethynyl, methoxy and ethoxy;
or a pharmaceutically-acceptable acid-addition salt thereof.

10. A quinazoline derivative of the Formula I according to claim 1 wherein:
m is 2 and
the first $R^1$ group is a 6-methoxy group and
the second $R^1$ group is located at the 7-position and is selected from 2-dimethylaminoethoxy, 3-dimethylaminopropoxy, 4-dimethylaminobutoxy, 2-diethylaminoethoxy, 3-diethylaminopropoxy, 4-diethylaminobutoxy, 2-diisopropylaminoethoxy, 3-diisopropylaminopropoxy, 4-diisopropylaminobutoxy, 2-(N-isopropyl-N-methylamino)ethoxy, 3-(N-isopropyl-N-methylamino)propoxy, 4-(-isopropyl-N-methylamino)butoxy, 2-(N-isobutyl-N-methylamino)ethoxy, 3-(-isobutyl-N-methylamino)propoxy, 4-(N-isobutyl-N-methylamino)butoxy, 2-(N-allyl-N-methylamino)ethoxy, 3-(N-allyl-N-methylamino)propoxy, 4-(N-allyl-N-methylamino)butoxy, 2-pyrrolidin-1-ylethoxy, 3-pyrrolidin-1-ylpropoxy, 4-pyrrolidin-1-ylbutoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, N-cyanomethylpiperidin-3-ylmethoxy, piperidin-4-ylmethoxy, N-methylpiperidin-4-ylmethoxy, N-cyanomethylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-homopiperidin-1-ylethoxy, 3-homopiperidin-1-ylpropoxy, 4-homopiperidin-1-ylbutoxy, 2-piperazin-1-ylethoxy, 2-(4-methylpiperazin-1-yl)ethoxy, 3-piperazin-1-ylpropoxy, 3-(4-methylpiperazin-1-yl)propoxy, 4-piperazin-1-ylbutoxy, 4-(4-methylpiperazin-1-yl)butoxy, 2-(4-cyanomethylpiperazin-1-yl)ethoxy, 3-(4-cyanomethylpiperazin-1-yl)propoxy, 4-(4-cyanomethylpiperazin-1-yl)butoxy, 2-(2-piperazin-1-ylethoxy)ethoxy, 2-[2-(4-methylpiperazin-1-yl)ethoxy]ethoxy, 2-methylsulphonylethoxy, 3-methylsulphonylpropoxy, 2-tetrahydropyran-4-ylethoxy, 3-tetrahydropyran-4-ylpropoxy, 2-pyrrol-1-ylethoxy, 3-pyrrol-1-ylpropoxy, 2-(2-pyridyloxy)ethoxy, 3-(2-pyridyloxy)propoxy, 2-(3-pyridyloxy)ethoxy, 3-(3-pyridyloxy)propoxy, 2-(4-pyridyloxy)ethoxy, 3-(4-pyridyloxy)propoxy, 2-pyridylmethoxy, 3-pyridylmethoxy and 4-pyridylmethoxy,
and wherein any $CH_2$ group within the second $R^1$ group that is attached to two carbon atoms optionally bears a hydroxy group on said $CH_2$ group,
and wherein any heteroaryl group within the second $R^1$ group optionally bears 1 or 2 substituents selected from chloro, cyano, hydroxy and methyl,
and any heterocyclyl group within the second $R^1$ group optionally bears 1 or 2 substituents selected from hydroxy, methyl and oxo;
$R^2$ is hydrogen; and
n is 0 or
n is 1 and the $R^3$ group is located at the 6-position of the 2,3-methylenedioxyphenyl group and is selected from chloro and bromo;
or a pharmaceutically-acceptable acid-addition salt thereof.

11. A quinazoline derivative of the Formula I according to claim 1 wherein:
m is 2 and
the first $R^1$ group is a 6-methoxy group and
the second $R^1$ group is located at the 7-position and is selected from 2-pyrrolidin-1-ylethoxy, 3-pyrrolidin-1- ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 2-(4-cyanomethylpiperazin-1-yl)ethoxy, 3-(4-cyanomethylpiperazin-1-yl)propoxy, 2-[2-(4-methylpiperazin-1-yl)ethoxy]ethoxy, 2-methylsulphonylethoxy, 3-methylsulphonylpropoxy, 2-(4-pyridyloxy)ethoxy, 3-pyridylmethoxy and 2-cyanopyrid-4-ylmethoxy;

$R^2$ is hydrogen; and n is 0 or n is 1 and the $R^3$ group is located at the 6-position of the 2,3-methylenedioxyphenyl group and is selected from chloro and bromo;

or a pharmaceutically-acceptable acid-addition salt thereof.

12. A quinazoline derivative of the Formula I according to claim 1 wherein:

m is 2 and the first $R^1$ group is a 6-methoxy group and the second $R^1$ group is located at the 7-position and is selected from 3-(N-isopropyl-N-methylamino)propoxy, 3-pyrrolidin-1-ylpropoxy, 3-morpholinopropoxy, 3-(1,1-dioxotetrahydro-4H-1,4-thiazin-4-yl)propoxy, 3-piperidinopropoxy, N-methylpiperidin-4-ylmethoxy, 2-(4-methylpiperazin-1-yl)ethoxy, 3-(4-methylpiperazin-1-yl)propoxy, 3-(4-cyanomethylpiperazin-1-yl)propoxy and 2-[2-(4-methylpiperazin-1-yl)ethoxy]ethoxy, and wherein any $CH_2$ group within the second $R^1$ group that is attached to two carbon atoms optionally bears a hydroxy group on said $CH_2$ group;

$R^2$ is hydrogen; and n is 0;

or a pharmaceutically-acceptable acid-addition salt thereof.

13. A quinazoline derivative of the Formula I according to claim 1 selected from:

6-methoxy-4-(2,3-methylenedioxyanilino)-7-(3-morpholinopropoxy)quinazoline, 6-methoxy-4-(2,3-methylenedioxyanilino)-7-[3-(1,1-dioxotetrahydro-4H-1,4-thiazin-4-yl)propoxy]quinazoline, 6-methoxy-4-(2,3-methylenedioxyanilino)-7-(3-pyrrolidin-1-ylpropoxy)quinazoline, 6-methoxy-4-(2,3-methylenedioxyanilino)-7-[2-(4-methylpiperazin-1-yl)ethoxy]quinazoline, 6-methoxy-4-(2,3-methylenedioxyanilino)-7-[3-(4-methylpiperazin-1-yl)propoxy]quinazoline, 6-methoxy-4-(2,3-methylenedioxyanilino)-7-(3-piperidinopropoxy)quinazoline, 6-methoxy-4-(2,3-methylenedioxyanilino)-7-(N-methylpiperidin-4-ylmethoxy)quinazoline, 7-(2-hydroxy-3-pyrrolidin-1-ylpropoxy)-6-methoxy-4-(2,3-methylenedioxyanilino)quinazoline, 7-[2-hydroxy-3-(N-isopropyl-N-methylamino)propoxy]-6-methoxy-4-(2,3-methylenedioxyanilino)quinazoline, 7-[3-(4-cyanomethylpiperazin-1-yl)-2-hydroxypropoxy]-6-methoxy-4-(2,3-methylenedioxyanilino)quinazoline, 6-methoxy-4-(2,3-methylenedioxyanilino)-7-{2-[2-(4-methylpiperazin-1-yl)ethoxy]ethoxy}quinazoline, 4-(6-chloro-2,3-methylenedioxyanilino)-7-[3-(4-cyanomethylpiperazin-1-yl)propoxy]-6-methoxyquinazoline, 4-(6-chloro-2,3-methylenedioxyanilino)-6-methoxy-7-(3-pyrrolidin-1-ylpropoxy)quinazoline, 4-(6-chloro-2,3-methylenedioxyanilino)-6-methoxy-7-(3-piperidinopropoxy)quinazoline, 4-(6-bromo-2,3-methylenedioxyanilino)-6-methoxy-7-(3-piperidinopropoxy)quinazoline, 6-methoxy-4-(2,3-methylenedioxyanilino)-7-[2-(N-methylpiperidin-4-yl)ethoxy]quinazoline, 6-methoxy-4-(2,3-methylenedioxyanilino)-7-[2-(4-pyridyloxy)ethoxy]quinazoline, 6-methoxy-4-(2,3-methylenedioxyanilino)-7-(3-pyridylmethoxy)quinazoline, 4-(6-chloro-2,3-methylenedioxyanilino)-7-(2cyanopyrid-4-ylmethoxy)-6-methoxyquinazoline and 4-(6-chloro-2,3-methylenedioxyanilino)-6-methoxy-7-(N-methylpiperidin-4-ylmethoxy)quinazoline;

or a pharmaceutically-acceptable acid-addition salt thereof.

14. A process for the preparation of a quinazoline derivative of the Formula I, or a pharmaceutically-acceptable salt thereof, according to claim 1 which comprises:

(a) the reaction of a quinazoline of the Formula II

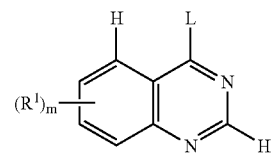

II wherein L is a displaceable group and m and $R^1$ have any of the meanings defined in claim 1 except that any functional group is protected if necessary, with an aniline of the Formula III

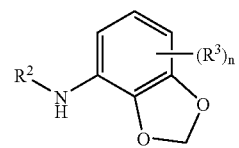

III wherein $R^2$, n and $R^3$ have any of the meanings defined in claim 1 except that any functional group is protected if necessary, whereafter any protecting group that is present is removed;

(b) for the production of those compounds of the Formula I wherein at least one $R^1$ group is a group of the formula $Q^1$-$X^1$— wherein $Q^1$ is an aryl-(1–6C)alkyl, (3–7C)cycloalkyl-(1–6C)alkyl, (3–7C)cycloalkenyl-(1–6C)alkyl, heteroaryl-(1–6C)alkyl or heterocyclyl-(1–6C)alkyl group or an optionally substituted alkyl group and $X^1$ is an oxygen atom, the coupling of a quinazoline of the Formula V

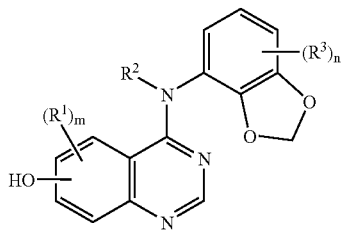

wherein m, $R^1$, $R^2$, n and $R^3$ have any of the meanings defined in claim 1 except that any functional group is protected if necessary, with an appropriate alcohol wherein any functional group is protected if necessary whereafter any protecting group that is present is removed;

(c) for the production of those compounds of the Formula I wherein $R^1$ is an amino-substituted (1–6C)alkoxy group, the reaction of a compound of the Formula I wherein $R^1$ is a halogeno-substituted (1–6C)alkoxy group with a heterocyclyl compound or an appropriate amine;

(d) for the production of those compounds of the Formula I wherein $R^1$ is a hydroxy group, the cleavage of a quinazoline derivative of the Formula I wherein $R^1$ is a (1–6C)alkoxy or arylmethoxy group;

(e) for the production of those compounds of the Formula I wherein an $R^1$ group contains a primary or secondary amino group, the cleavage of the corresponding compound of the Formula I wherein the $R^1$ group contains a protected primary or secondary amino group;

(f) for the production of those compounds of the Formula I wherein an $R^1$ group contains a (1–6C)alkoxy or substituted (1–6C)alkoxy group or a (1–6C)alkylamino or substituted (1–6C)alkylamino group, the alkylation of a quinazoline derivative of the formula I wherein the $R^1$ group contains a hydroxy group or a primary or secondary amino group as appropriate;

(g) for the production of those compounds of the Formula I wherein $R^1$ is an amino-hydroxy-disubstituted (1–6C)alkoxy group, the reaction of a compound of the Formula I wherein the $R^1$ group contains an epoxy-substituted (1–6C)alkoxy group with a heterocyclyl compound or an appropriate amine; or (h) for the production of those compounds of the Formula I wherein an $R^1$ group contains a hydroxy group, the cleavage of the corresponding compound of the Formula I wherein the $R^1$ group contains a protected hydroxy group;

and optionally forming a pharmaceutically-acceptable salt of a quinazoline derivative of the Formula I.

15. A pharmaceutical composition which comprises a quinazoline derivative of the Formula I, or a pharmaceutically-acceptable thereof, as defined in claims 1–13 in association with a pharmaceutically-acceptable diluent or carrier.

16. A method for the treatment of solid tumour disease in a warm-blooded animal in need of such treatment which comprises administering to said animal an effective amount of a quinazoline derivative of the Formula I, or a pharmaceutically-acceptable salt thereof, as defined in any one of claims 1–13.

17. A method for the inhibition of growth of a solid tumour in a warm-blooded animal in need of such treatment, which comprises administering to said animal an effective amount of a quinazoline derivative of the Formula I, or a pharmaceutically-acceptable salt thereof, as defined in any one of claims 1–13.

18. A method for treating a solid tumour sensitive to inhibition of one or more non-receptor tyrosine kinases in a warm-blooded animal in need of such treatment which comprises administering to said animal an effective amount of a quinazoline derivative of the Formula I, or a pharmaceutically-acceptable salt thereof, as defined in any one of claims 1–13.

* * * * *